United States Patent
Forrest et al.

(10) Patent No.: US 11,605,787 B2
(45) Date of Patent: Mar. 14, 2023

(54) ORGANIC PHOTOVOLTAIC CELLS AND NON-FULLERENE ACCEPTORS THEREOF

(71) Applicant: The Regents of the University of Michigan, Ann Arbor, MI (US)

(72) Inventors: Stephen R. Forrest, Ann Arbor, MI (US); Yongxi Li, Ann Arbor, MI (US); Xiao Liu, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 289 days.

(21) Appl. No.: 16/761,914

(22) PCT Filed: Nov. 5, 2018

(86) PCT No.: PCT/US2018/059222
§ 371 (c)(1),
(2) Date: May 6, 2020

(87) PCT Pub. No.: WO2019/090229
PCT Pub. Date: May 9, 2019

(65) Prior Publication Data
US 2020/0328356 A1    Oct. 15, 2020

Related U.S. Application Data

(60) Provisional application No. 62/582,212, filed on Nov. 6, 2017.

(51) Int. Cl.
*H01L 51/00* (2006.01)
*C07D 495/22* (2006.01)
*H01L 27/30* (2006.01)
*H01L 51/42* (2006.01)

(52) U.S. Cl.
CPC ........ *H01L 51/0074* (2013.01); *C07D 495/22* (2013.01); *H01L 51/0053* (2013.01); *H01L 27/302* (2013.01); *H01L 51/4253* (2013.01)

(58) Field of Classification Search
None
See application file for complete search history.

(56) References Cited

U.S. PATENT DOCUMENTS

| 9,705,096 | B2 | 7/2017 | Youfu |
| 2009/0165857 | A1 | 7/2009 | Naito |
| 2016/0233448 | A1 | 8/2016 | Yang |
| 2016/0260912 | A1 | 9/2016 | Arai |

FOREIGN PATENT DOCUMENTS

CN    106467547    *   3/2017   ........... C07D 495/22

OTHER PUBLICATIONS

Liao et al., Chemical Abstract 166:316,483, Non-fullerene solar cell receptor materials based on multi-fused ring, their preparation method and application (Year: 2017).*
Li et al., A Near-Infrared Non-Fullerene Acceptor for High Performance Polymer Solar Cells, Energy Environ. Sci., 2017,10(7):1610-1620.
Li et al., High Efficiency Near-Infrared and Semitransparent Non-Fullerene Acceptor Organic Photovoltaic Cells, J. Am. Chem. Soc., 2017, 139(47):17114-19.

* cited by examiner

*Primary Examiner* — Zinna Northington Davis
(74) *Attorney, Agent, or Firm* — Riverside Law LLP

(57) ABSTRACT

Organic photovoltaic cells (OPVs) and their compositions are described herein. In one or more embodiments, the acceptor with an active layer of an OPV includes is a non-fullerene acceptor. Such non-fullerene acceptors may provide improved OPV performance characteristics such as improved power conversion efficiency, open circuit voltage, fill factor, short circuit current, and/or external quantum efficiency. One example of a non-fullerene acceptor is (4,4,10,10-tetrakis(4-hexylphenyl)-5,11-(2-ethylhexyloxy)-4,10-dihydro-dithienyl[1,2-b:4,5b'] benzodi-thiophene-2,8-diyl) bis(2-(3-oxo-2,3-dihydroinden-5,6-dichloro-1-ylidene) malononitrile.

20 Claims, 14 Drawing Sheets

100 Single-junction Organic Photovoltaic Cell

200 Multi-junction/Tandem Organic Photovoltaic Cell

ORGANIC PHOTOVOLTAIC CELLS AND NON-FULLERENE ACCEPTORS THEREOF

CROSS-REFERENCE TO RELATED APPLICATIONS

This application is a U.S. national phase application filed under 35 U.S.C. § 371 claiming benefit to PCT International Patent Application No PCT/US2018/059222, filed Nov. 5, 2018, which claims the benefit of U.S. Provisional Application No. 62/582,212, filed Nov. 6, 2017, each of which is hereby incorporated by reference in its entirety.

STATEMENT REGARDING FEDERALLY SPONSORED RESEARCH

This invention was made with government support under DE-EE0006708 awarded by the U.S. Department of Energy and N00014-17-1-2211 awarded by the Office of Naval Research. The government has certain rights in the invention.

TECHNICAL FIELD

The present disclosure generally relates to electrically active, optically active, solar, and semiconductor devices, and in particular, to organic photovoltaic cells and near-infrared non-fullerene acceptor compositions in such organic photovoltaic cells.

BACKGROUND

Optoelectronic devices rely on the optical and electronic properties of materials to either produce or detect electromagnetic radiation electronically or to generate electricity from ambient electromagnetic radiation.

Photosensitive optoelectronic devices convert electromagnetic radiation into electricity. Solar cells, also called photovoltaic (PV) devices or cells, are a type of photosensitive optoelectronic device that is specifically used to generate electrical power. PV devices, which may generate electrical energy from light sources other than sunlight, may be used to drive power consuming loads to provide, for example, lighting, heating, or to power electronic circuitry or devices such as calculators, radios, computers or remote monitoring or communications equipment. These power generation applications may involve the charging of batteries or other energy storage devices so that operation may continue when direct illumination from the sun or other light sources is not available, or to balance the power output of the PV device with the specific applications requirements.

Traditionally, photosensitive optoelectronic devices have been constructed of a number of inorganic semiconductors, e.g., crystalline, polycrystalline and amorphous silicon, gallium arsenide, cadmium telluride, and others.

More recent efforts have focused on the use of organic photovoltaic (OPV) cells to achieve acceptable photovoltaic conversion efficiencies with economical production costs. OPVs offer a low-cost, light-weight, and mechanically flexible route to solar energy conversion. Compared with polymers, small molecule OPVs share the advantage of using materials with well-defined molecular structures and weights. This leads to a reliable pathway for purification and the ability to deposit multiple layers using highly controlled thermal deposition without concern for dissolving, and thus damaging, previously deposited layers or subcells.

In addition to the pursuit of high device efficiency, OPVs have unique advantages, such as the application of semi-transparent solar cells for use in building integrated photovoltaics (BIPV). Considering the vast surface areas of windows and facades in modern urban environments, developing semi-transparent solar cells with both high efficiency and transmittance has become increasingly important. For a solar cell to be highly transparent, visible light would have to travel uninhibited to the eye, and hence cannot be absorbed. Selectively harvesting near-infrared (NIR) radiation avoids competition between efficiency and transmittance. However, the lack of high performance NIR absorbers in conventional fullerene based OPVs has prevented the attainment of efficient, yet highly transparent (in the visible) devices. To date, semi-transparent OPVs based on fullerene acceptors show only PCE less than or equal to 4% with average visible transmittance of 61%.

Progress in developing small energy gap non-fullerene acceptors (NFAs) provides new opportunities to achieve both high efficiency and transparency. However, most NFAs strongly absorb in the UV-Vis range, whereas NFAs with an absorption cut-off in the NIR region are rare. Yao et al. in Angew. Chem. Int. Ed., Vol. 56, p. 3045 (2017) has reported acceptor-π-bridge-donor-π-bridge-acceptor (a-π-d-π-a) NFAs with absorption edges extending to approximately 1000 nm. Due to the large torsion angles between both of the π-bridges and the donor and acceptor units, the twisted molecular conformation led to a reduced charge mobility and fill factor (FF), thus reducing the PCE.

SUMMARY

Organic photovoltaic cells (OPVs) and their compositions are described herein. In one or more embodiments, an acceptor of an active layer of an OPV includes one of the following structures:

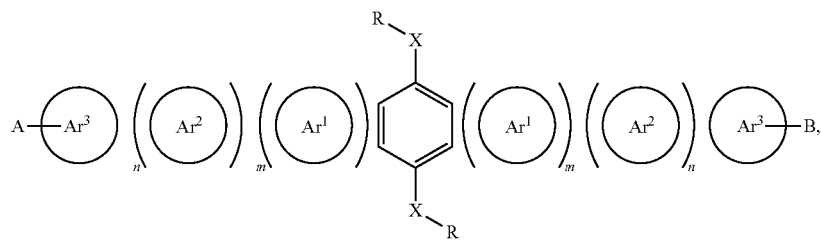

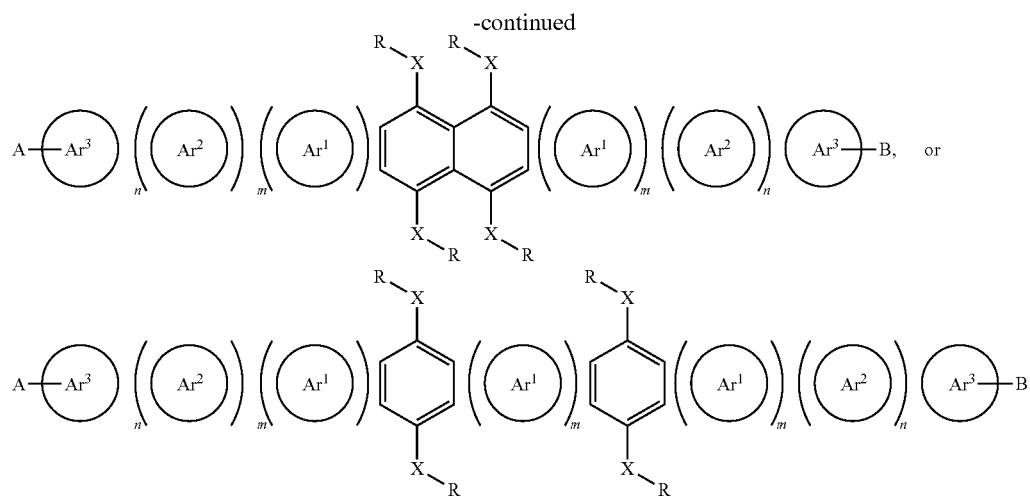
wherein:
A or B is individually selected from the group consisting of:
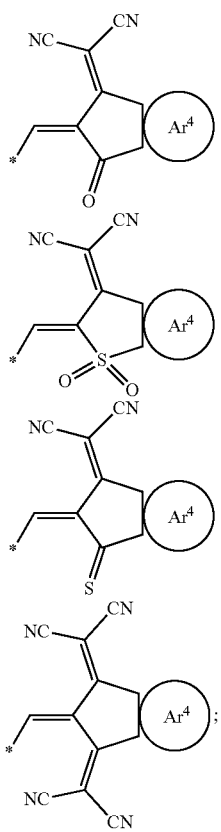
each Ar¹ is individually selected from the group consisting of:
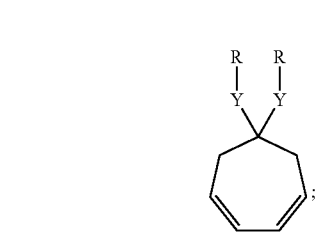
-continued
each Ar² is individually selected from the group consisting of:
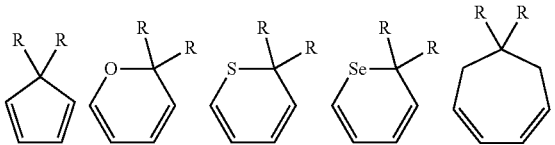
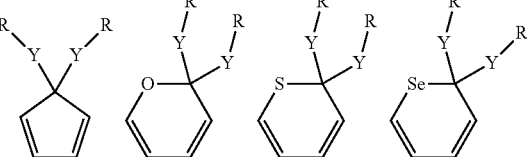
each Ar³ is individually selected from the group consisting of:

each $Ar^4$ is individually selected from the group consisting of:

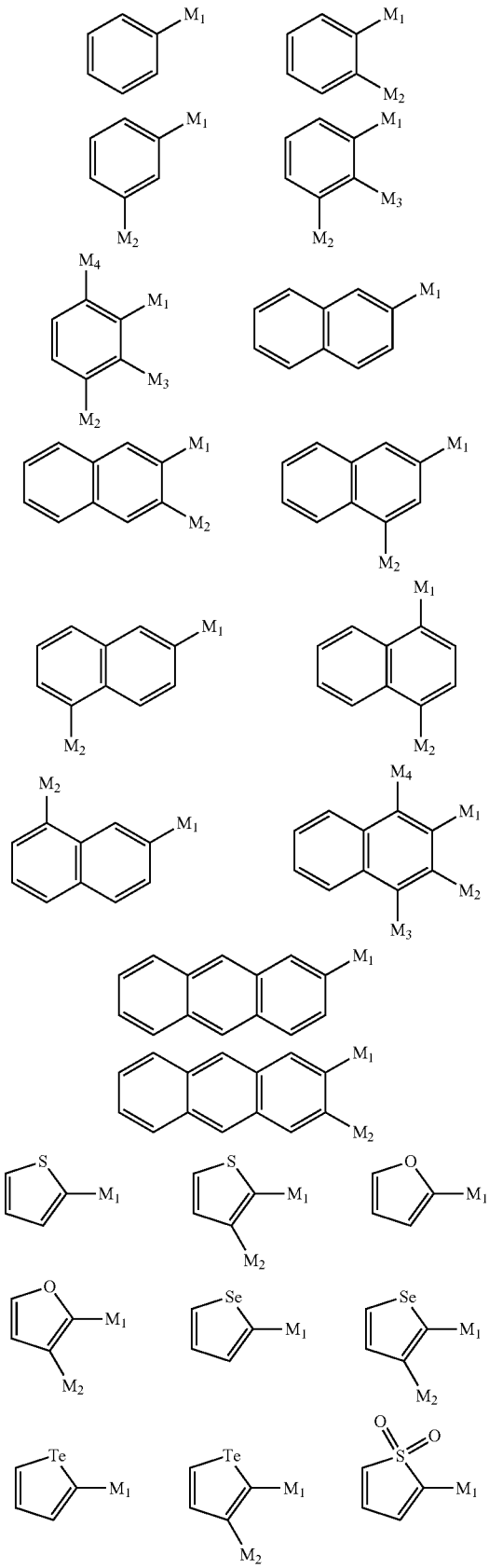

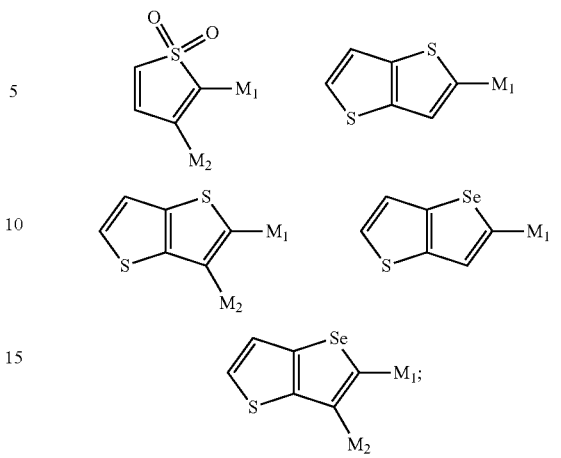

$M_1$-$M_4$ are individually selected from the group consisting of hydrogen, fluorine, chlorine, bromine, iodine, astatine, and a cyano group, wherein at least one of $M_1$-$M_4$ is a halogen;

each R is individually a $C_1$-$C_{20}$ hydrocarbon or an aromatic hydrocarbon;

each X is individually selected from the group consisting of oxygen, carbon, hydrogen, sulfur, selenium, and nitrogen;

each Y is individually selected from the group consisting of:

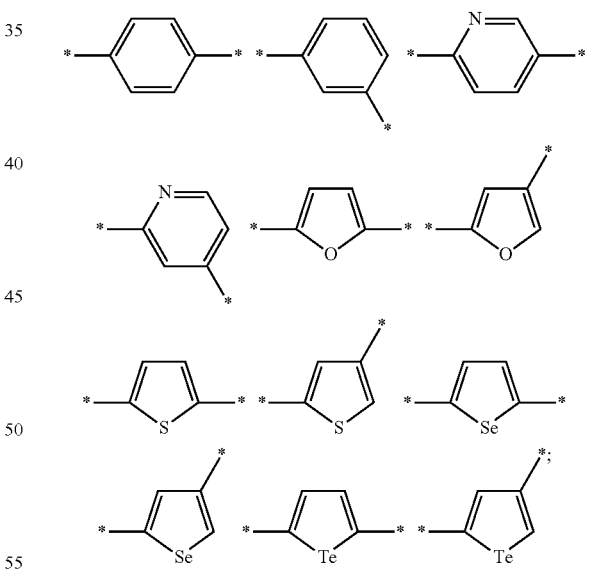

each m is an integer from 0 to 10; and
each n is an integer from 0 to 10.

In certain embodiments, each $Ar^1$ is individually:

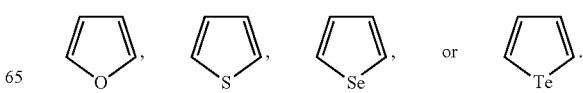

In certain embodiments, each Ar¹ is:

In certain embodiments, each Ar² is individually:

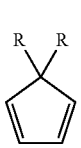 or 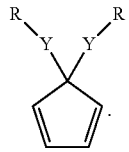

In certain embodiments, each Ar² is individually:

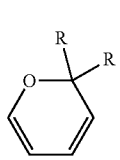 or 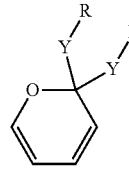

In certain embodiments, each Ar³ is individually:

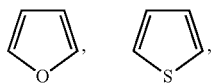

In certain embodiments, each Ar³ is:

In certain embodiments, m is from 1 to 2.
In certain embodiments, m is 1.
In certain embodiments, n is 1.
In certain embodiments, A or B is:

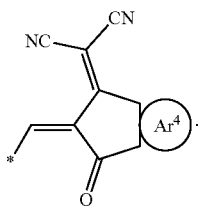 [SMILES: */C=C1\C(=O)CCC1=C(C#N)C#N]

In certain embodiments, each Ar⁴ is individually selected from the group consisting of:

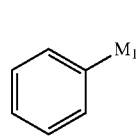 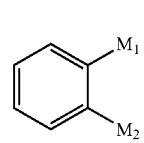 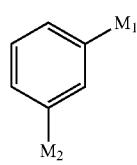

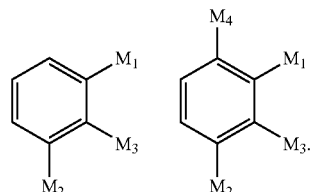

In certain embodiments, each Ar⁴ is:

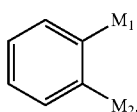

In certain embodiments, A or B is:

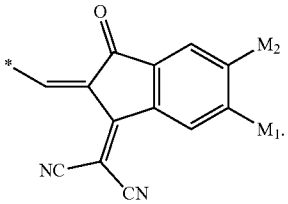

In certain embodiments, each $M_1$-$M_4$ is a halogen. In some embodiments, the halogen is chloride.

In certain embodiments, at least one of $M_1$-$M_4$ is chloride.

In certain embodiments, each X is oxygen.

In certain embodiments, each R is individually a $C_1$-$C_{20}$ hydrocarbon.

In certain embodiments, each R is 2-ethylhexyl.

In certain embodiments, each R is individually an aromatic hydrocarbon.

In certain embodiments, each R is selected from the group consisting of:

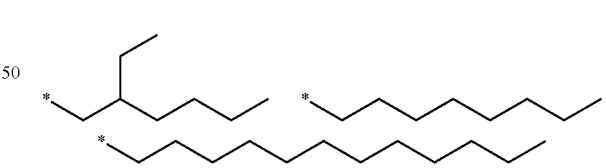

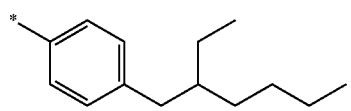

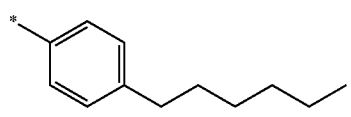

-continued
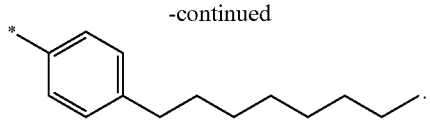
In certain embodiments, each Y is:
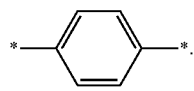
In certain embodiments, each Y—R is:
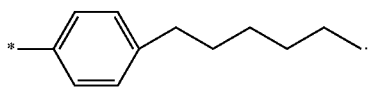
In certain embodiments, the acceptor has one of the following structures C1-C11:
C1
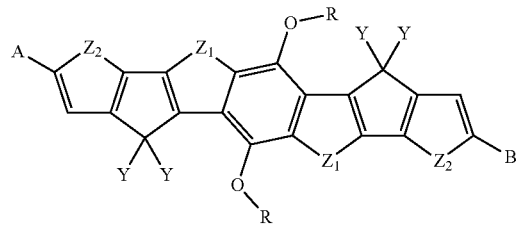
C2
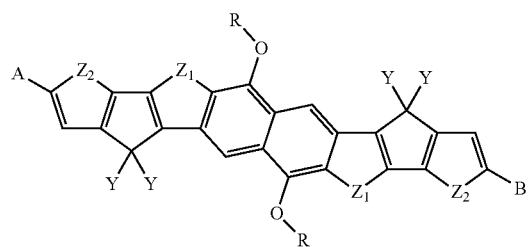
C3
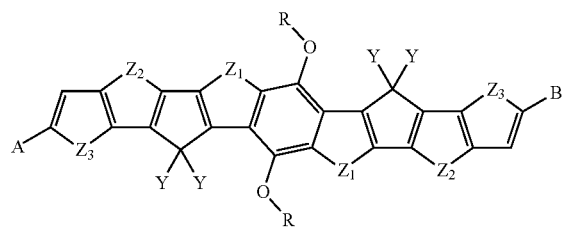
C4
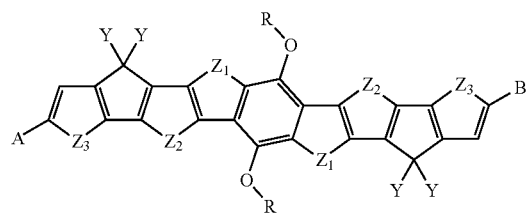
C5
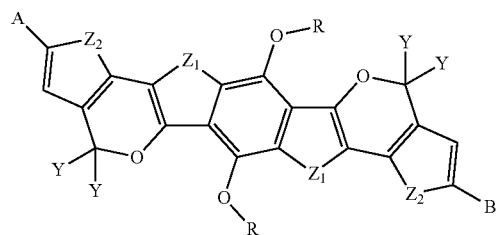
C6
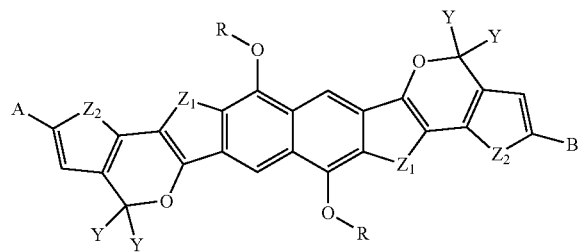
C7
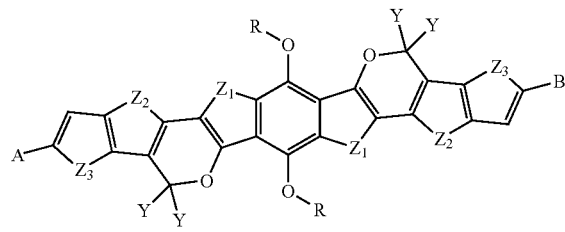
C8
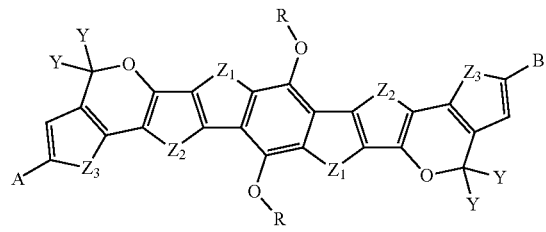
C9
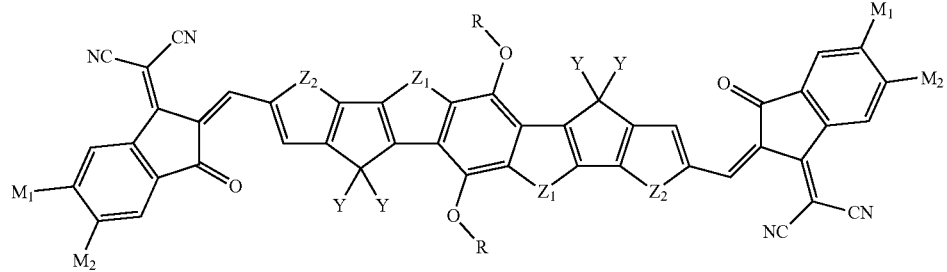

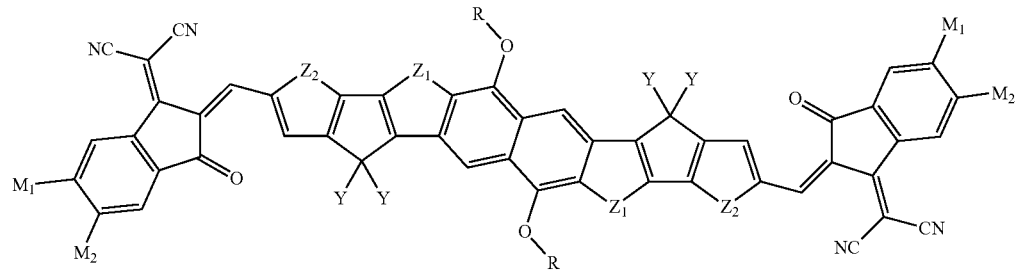
C10
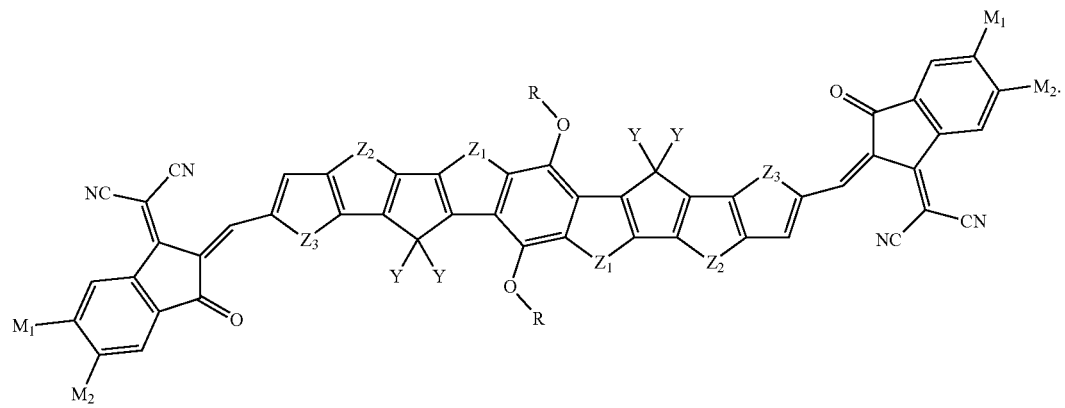
C11
In certain embodiments, $Z_1$, $Z_2$, and $Z_3$ are individually selected from the group consisting of oxygen, sulfur, selenium, or tellurium.
In certain embodiments, $Z_1$, $Z_2$, and $Z_3$ are sulfur.
In certain embodiments, the acceptor has one of the following structures:
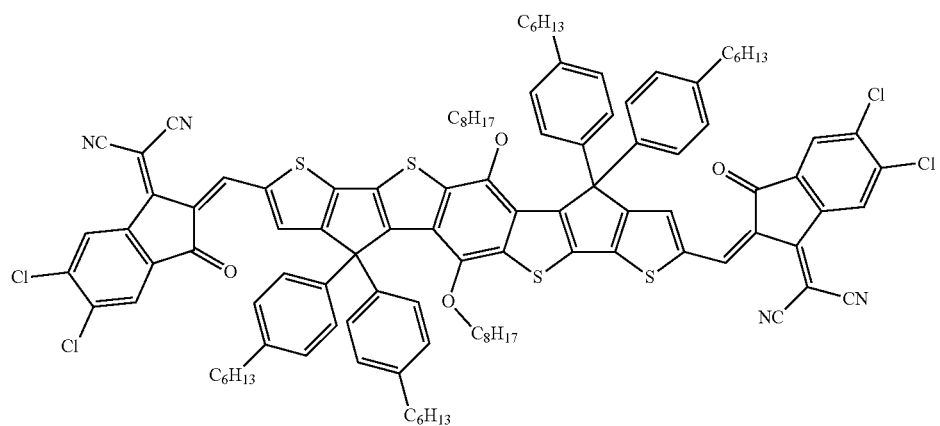

-continued
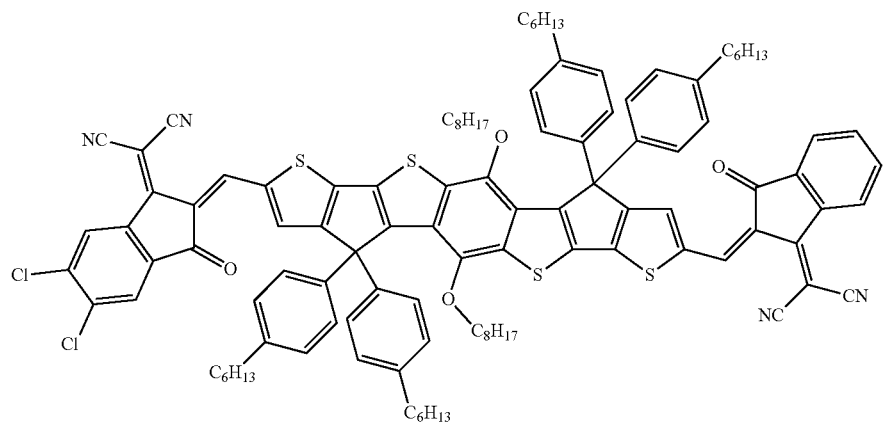
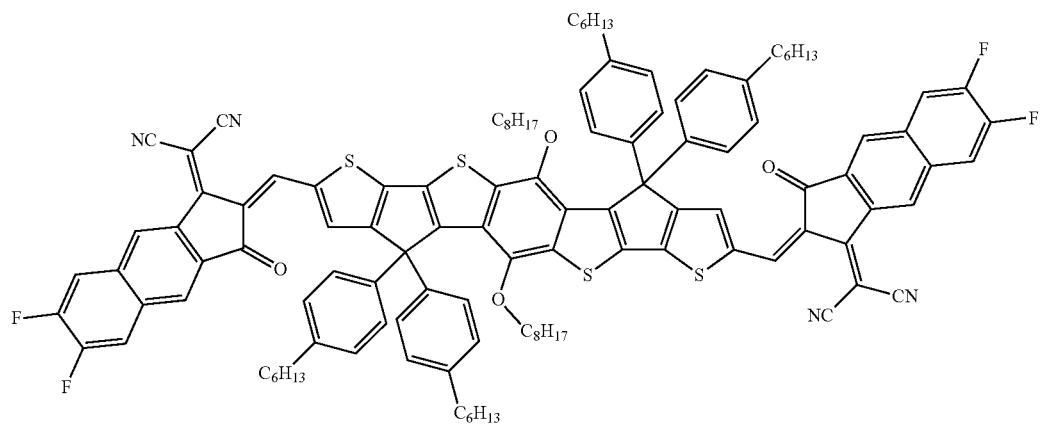
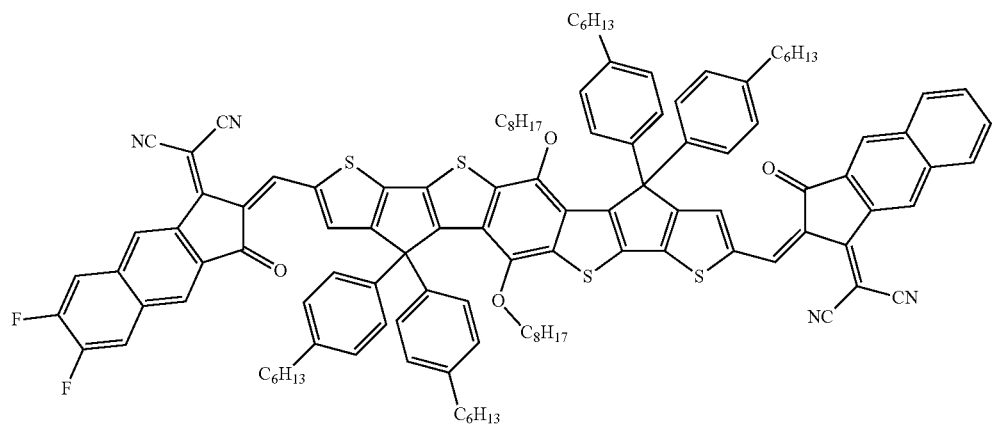
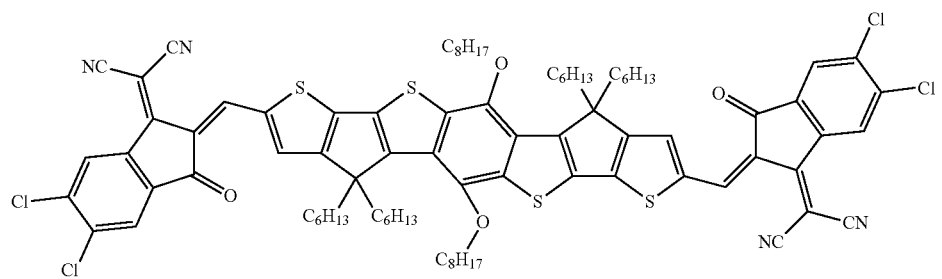

-continued
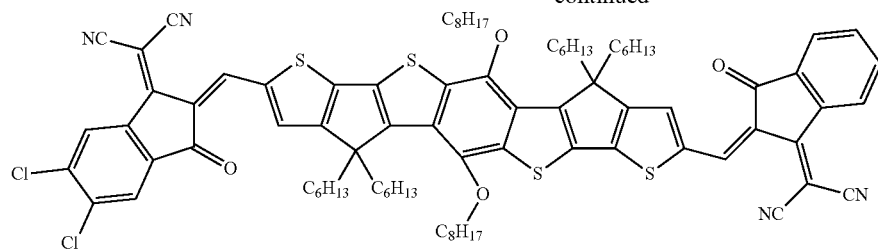
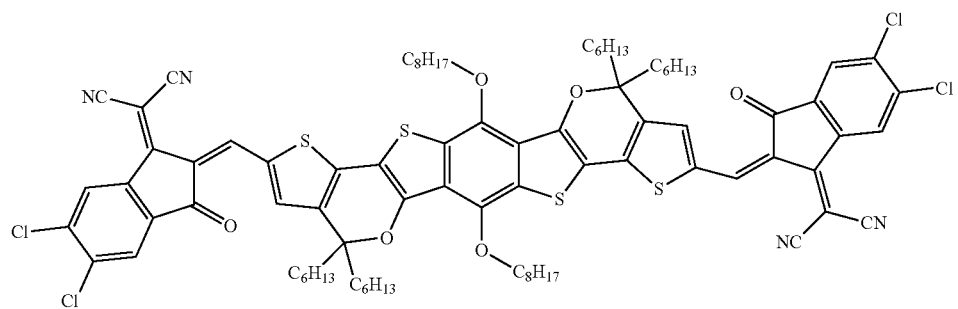
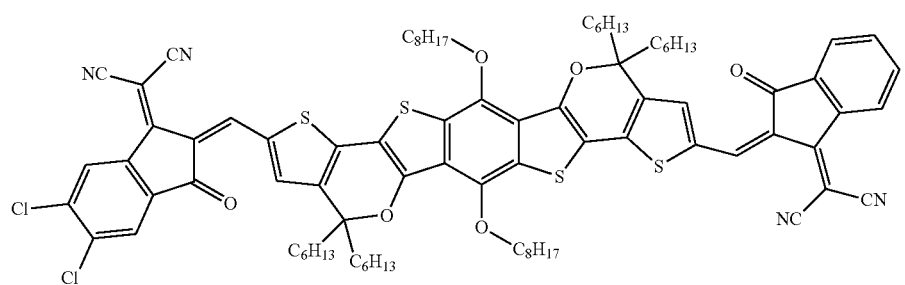
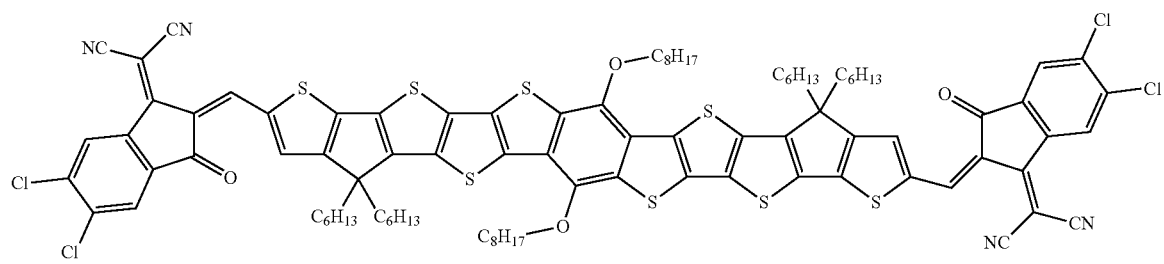
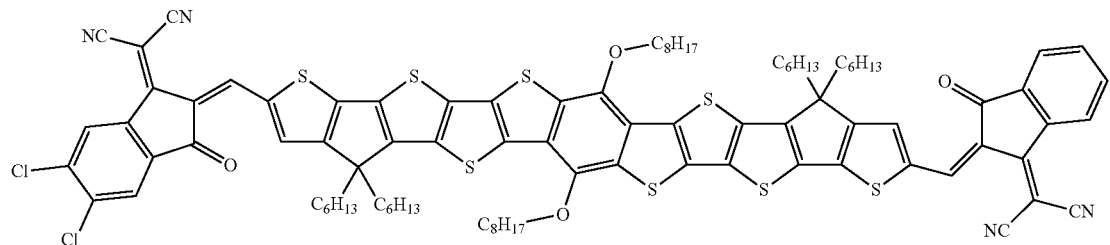
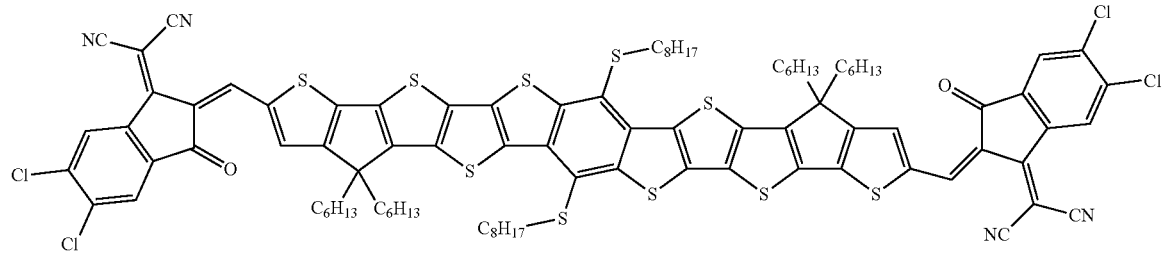

-continued
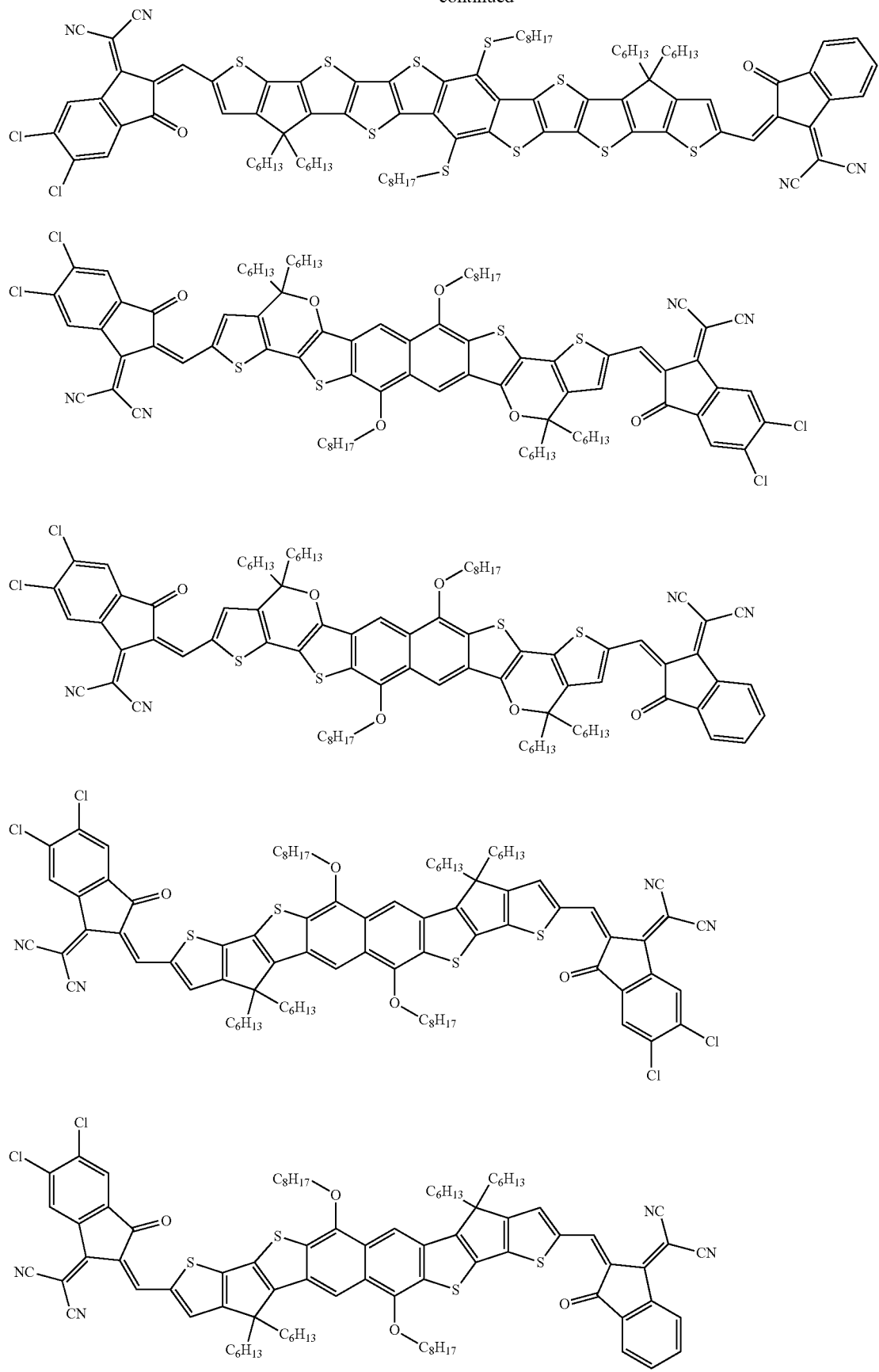

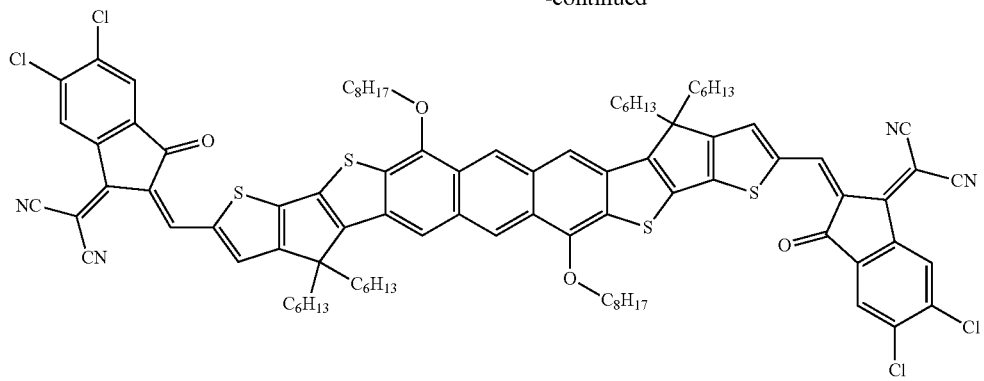

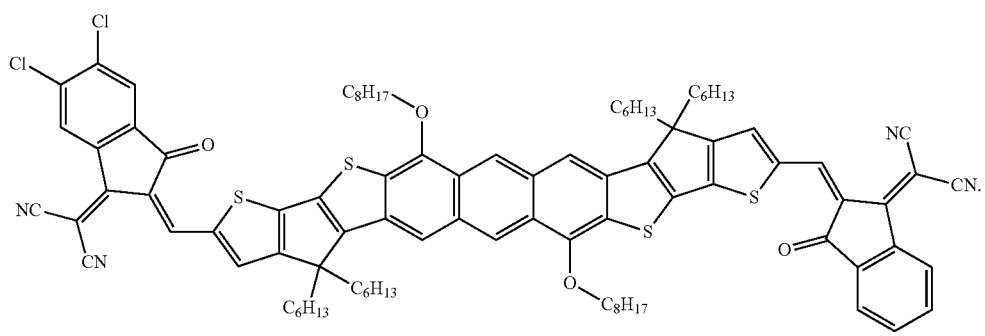

In certain embodiments, the acceptor has the following structure:

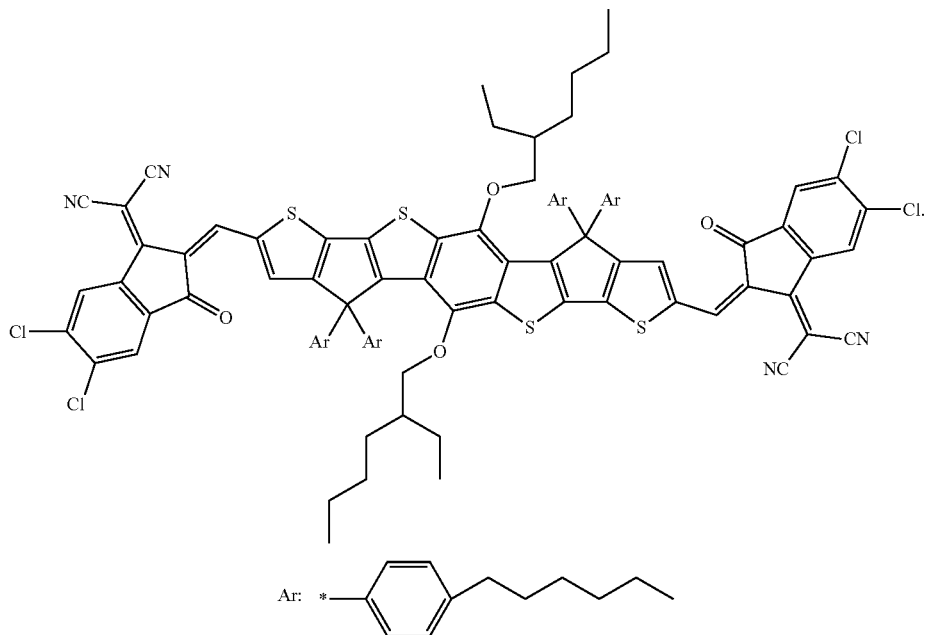

In certain embodiments, the solar cell having the acceptor has a power conversion efficiency of at least 11, or between 10-12%.

In certain embodiments, the solar cell having the acceptor has an open circuit voltage of at least 0.7 Volts, or between 0.6-0.9 Volts.

In certain embodiments, the solar cell having the acceptor has a fill factor of at least 70%, or between 65-75%.

In certain embodiments, the solar cell having the acceptor has a short circuit current of between 20-25 mA/cm$^2$, or between 22-23 mA/cm$^2$.

In certain embodiments, the solar cell having the acceptor has an external quantum efficiency of at least 75% or between 70-80%, as measured between wavelengths of 650-850 nm and providing a transparency window between wavelengths of 400-650 nm.

In certain embodiments, a length of the acceptor is at least 25 angstroms, or between 25-35 angstroms.

In another embodiment, the acceptor within the active layer of an OPV is (4,4,10,10-tetrakis(4-hexylphenyl)-5,11-(2-ethylhexyloxy)-4,10-dihydro-dithienyl[1,2-b:4,5b'] benzodi-thiophene-2,8-diyl) bis(2-(3-oxo-2,3-dihydroinden-5,6-dichloro-1-ylidene) malononitrile.

In yet another embodiment, a solar cell or OPV includes an anode; a cathode; and an active material positioned between the anode and cathode, wherein the active material comprises a non-fullerene acceptor and a donor, the non-fullerene acceptor having one of the following structures referenced herein.

In certain embodiments, the anode is a conductive metal oxide, a metal layer, or a conducting polymer. In certain embodiments, the anode is the conductive metal oxide selected from the group consisting of indium tin oxide, tin oxide, gallium indium tin oxide, zinc oxide, or zinc indium tin oxide. In some embodiments, the anode is the metal layer selected from the group consisting of Ag, Au, Pd, Pt, Ti, V, Zn, Sn, Al, Co, Ni, Cu, Cr, or combinations thereof.

In certain embodiments, the cathode is a conductive metal oxide, a metal layer, or a conducting polymer. In some embodiments, the cathode is the conductive metal oxide selected from the group consisting of indium tin oxide, tin oxide, gallium indium tin oxide, zinc oxide, or zinc indium tin oxide. In other embodiments, the cathode is the metal layer selected from the group consisting of Ag, Au, Pd, Pt, Ti, V, Zn, Sn, Al, Co, Ni, Cu, Cr, or combinations thereof.

In certain embodiments, the solar cell or OPV further includes a first intermediate layer positioned between the anode and the active material, and a second intermediate layer positioned between the active material and the cathode.

In some embodiments, the first intermediate layer and the second intermediate layer are individually metal oxides. In other embodiments, the first intermediate layer and the second intermediate layer are individually selected from the group consisting of $MoO_3$, $V_2O_5$, ZnO, or $TiO_2$.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DESCRIPTION OF THE DRAWING FIGURES

For a more complete understanding of the disclosure, reference is made to the following detailed description and accompanying drawing figures, in which like reference numerals may be used to identify like elements in the figures.

Figure 1A:
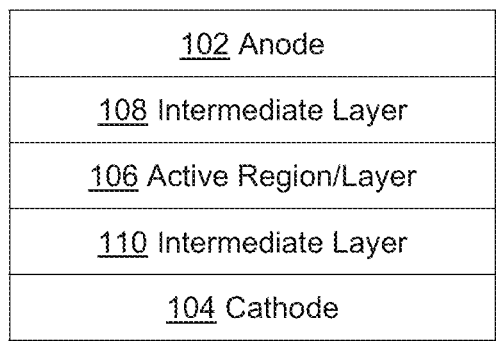
FIGS. 1A and 1B depict example of various layers or compositions within an organic photovoltaic cell.

While the disclosed devices and systems are representative of embodiments in various forms, specific embodiments are illustrated in the drawings (and are hereafter described), with the understanding that the disclosure is intended to be illustrative and is not intended to limit the claim scope to the specific embodiments described and illustrated herein.

DETAILED DESCRIPTION

Various non-limiting examples of OPVs and the acceptor-donor compositions within an OPV active layer are described in greater detail below.

Definitions

As used herein, the terms "electrode" and "contact" may refer to a layer that provides a medium for delivering photo-generated current to an external circuit or providing a bias current or voltage to the device. That is, an electrode, or contact, provides the interface between the active regions of an organic photosensitive optoelectronic device and a wire, lead, trace or other means for transporting the charge carriers to or from the external circuit. Examples of electrodes include anodes and cathodes, which may be used in a photosensitive optoelectronic device.

As used herein, the term "transparent" may refer to an electrode that permits at least 50% of the incident electromagnetic radiation in relevant wavelengths to be transmitted through it. In a photosensitive optoelectronic device, it may be desirable to allow the maximum amount of ambient electromagnetic radiation from the device exterior to be admitted to the photoconductive active interior region. That is, the electromagnetic radiation must reach a photoconductive layer(s), where it can be converted to electricity by photoconductive absorption. This often dictates that at least one of the electrical contacts should be minimally absorbing and minimally reflecting of the incident electromagnetic radiation. In some cases, such a contact should be transparent or at least semi-transparent.

As used herein, the term "semi-transparent" may refer to an electrode that permits some, but less than 50% transmission of ambient electromagnetic radiation in relevant wavelengths. The opposing electrode may be a reflective material so that light which has passed through the cell without being absorbed is reflected back through the cell.

As used and depicted herein, a "layer" refers to a member or component of a photosensitive device whose primary dimension is X-Y, i.e., along its length and width. It should be understood that the term layer is not necessarily limited to single layers or sheets of materials. In addition, it should be understood that the surfaces of certain layers, including the interface(s) of such layers with other material(s) or layers(s), may be imperfect, wherein said surfaces represent an interpenetrating, entangled or convoluted network with other material(s) or layer(s) Similarly, it should also be understood that a layer may be discontinuous, such that the continuity of said layer along the X-Y dimension may be disturbed or otherwise interrupted by other layer(s) or material(s).

As used herein, a "photoactive region" refers to a region of the device that absorbs electromagnetic radiation to generate excitons. Similarly, a layer is "photoactive" if it absorbs electromagnetic radiation to generate excitons. The excitons may dissociate into an electron and a hole in order to generate an electrical current.

As used herein, the terms "donor" and "acceptor" refer to the relative positions of the highest occupied molecular orbital ("HOMO") and lowest unoccupied molecular orbital ("LUMO") energy levels of two contacting but different organic materials. If the LUMO energy level of one material in contact with another is lower, then that material is an acceptor. Otherwise it is a donor. It is energetically favorable, in the absence of an external bias, for electrons at a donor-acceptor junction to move into the acceptor material, and for holes to move into the donor material.

As used herein, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Because ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, the term "band gap" ($E_g$) of a polymer may refer to the energy difference between the HOMO and the LUMO. The band gap is typically reported in electron-volts (eV). The band gap may be measured from the UV-vis spectroscopy or cyclic voltammetry. A "low band gap" polymer may refer to a polymer with a band gap below 2 eV, e.g., the polymer absorbs light with wavelengths longer than 620 nm.

As used herein, the term "excitation binding energy" ($E_B$) may refer to the following formula: $E_B=(M^++M^-)-(M^*+M)$, where $M^+$ and $M^-$ are the total energy of a positively and negatively charged molecule, respectively; $M^*$ and $M$ are the molecular energy at the first singlet state ($S_1$) and ground state, respectively. Excitation binding energy of acceptor or donor molecules affects the energy offset needed for efficient exciton dissociation. In certain examples, the escape yield of a hole increases as the HOMO offset increases. A decrease of exciton binding energy $E_B$ for the acceptor molecule leads to an increase of hole escape yield for the same HOMO offset between donor and acceptor molecules.

As used herein, power conversion efficiency ($\eta_P$) may be expressed as:

$$\eta_P = \frac{V_{OC}*FF*J_{SC}}{P_O}$$

wherein $V_{OC}$ is the open circuit voltage, FF is the fill factor, $J_{SC}$ is the short circuit current, and $P_O$ is the input optical power.

Organic Photovoltaic Cells

As disclosed herein, the various compositions or molecules within an active region or layer of a photovoltaic cell may be provided within a single junction solar cell or a tandem or multi-junction solar cell.

FIG. 1A depicts an example of various layers of a single junction solar cell or organic photovoltaic cell (OPV) 100 having a NIR non-fullerene acceptor composition. The OPV cell may include two electrodes having an anode 102 and a cathode 104 in superposed relation, at least one donor composition, and at least one acceptor composition, wherein the donor-acceptor material or active layer 106 is positioned between the two electrodes 102, 104. At least one intermediate layer 108 may be positioned between the anode 102 and the active layer 106. Additionally, or alternatively, at least one intermediate layer 110 may be positioned between the active layer 106 and cathode 104.

The anode 102 may include a conducting oxide, thin metal layer, or conducting polymer. In some examples, the anode 102 includes a (e.g., transparent) conductive metal oxide such as indium tin oxide (ITO), tin oxide (TO), gallium indium tin oxide (GITO), zinc oxide (ZO), or zinc indium tin oxide (ZITO). In other examples, the anode 102 includes a thin metal layer, wherein the metal is selected from the group consisting of Ag, Au, Pd, Pt, Ti, V, Zn, Sn, Al, Co, Ni, Cu, Cr, or combinations thereof. In yet other examples, the anode 102 includes a (e.g., transparent) conductive polymer such as polyanaline (PANI), or 3,4-polyethyl-enedioxythiophene:polystyrenesulfonate (PEDOT:PSS).

The thickness of the anode 102 may be 0.1-100 nm, 1-10 nm, 0.1-10 nm, or 10-100 nm.

The cathode 104 may be a conducting oxide, thin metal layer, or conducting polymer similar or different from the materials discussed above for the anode 102. In certain examples, the cathode 104 may include a metal or metal alloy. The cathode 104 may include Ca, Al, Mg, Ti, W, Ag, Au, or another appropriate metal, or an alloy thereof.

The thickness of the cathode 104 may be 0.1-100 nm, 1-10 nm, 0.1-10 nm, or 10-100 nm.

As noted above, the OPV may include one or more charge collecting/transporting intermediate layers positioned between an electrode 102, 104 and the active region or layer 106. The intermediate layer 108, 110 may be a metal oxide. In certain examples, the intermediate layer 108, 110 includes $MoO_3$, $V_2O_5$, ZnO, or $TiO_2$. In some examples, the first intermediate layer 108 has a similar composition as the second intermediate layer 110. In other examples, the first and second intermediate layers 108, 110 have different compositions.

The thickness of each intermediate layer may be 0.1-100 nm, 1-10 nm, 0.1-10 nm, or 10-100 nm.

The active region or layer 106 positioned between the electrodes 102, 104 includes a composition or molecule having an acceptor and a donor. The composition may be arranged as an acceptor-donor-acceptor (A-D-A).

Figure 1B:
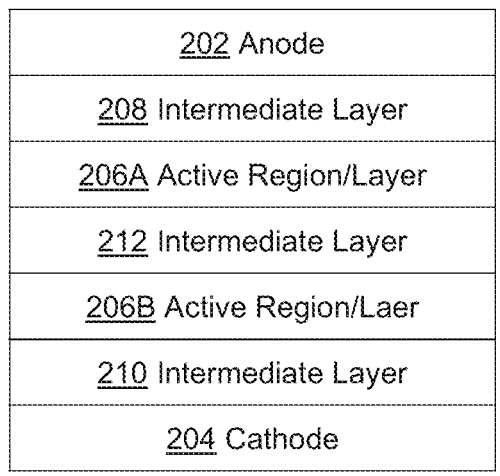

FIG. 1B depicts an example of various layers of a tandem or multi junction solar cell or organic photovoltaic cell (OPV) 200 having a NIR non-fullerene acceptor composition. The OPV cell may include two electrodes having an anode 202 and a cathode 204 in superposed relation, at least one donor composition, and at least one acceptor composition positioned within a plurality of active layers or regions 206A, 206B between the two electrodes 202, 204. While only two active layers or regions 206A, 206B are depicted in FIG. 1B, additional active layers or regions are also possible.

At least one intermediate layer 208 may be positioned between the anode 202 and a first active layer 206A. Additionally, or alternatively, at least one intermediate layer 210 may be positioned between the second active layer 206B and cathode 204.

At least one intermediate layer 212 may be positioned between the first active layer 206A and the second active layer 206B.

The compositions, thicknesses, etc. of each layer may be the same as those discussed with reference to FIG. 1A.

The active region or layer 106, 206A, 206B positioned between the electrodes includes a composition or molecule having an acceptor and a donor. The composition may be arranged as an acceptor-donor-acceptor (A-D-A).

As disclosed herein, the acceptor is a non-fullerene acceptor composition. Various examples of donor and non-fullerene acceptor compositions are discussed in greater detail below.

Donor Composition

In certain examples, the donor material or composition within the active layer or region 106 is a low energy band gap polymer composition. For example, the donor composition is a polymer having a band gap of less than 2 eV.

One non-limiting example of low band gap polymer donor is poly [4,8-bis(5-(2-ethylhexyl)thiophen-2-yl)benzo [1,2-b:4,5-b']dithiophene-co-3-fluorothieno[3,4-b]thiophene-2-carboxylate, or a derivative thereof.

Other non-limiting examples of low band gap polymer donors include the compounds depicted below in P1-P9, and their derivatives:

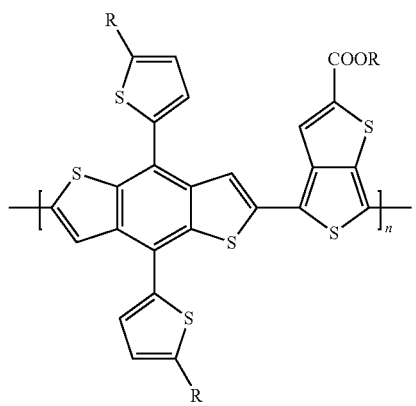

P1

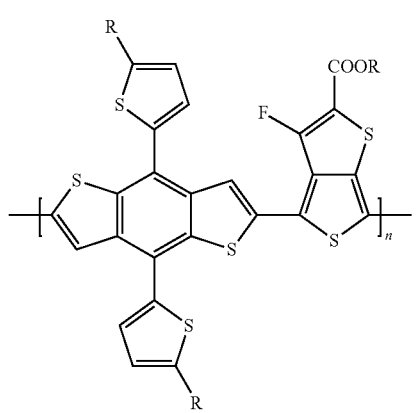

P2

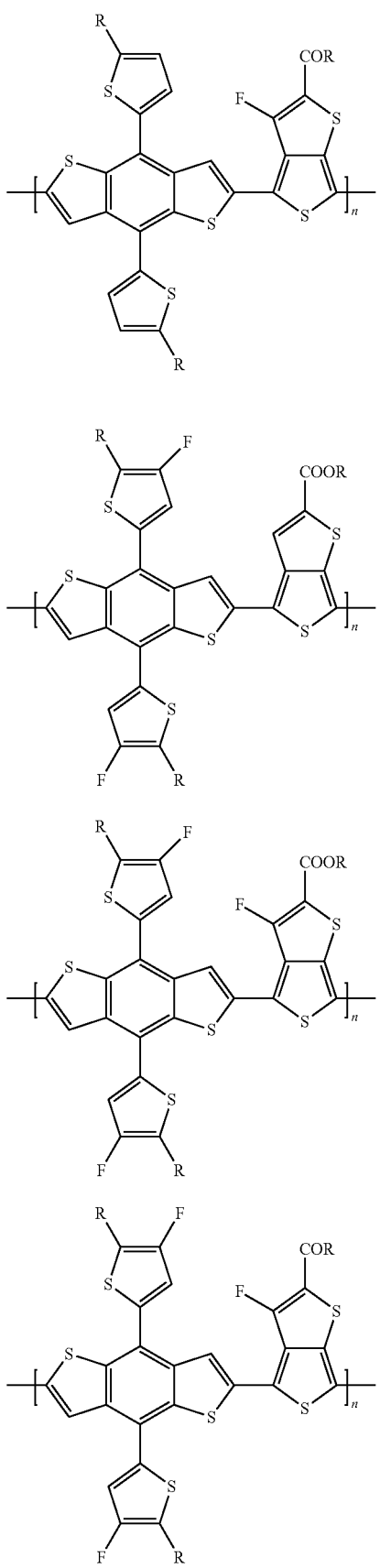

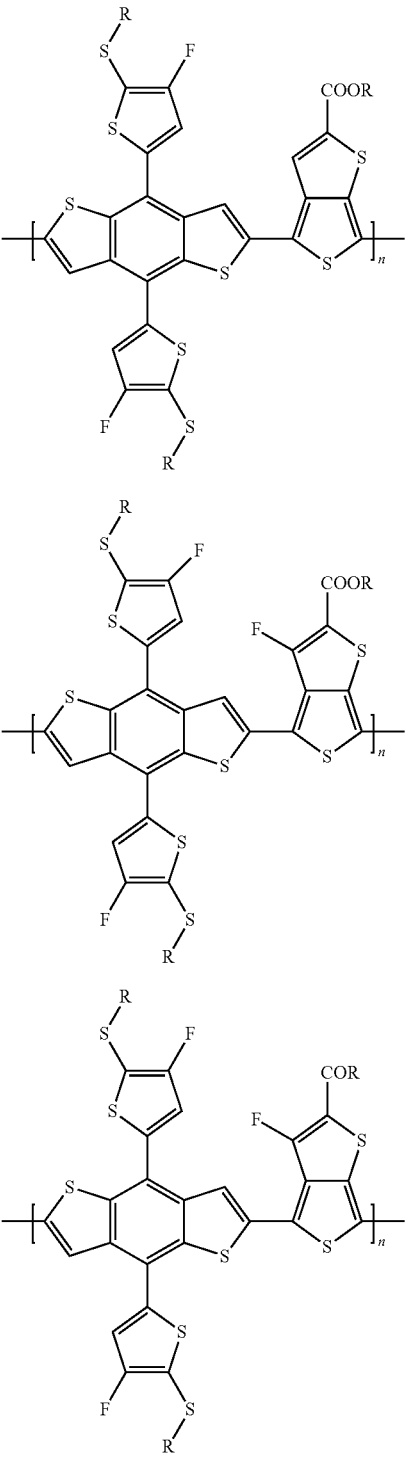

In the polymers depicted in P1-P9, n refers to the degree of polymerization. In some examples, n is within a range of 1-1000, 1-100, or 10-1000.

Additionally, R may represent a linear or branched saturated or unsaturated non-aromatic hydrocarbon, e.g., within the $C_2$-$C_{20}$ range. In certain examples, R represents a saturated hydrocarbon or alkyl group. Examples of linear or branched alkyl groups in the $C_2$-$C_{20}$ range include methyl, ethyl, n-propyl, isopropyl, isobutyl, n-butyl, sec-butyl, tert-butyl, isopentyl, n-pentyl, neopentyl, n-hexyl, and 2-ethylhexyl. In one particular example, R represents 2-ethylhexyl.

Non-fullerene Acceptor Composition

The acceptor in the active layer or material 106 may be a non-fullerene acceptor composition. In other words, the structure of acceptor composition does not form a hollow sphere, ellipsoid, or tube.

In certain examples, the non-fullerene acceptor composition is a compound having one of the following three structures (I, II, or III):

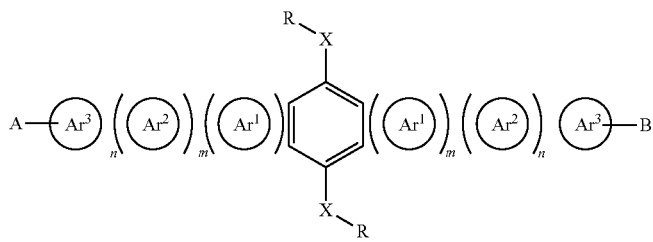

Structure I

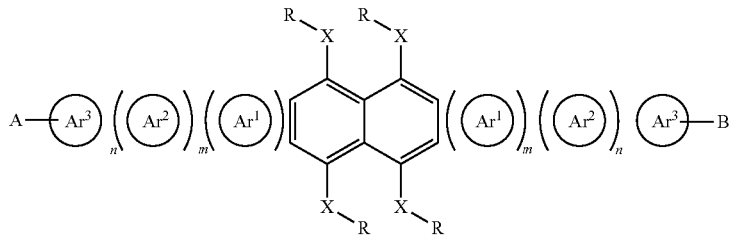

Structure II

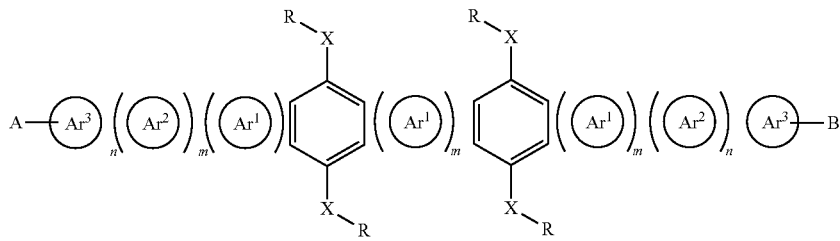

Structure III

In these structures, $Ar^1$, $Ar^2$, and $Ar^3$ individually represent aromatic groups. The aromatic groups may be 5- or 6-membered cyclic rings. The cyclic rings may also be heterocyclic rings, wherein one carbon has been replaced by a non-carbon atom. In certain examples, the non-carbon atom within the heterocyclic ring may be nitrogen or a chalcogen such as oxygen, sulfur, selenium, or tellurium.

$Ar^1$ may include an aromatic group which is conjugated fused connected to a benzene ring in the compound. Each $Ar^1$ may be individually selected from the group consisting of:

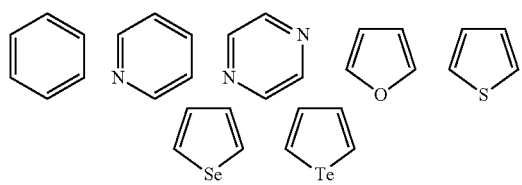

$Ar^2$ may include an aromatic group which is conjugated fused connected to a $Ar^1$ ring in the compound. Each $Ar^2$ may be individually selected from the group consisting of:

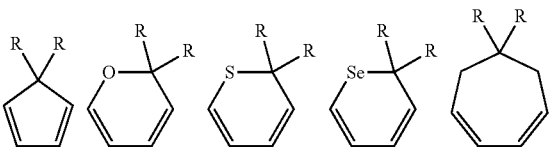

-continued

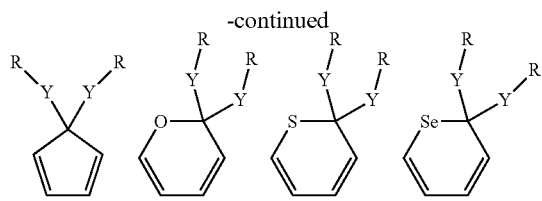

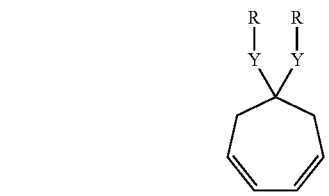

$Ar^3$ may include an aromatic group which is conjugated fused connected to a $Ar^2$ ring in the compound. Each $Ar^3$ may be individually selected from the group consisting of:

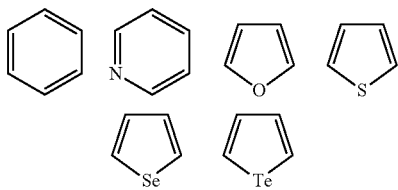

As noted in structures I, II, and III, the aromatic groups Ar¹ and Ar² may be repeated (or may not present at all). For example, each m may be an integer from 0 to 10, from 0 to 5, from 0 to 3, from 1 to 3, from 1 to 2, or 1; and each n may be an integer from 0 to 10, from 0 to 5, from 0 to 3, from 1 to 3, from 1 to 2, or 1. In certain examples, the aromatic groups Ar¹, Ar², and Ar³, in combination with benzene ring(s) within the non-fullerene acceptor may provide a coplanar ring structure having a conjugation length of seven to fifteen rings. In other terms, the overall length of the non-fullerene acceptor may be at least 20 angstroms, 25 angstroms, 30 angstroms, 35 angstroms, 40 angstroms, 50 angstroms, or between 20-50 angstroms, 25-40 angstroms, or 25-35 angstroms.

Each X substituent may individually be selected from the group consisting of: oxygen, carbon, hydrogen, sulfur, selenium, and nitrogen.

Y may include an aryl group or an aromatic hydrocarbon. For example, Y may include benzene attached to a R substituent (e.g., a hydrocarbon chain at the para position). Alternatively, Y may include a five-membered cyclic ring attached to a R substituent (e.g., a hydrocarbon chain), wherein one carbon atom of the cyclic ring has been replaced by a chalcogen such as oxygen, sulfur, selenium, or tellurium.

Each Y substituent may individually be selected from the group consisting of:

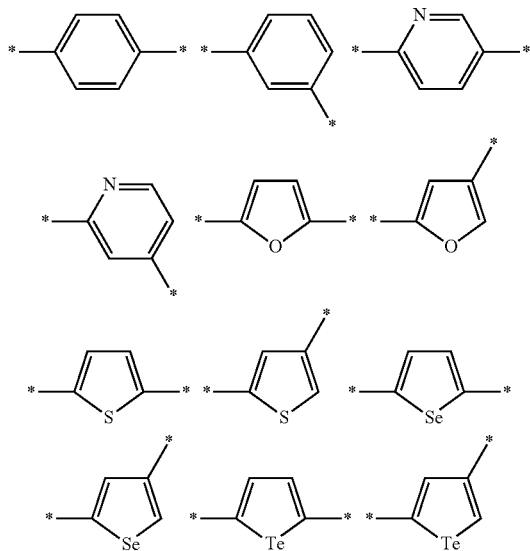

In certain examples, Y in combination with the R substituent provides a substituent selected from the group consisting of:

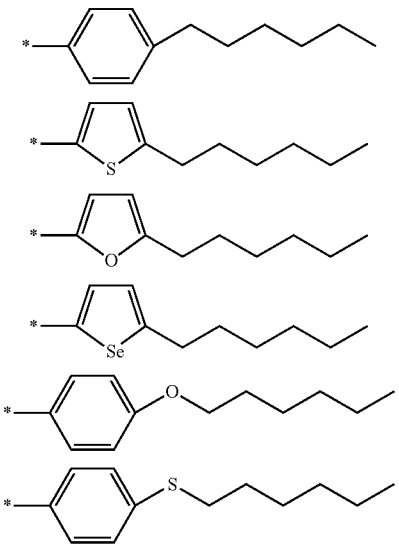

Each R substituent (attached to X or Y within the non-fullerene acceptor compounds) may individually be a linear or branched saturated or unsaturated non-aromatic hydrocarbon in the $C_1$-$C_{20}$ range. Non-limiting examples include methyl, ethyl, n-propyl, isopropyl, isobutyl, n-butyl, sec-butyl, tert-butyl, isopentyl, n-pentyl, neopentyl, n-hexyl, and 2-ethylhexyl. In one particular example, R represents 2-ethylhexyl.

In some examples, the R substituent may be a substituted hydrocarbon wherein the carbon at the 1-position is replaced with oxygen or sulfur, for example.

Alternatively, R includes an unsaturated 5- or 6-membered ring (substituted or not-substituted) (e.g., thiophene or benzene) attached to a hydrocarbon (e.g., at the para position of benzene). In some examples, R includes an aryl group or an aromatic hydrocarbon.

In certain examples, R is selected from the group consisting of:

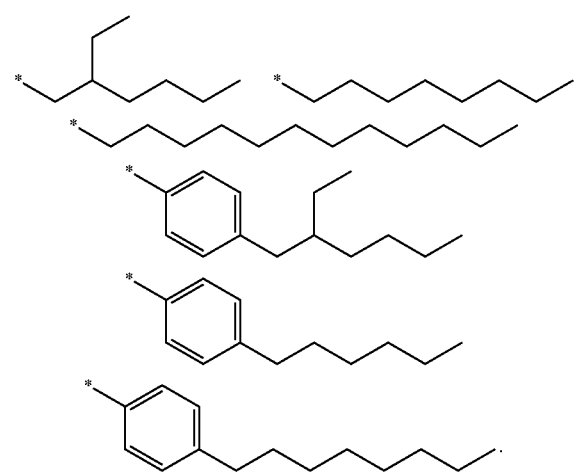

Each A or B substituent that bookends the compound may individually be selected from the group consisting of:

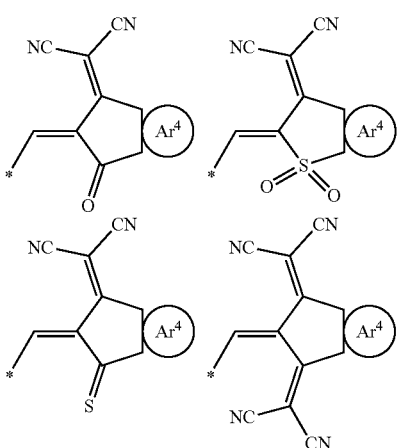

Ar⁴ within the A or B substituent is an aromatic group, which is conjugated fused to the adjacent ring. In certain examples, Ar⁴ is an aromatic group having at least one halogen (e.g., fluorine, chlorine, bromine, iodine, or astatine) substituent attached to the aromatic ring. In some examples, Ar⁴ is an aromatic group selected from the group consisting of:

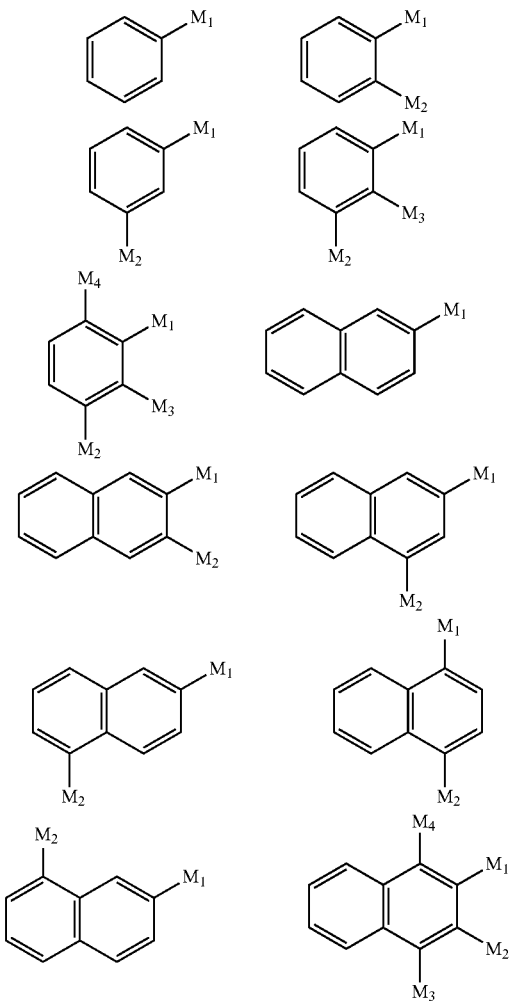

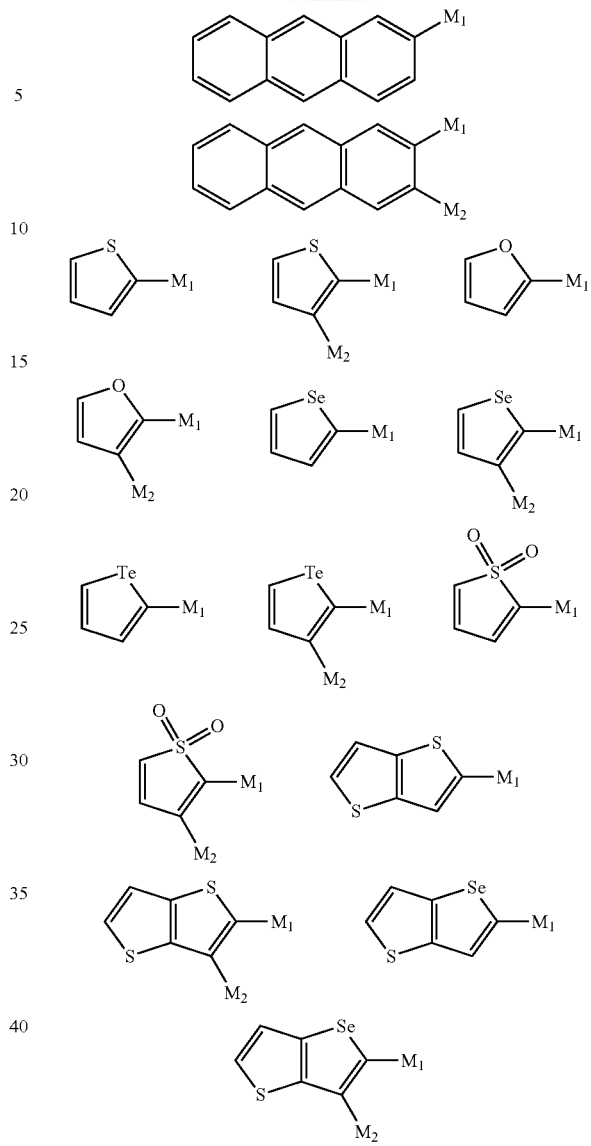

In the possible substituents for A or B, $M_1$-$M_4$ may individually be selected from the group consisting of hydrogen, fluorine, chlorine, bromine, iodine, astatine, and cyano groups. In certain examples, at least one M substituent is a halogen (e.g., fluorine, chlorine, bromine, iodine, or astatine). In other examples, each M substituent is a halogen. In certain examples, at least one M substituent is chlorine. In other examples, each M substituent is chlorine.

The electron-withdrawing halogen (e.g., Cl) atoms are advantageous as they effectively lower the energy gap by enhancing the intramolecular charge transfer and delocalization of π-electrons into the unoccupied, atomic 3d orbitals. Moreover, the intermolecular interactions of Cl—S and Cl—Cl result in ordered molecular stacks in the donor-acceptor blend films.

Non-limiting examples of the coplanar ring structures contained within the non-fullerene acceptor are provided in compounds C1-C11 below.

C1
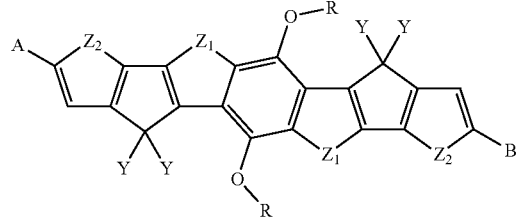
C2
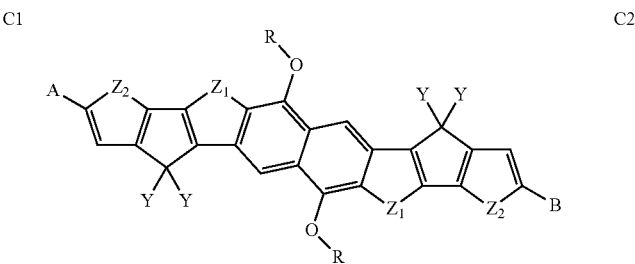
C3
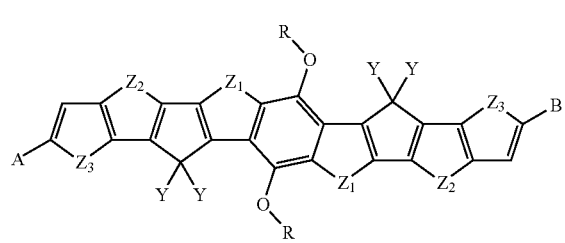
C4
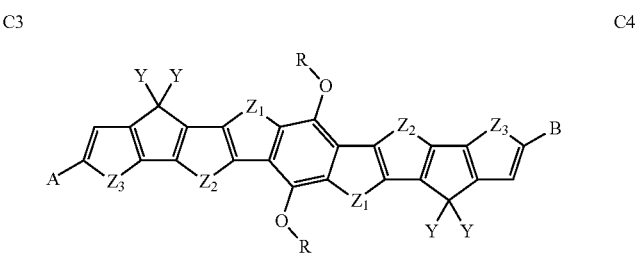
C5
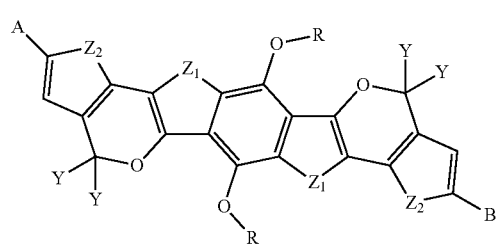
C6
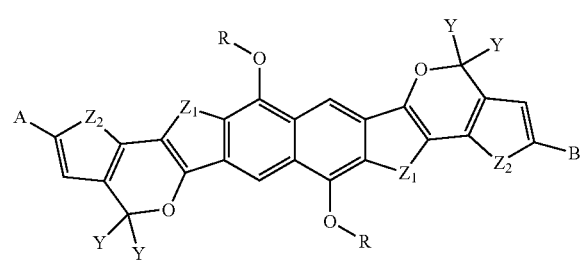
C7
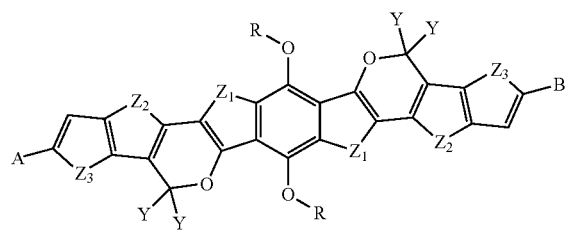
C8
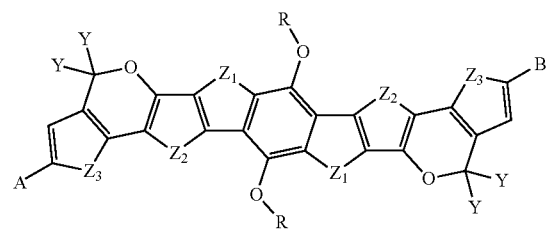
C9
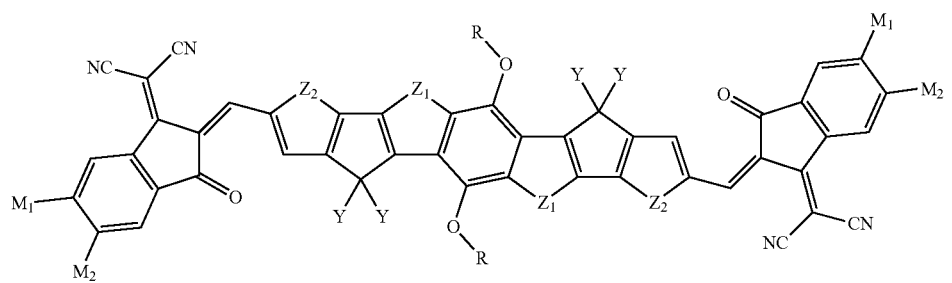

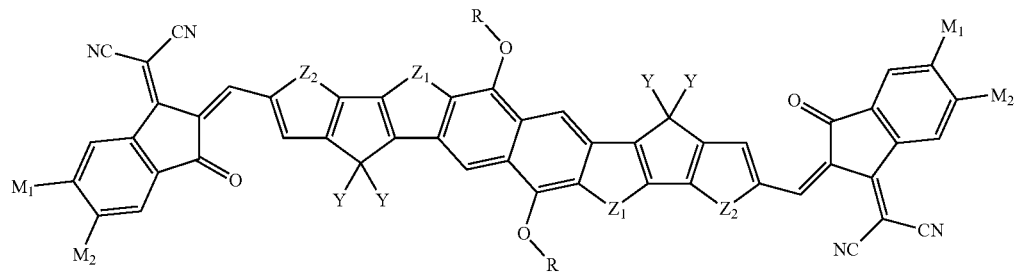

C10

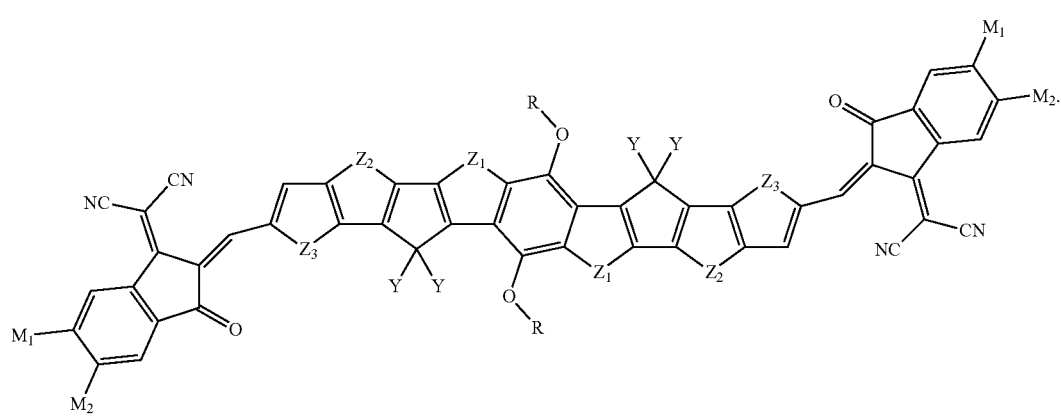

C11

$Z_1$, $Z_2$, and $Z_3$ may be individually selected from the group consisting of hydrogen and chalcogens (e.g., oxygen, sulfur, selenium, or tellurium). In certain examples, $Z_1$, $Z_2$, and $Z_3$ may be individually selected from the group consisting of oxygen, sulfur, selenium, or tellurium.

In certain examples, $Z_1$, $Z_2$, and $Z_3$ may be selected from one of the following:

| Example | $Z_1$ | $Z_2$ | $Z_3$ |
|---------|-------|-------|-------|
| 1 | S | S | S |
| 2 | S | O | S |
| 3 | S | O | O |
| 4 | O | O | O |
| 5 | O | O | S |
| 6 | O | S | S |
| 7 | Se | S | S |
| 8 | Se | Se | S |
| 9 | Se | Se | Se |
| 10 | Se | S | O |
| 11 | Se | O | O |
| 12 | Se | S | Se |

Non-limiting examples of the non-fullerene acceptor (structure I) include:

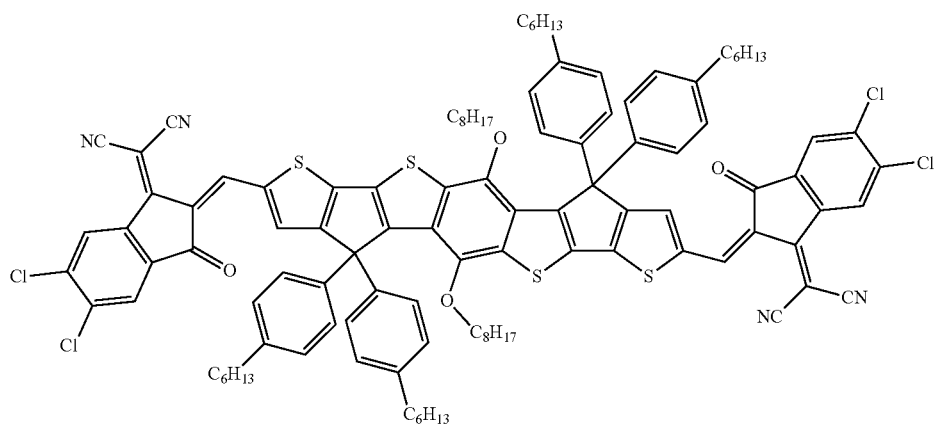

-continued
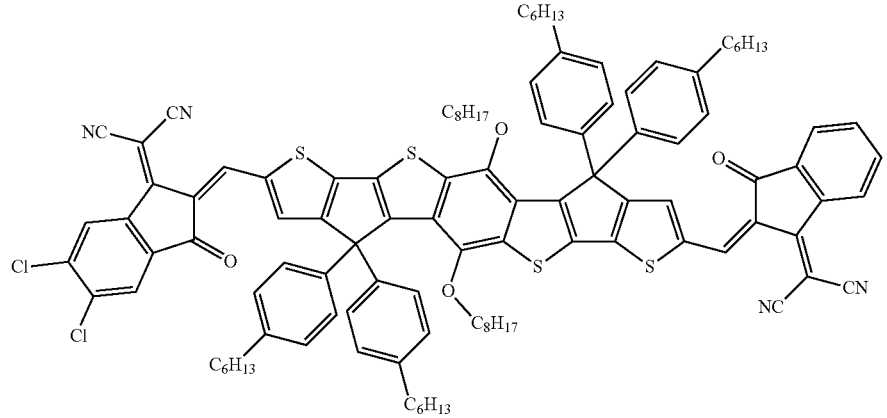
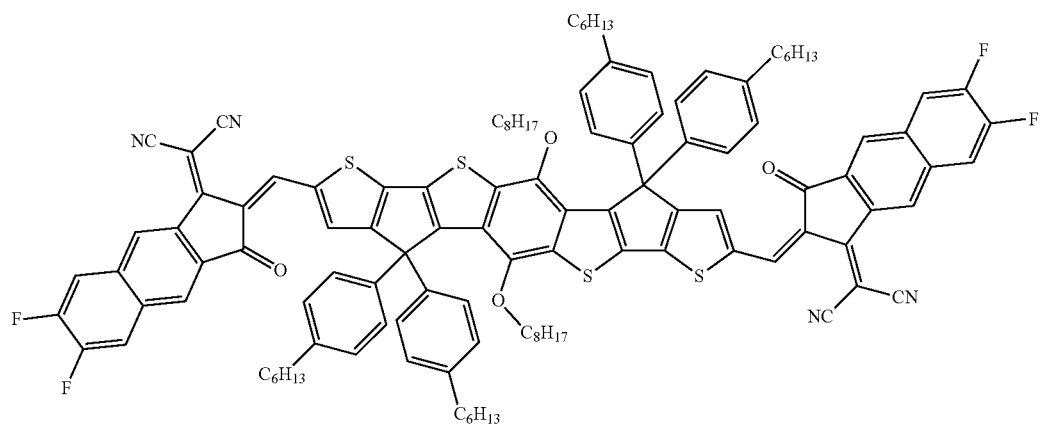
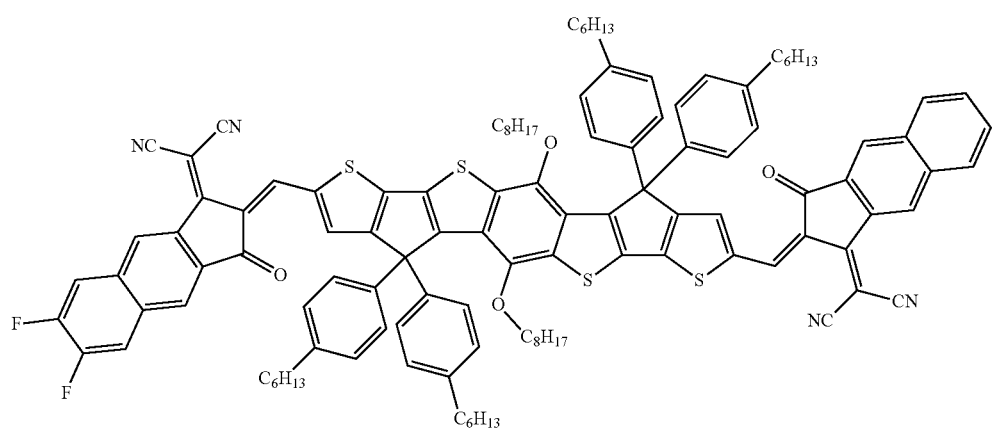
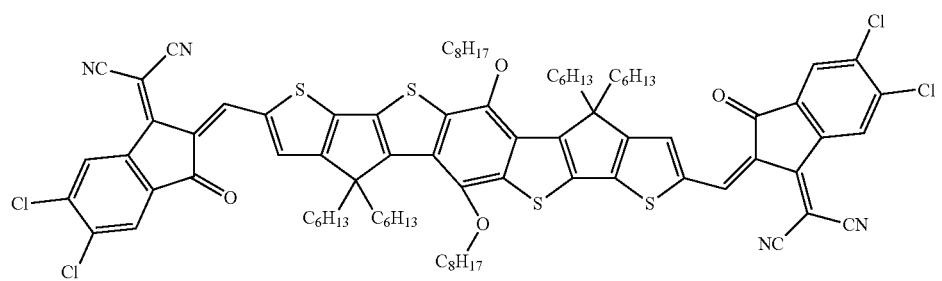

-continued
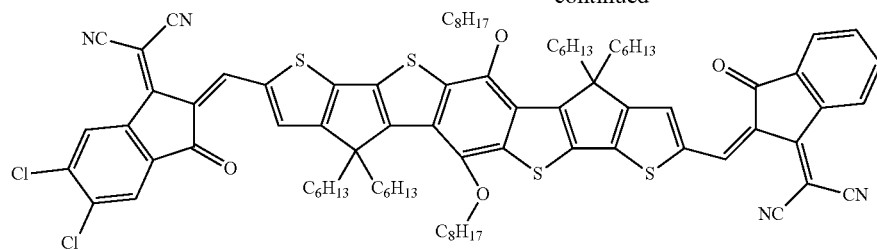
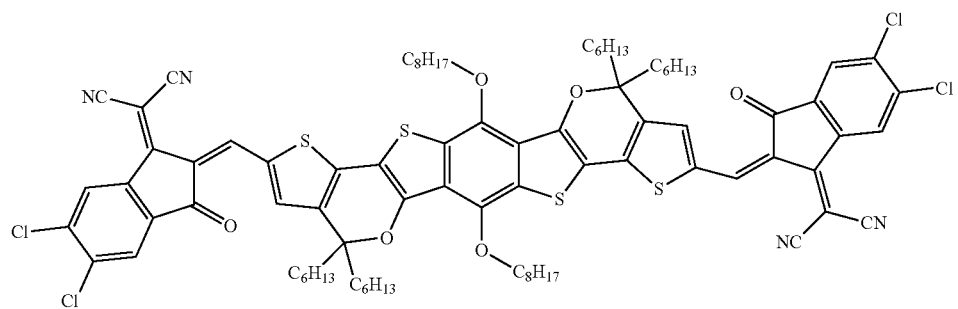
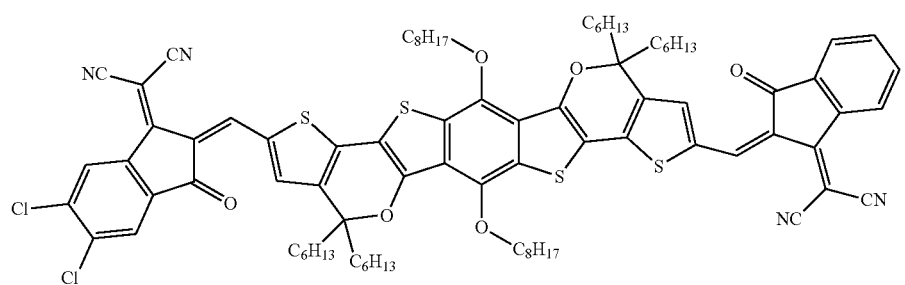
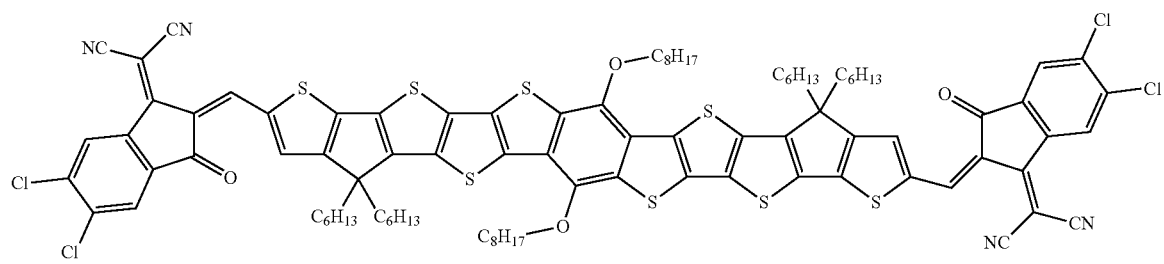
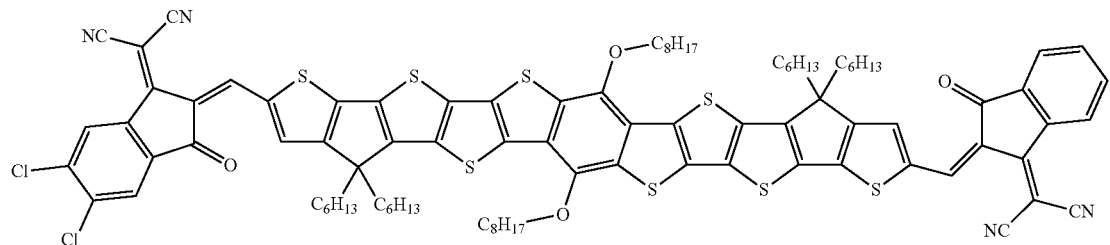
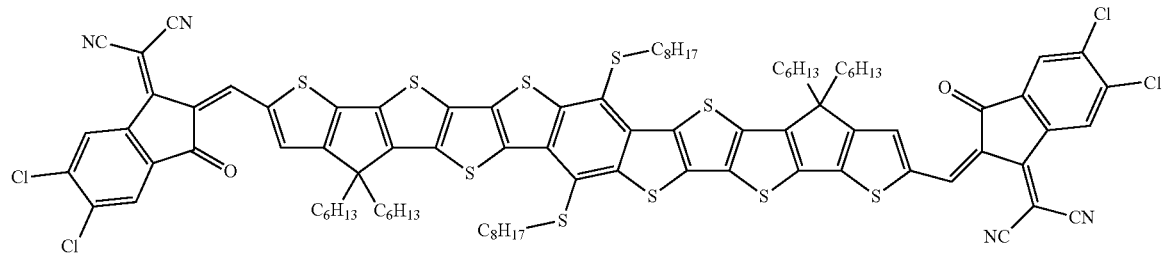

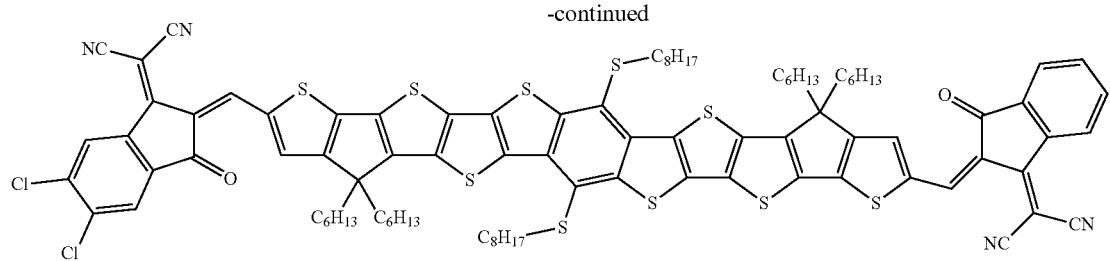
Non-limiting examples of the non-fullerene acceptor (structure II) include:
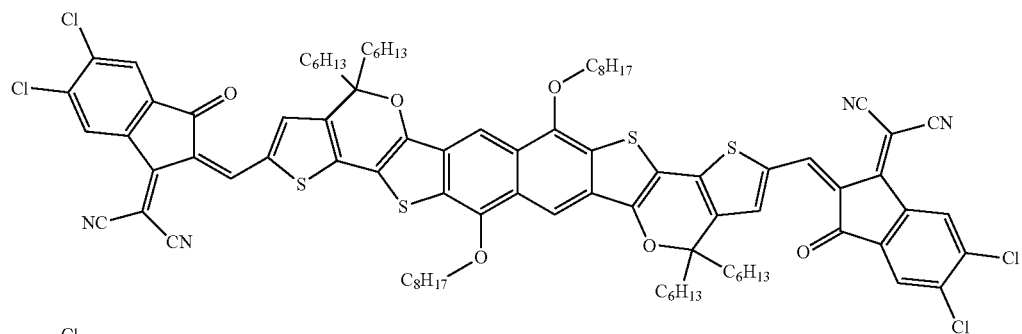
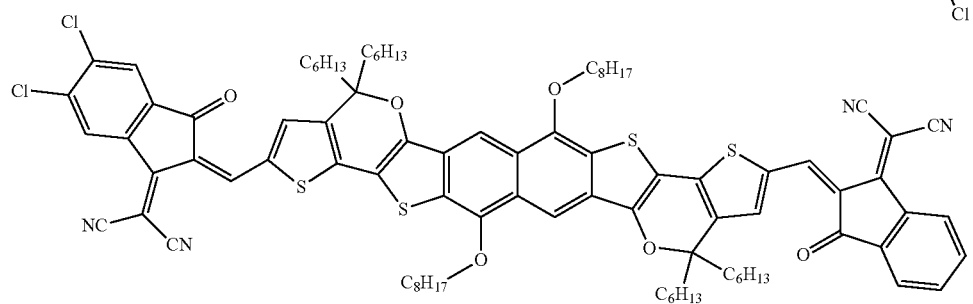
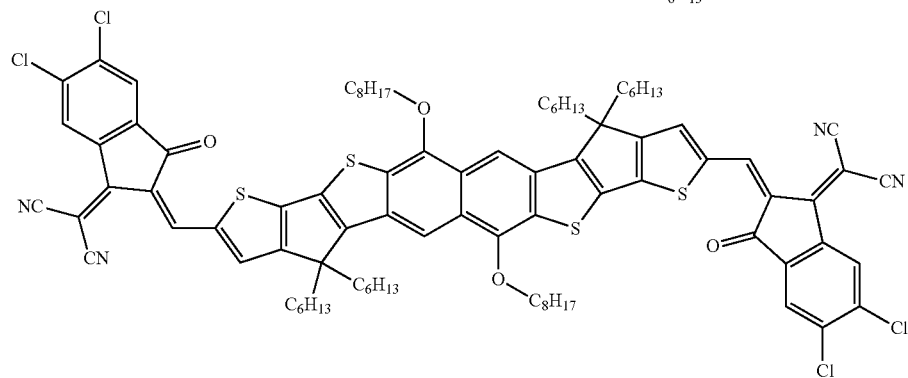
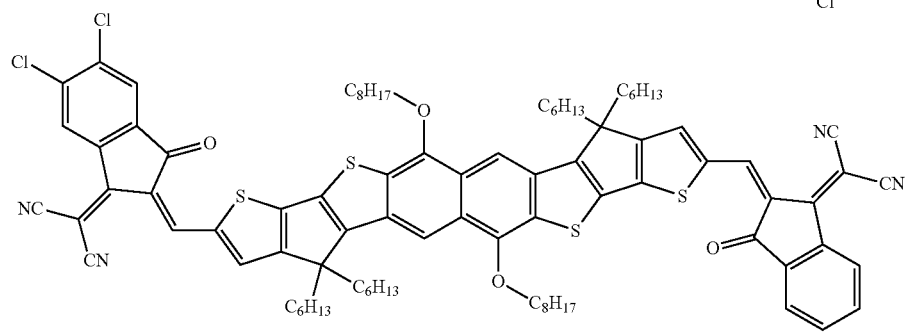

Non-limiting examples of the non-fullerene acceptor (structure III) include:

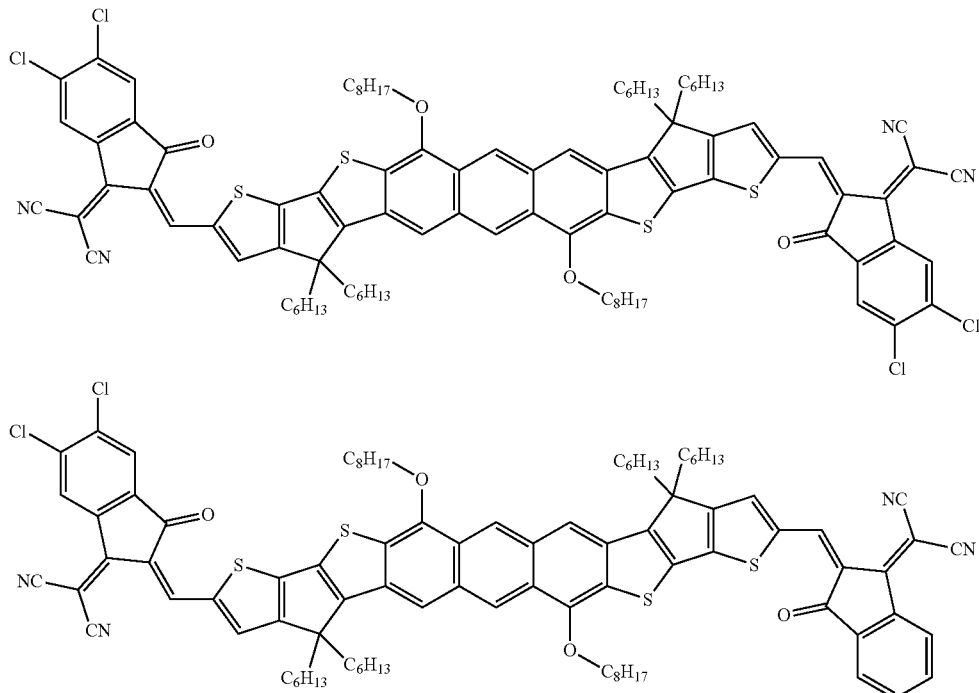

In one particular example, the non-fullerene acceptor is (4,4,10,10-tetrakis(4-hexylphenyl)-5,11-(2-ethylhexyloxy)-4,10-dihydro-dithienyl[1,2-b:4,5b']benzodi-thiophene-2,8-diyl)bis(2-(3-oxo-2,3-dihydroinden-1-ylidene) malononitrile) (herein referred to as "BT-IC"). BT-IC has planar structure with a small torsion angle <1° and consequently, a high electron mobility. However, the absorption of BT-IC does not extend to wavelengths λ>850 nm. This leaves an unused part of the solar spectrum and a potential opening for further improvement in solar cell performance.

In another example, the non-fullerene acceptor is (4,4,10,10-tetrakis(4-hexylphenyl)-5,11-(2-ethylhexyloxy)-4,10-dihydro-dithienyl[1,2-b:4,5b']benzodi-thiophene-2,8-diyl) bis (2-(3-oxo-2,3-dihydroinden-5,6-dichloro-1-ylidene) malononitrile (depicted in the structure below, herein referred to as "BT-CIC"). This structure provides a narrow absorption band confined to the near-infrared spectrum through the introduction of high electron affinity halogen atoms (e.g., chlorine atoms).

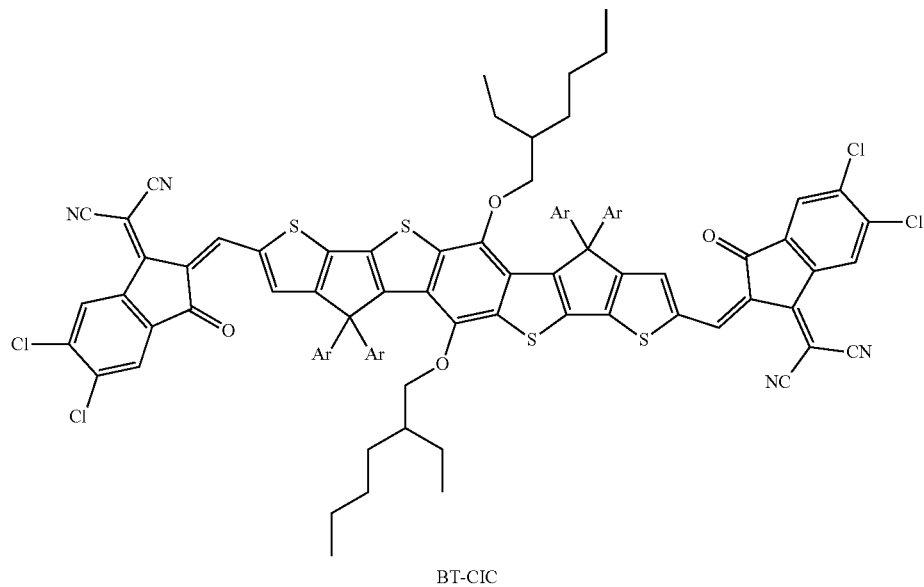

BT-CIC

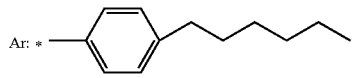

In this example, four chlorine atoms are positioned in the 5,6-positions of the 2-(3-oxo-2,3-dihydroinden-1-ylidene) malononitrile. The design is advantageous as it avoids significant issues of previously reported in chlorinated molecules with non-specific atomic site positioning (and hence property variability).

Such non-fullerene acceptor compositions disclosed herein provide certain improved characteristics over conventional acceptor compositions. For example, the NFAs disclosed herein may provide an increased electron density for the donor molecule; a reduced electron density for the acceptor molecule, and an increased conjugation length of the A-D-A molecule.

The electron-withdrawing halogen (e.g., Cl) atoms effectively lower the energy gap by enhancing the intramolecular charge transfer and delocalization of π-electrons into the unoccupied, atomic 3d orbitals. Moreover, the intermolecular interactions of Cl—S and Cl—Cl result in ordered molecular stacks in the donor-acceptor blend films.

In certain examples, the length of the non-fullerene acceptor may be at least 20 angstroms, 25 angstroms, 30 angstroms, 35 angstroms, 40 angstroms, 50 angstroms, or between 20-50 angstroms, 25-40 angstroms, or 25-35 angstroms.

Figure 17:
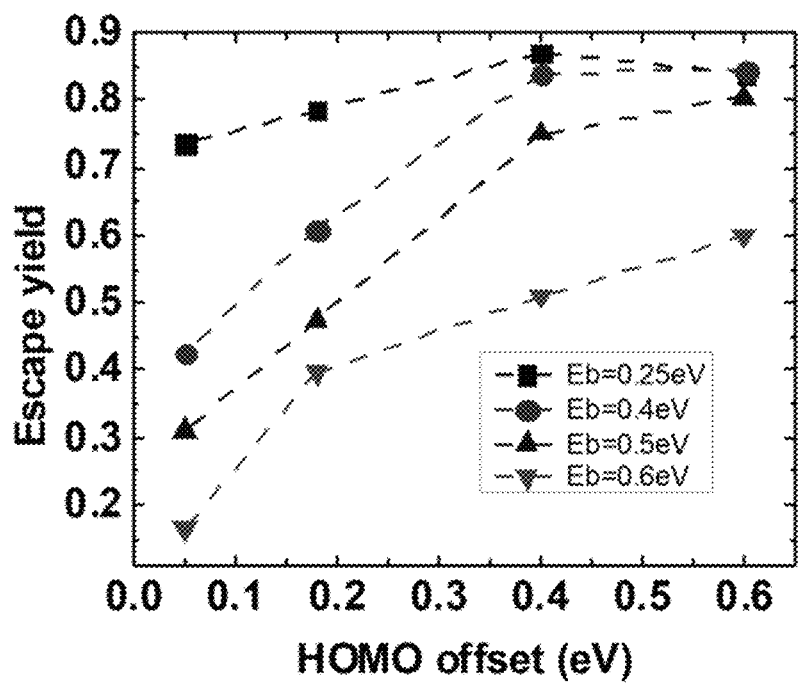
FIG. 17 depicts an example of the HOMO offset of the donor and acceptor versus the escape yield of holes.

Exciton binding energy of the non-fullerene acceptor or donor molecules within the active layer affects the energy offset needed for efficient exciton dissociation. A Monte Carlo calculation (described below) of an exciton located at the acceptor molecule near the interface that transfers the hole toward the donor molecule is depicted in FIG. 17. In this figure, the escape yield of hole increases as the HOMO offset increases. A decrease of exciton binding energy $E_b$ for the acceptor molecule leads to an increase of hole escape yield for the same HOMO offset between donor and acceptor molecules.

Figure 18:
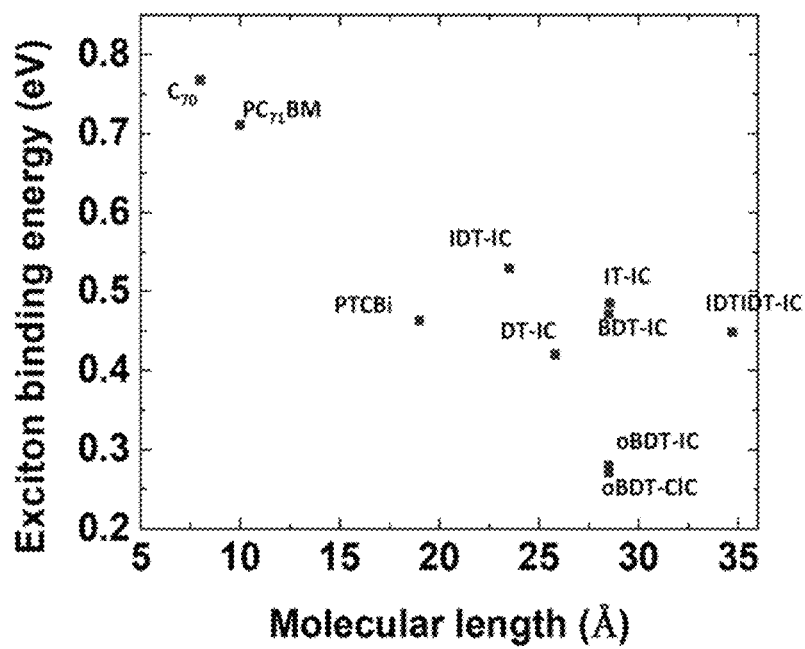
FIG. 18 depicts calculated results about the relationship between molecular length of acceptor and exciton binding energy.

By replacing conventional fullerene acceptors with the non-fullerene acceptor type molecules in the organic A-D-A heterojunction, the effective separation of electron and hole may be controlled by the molecular length and electronegativity of the electron donating or withdrawing group. The exciton binding energy of a number of molecules using the density functional theory (DFT), is depicted in FIG. 18. As defined above, the exciton binding energy refers to $E_B=(M^+ + M^-)-(M^*+M)$, where $M^+$ and $M^-$ are the total energy of a positively and negatively charged molecule, respectively; $M^*$ and M are the molecular energy at the first singlet state ($S_1$) and ground state, respectively.

FIG. 18 shows that the exciton binding energy decreases as the molecular length increases for various acceptor molecules. An increase of the extent of exciton distribution, i.e. exciton radius, over the conjugated carbon chain will increase the effective separation between electron and hole. The various acceptor molecules represented in FIG. 18 are shown below:

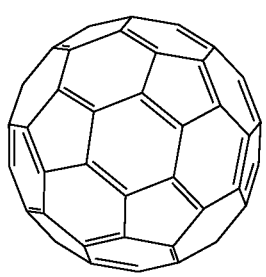

C70

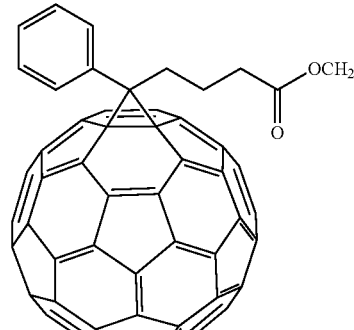

PC71BM

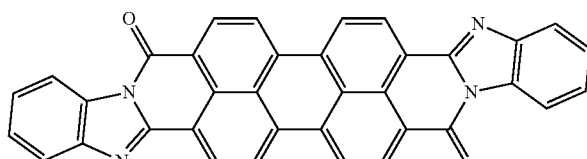

PTCBi

-continued
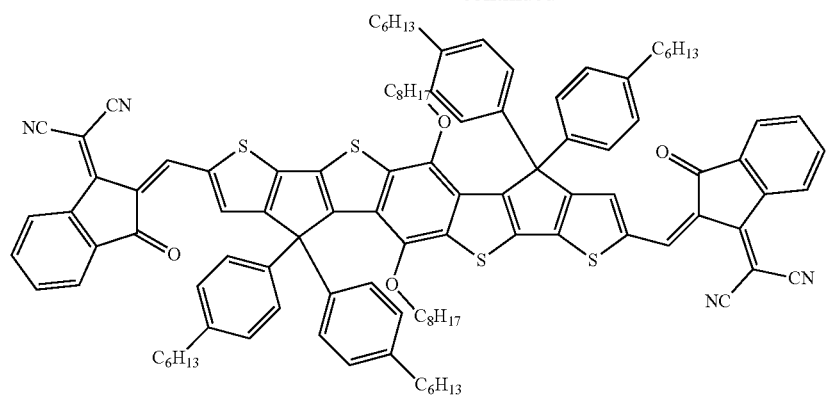
oBDT-IC
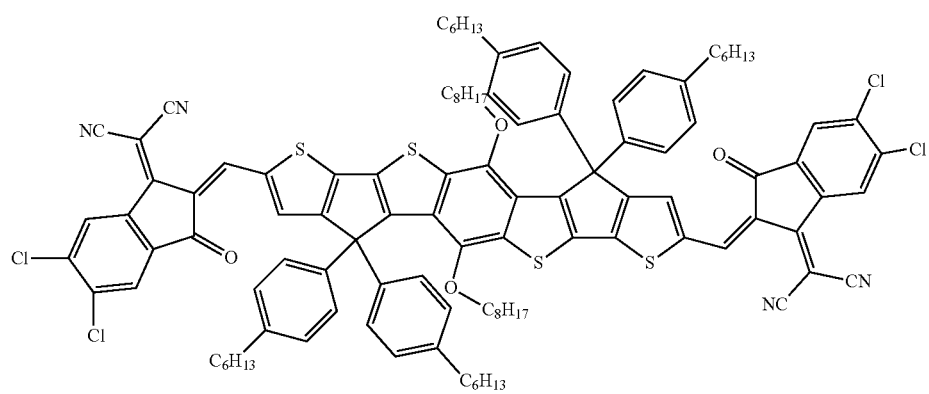
oBDT-ClC
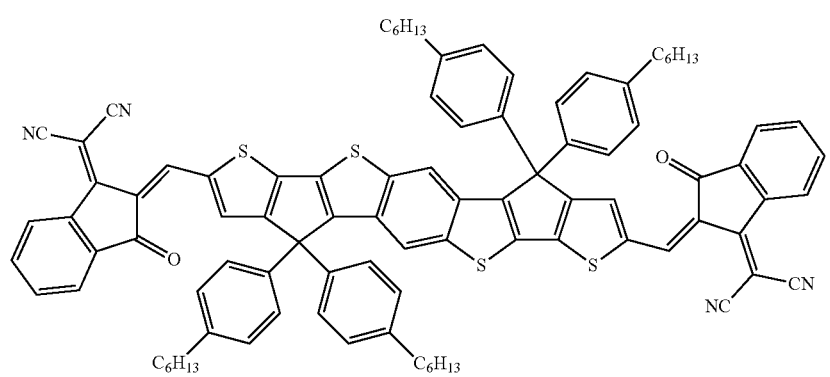
BDT-IC

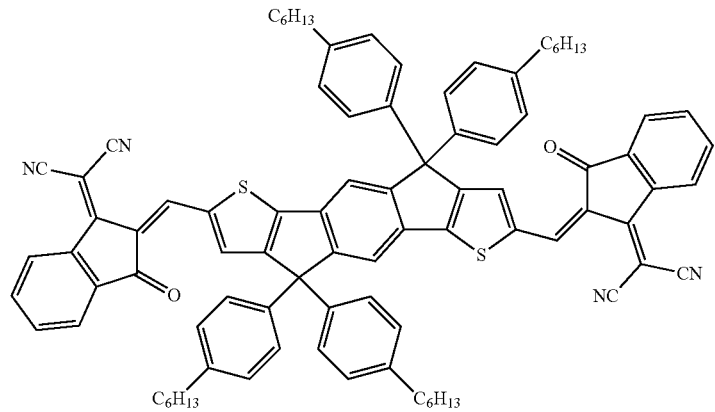
IDT-IC
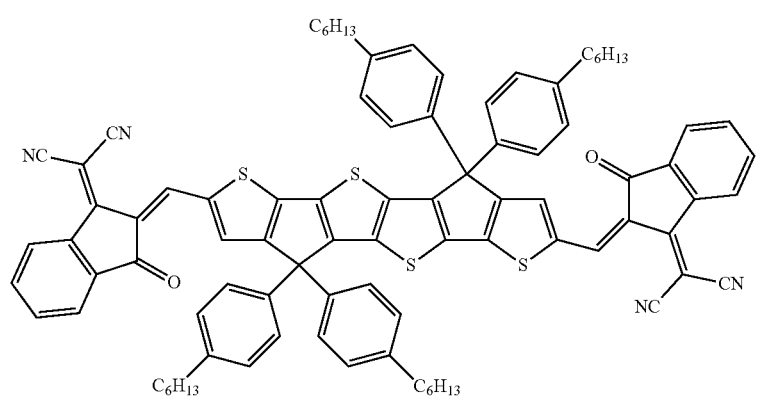
DT-IC
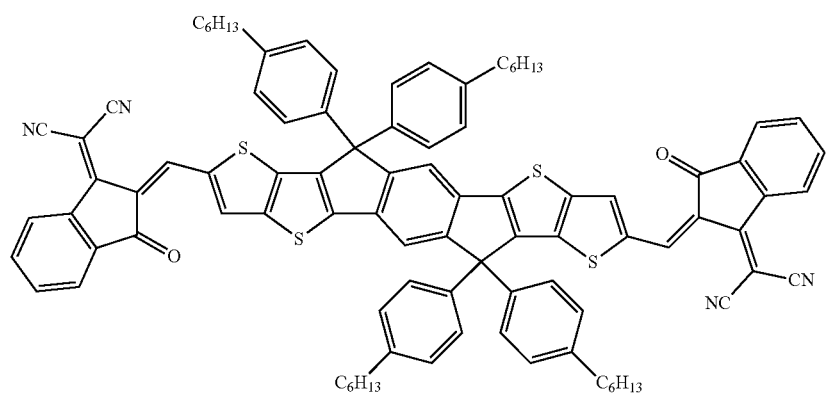
IT-IC

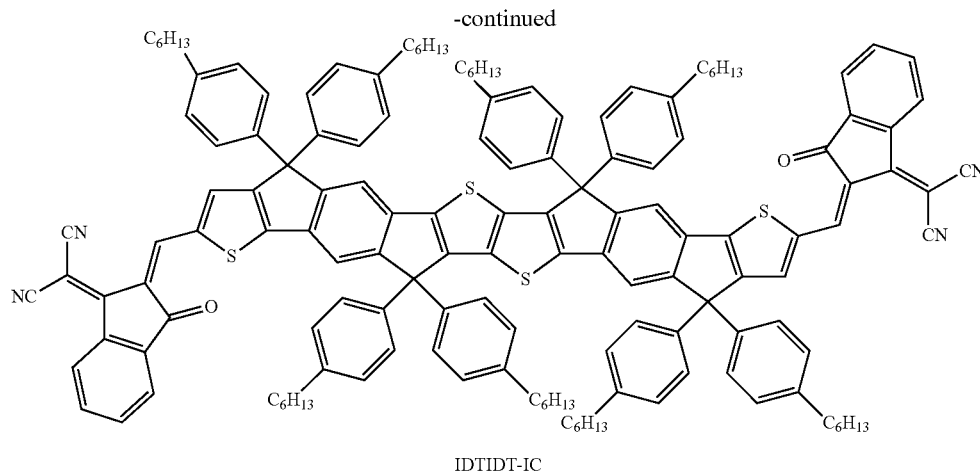

IDTIDT-IC

In the acceptor-donor-acceptor type molecules, the effective separation of electron and hole is also affected by the electronegativity of A or D components. Introducing a halogen into the electron-deficient group and/or adding an oxygen or sulfide to the electron-rich group will twist the electron/hole density distribution, and changes the effective distance of electron and hole, and therefore reduce the exciton binding energy. By attaching two oxygen atoms at the benzene unit of a non-fullerene acceptor, this increases the local hole density while decreasing the density at both side groups. No changes in the electron density overall are seen. Therefore, a lower exciton binding energy may be achieved for an oxygen-substituted molecule in comparison to a similar molecule without the oxygen substitution, although they have the similar molecular length.

In certain examples, non-fullerene acceptors (NFA) having an electron-withdrawing halogen, such as BT-CIC, may have certain improved performance properties as measured within a solar cell. For example, the solar cell with the NFAs disclosed herein may include an improved power conversion efficiency (PCE). In certain examples, the NFA may provide a solar cell with a PCE of at least 8%, at least 9%, at least 10%, at least 11%, or at least 12%. In one particular example, BT-CIC may provide a solar cell with a PCE of between 10-12% or approximately 11.2%.

NFAs as disclosed herein may have an energy gap of less than 2 eV, less than 1.5 eV, less than 1.4 eV, less than 1.3 eV, less than 1.2 eV, less than 1.1 eV, less than 1 eV, between 1-2 eV, between 1-1.5 eV, between 1.1-1.4 eV, or between 1.2-1.3 eV.

NFAs as disclosed herein may also provide a solar cell with a high open circuit voltage ($V_{oc}$). The $V_{oc}$ may be at least 0.5 V, at least 0.6 V, at least 0.7 V, at least 0.8 V, at least 0.9 V, at least 1 V, between 0.5-1 V, between 0.6-0.9 V, or between 0.7-0.8 V.

NFAs as disclosed herein may also provide a solar cell with an improved fill factor (FF). The FF may be at least 50%, at least 60%, at least 65%, at least 70%, at least 75%, at least 80%, between 50-80%, between 60-80%, between 65-75%, or approximately 70%.

NFAs as disclosed herein may also provide a solar cell with a high short circuit current ($J_{sc}$). The $J_{sc}$ may be between 10-30 mA/cm$^2$, 20-25 mA/cm$^2$, or 22-23 mA/cm$^2$.

NFAs as disclosed herein may also provide a solar cell with an improved external quantum efficiency (EQE). The EQE may at least 50%, at least 60%, at least 65%, at least 70%, at least 75%, at least 80%, at least 85%, between 65-85%, between 70-80%, or approximately 75%, as measured between wavelengths of 650-850 nm and providing a transparency window between wavelengths of 400-650 nm.

In one particular example, the BT-CIC molecule provides an energy gap of approximately 1.3 eV leading to an optical absorption edge at approximately 1000 nm. Single junction solar cells employing BT-CIC with a low energy gap polymer donor (e.g., poly[4,8-bis(5-(2-ethylhexyl)thiophen-2-yl)benzo[1,2-b:4,5-b']dithiophene-co-3-fluorothieno[3,4-b]thiophene-2-carboxylate], PCE-10) show PCE=11.2±0.4%, $V_{oc}$=0.70±0.01 V, short circuit current of $J_{sc}$=22.5±0.6 mA cm$^{-2}$, and FF=71±2% under simulated AM1.5G solar spectral illumination.

EXAMPLES

Synthesis of BC-IC and BT-CIC

Figure 2A:
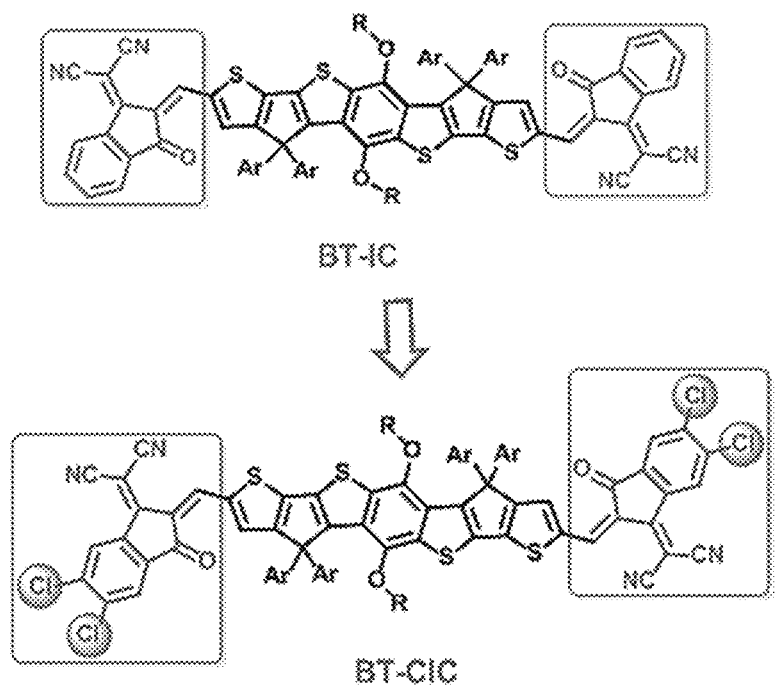
FIG. 2A depicts the molecular structural formulae of BT-IC and BT-CIC.
Figure 2B:
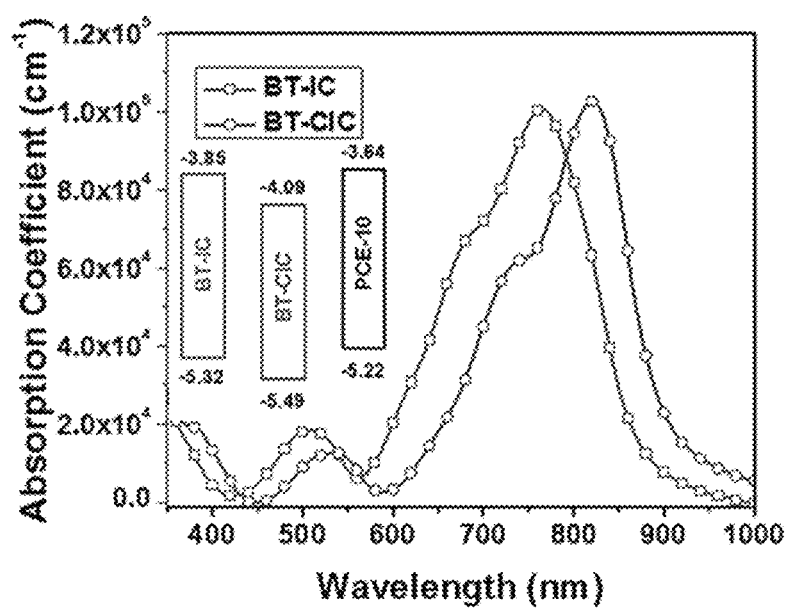
FIG. 2B depicts the UV-Vis absorption spectra of BT-IC and BT-CIC of exemplary thin films.

The molecular structural formulae of the two acceptors are shown in FIG. 2A, which were prepared by Knoevenagel condensation reactions (discussed below). Both BT-IC and BT-CIC are soluble in tetrahydrofuran (THF), dichloromethane (DCM), chloroform (CF), chlorobenzene (CB), and ortho-dichlorobenzene (o-DCB), at room temperature. Thin film UV-Vis absorption spectra of BT-IC and BT-CIC are shown in FIG. 2B. BT-CIC absorbs between λ=650 nm and 1000 nm while being transparent in the visible, with an optical bandgap of 1.33 eV as determined from the absorption onset at λ=930 nm. Importantly, BT-CIC exhibits a bathochromic shift of approximately 60 nm compared to BT-IC, which suggests increased internal charge transfer. The maximum absorption coefficient of the BT-CIC film (1.03±0.03×10$^5$ cm$^{-1}$) at λ=820 nm is similar with that of BT-IC (1.00±0.04×10$^5$ cm$^{-1}$) at the shorter wavelength of λ=765 nm.

All starting materials and reagents were purchased from commercial sources and used without further purification unless otherwise specified. Solvents were dehydrated. Syringes used to transfer reagents or solvents were purged with nitrogen prior to use. (4,4,10,10-tetrakis(4-hexylphenyl)-5,11-(2-ethylhexyloxy)-4,10-dihydro-dithienyl[1,2-b:4,5b']benzodi- thiophene-2,8-diyl)bis(formaldehyde) (BT-CHO) was synthesized according to previously reported methods. PCE-10 was purchased from 1-Material Chemscitech Inc, PC$_{71}$BM and 1,8-diiodooctane were purchased from Sigma Aldrich. The $^1$H and $^{13}$C NMR spectra were collected on a Bruker AV400 and 600 spectrometer in deuterated chloroform solution with trimethylsilane (TMS) as reference. Matrix-Assisted Laser Desorption/Ionization Time of Flight Mass Spectrometry MS-MALDI (TOF) was performed using a Bruker Autoflex II/Compass 1.0. The synthetic routes for BT-IC and BT-CIC are shown in Scheme S1. Whereas BT-CIC is obtained via Knoevenagel condensation between BT-CHO and 3-(dicyanomethylidene)-5,6-dichloro-indan-1-one resulted in BT-CIC with 85% yield. The chemical structure of BT-CIC was characterized by $^1$H NMR, $^{13}$C NMR, and MALDI-TOF MS.

tively, for BT-IC, and −5.49 (±0.02) and −4.09 (±0.02) eV, respectively, for BT-CIC. BT-CIC shows a lower HOMO-LUMO energy gap (1.40 eV) than BT-IC (1.47 eV), which is consistent with experimental result from the optical measurement. BT-CIC exhibits both lower HOMO and LUMO energies compared with BT-IC due to the electron-withdrawing ability of the Cl atoms in the former molecule. The lower $E_{LUMO}$ leads to increased chemical stability and improved electron injection efficiency as the Schottky barrier with the cathode contact is decreased.

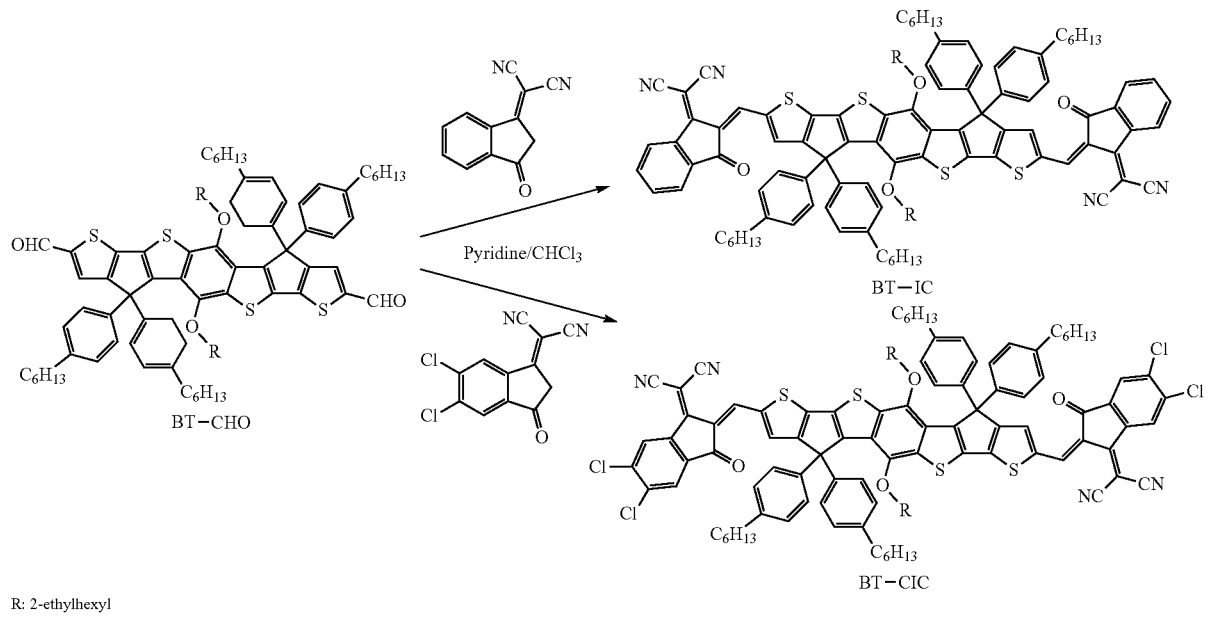

Scheme S1. The synthetic routes for BT-IC and BT-CIC.

R: 2-ethylhexyl 3-(dicyanomethylidene)-5,6-dichloro-indan-1-one (262 mg, 1.0 mmol) was added into the mixture of compound BT-CHO (400 mg, 0.3 mmol) in anhydrous chloroform with pyridine (1 mL). The reaction was deoxygenated with nitrogen for 30 min and then refluxed for 10 h. After cooling to room temperature, the solution was poured into methanol and the precipitate was filtered off. Then it was extracted with DCM and washed with water. The crude product was purified by silica gel column using a mixture of hexane/DCM (3:2) as the eluent to give a purple solid (378 mg, 85%).

$^1$H NMR (600 MHz, CDCl$_3$, δ): 8.80 (s, 2H), 8.74 (s, 2H), 7.90 (s, 2H), 7.50 (s, 2H), 7.30 (d, J=6.0 Hz, 8H), 7.08 (d, J=6.0 Hz, 8H), 7.08 (m, 8H), 3.50 (m, 4H), 2.56 (t, J=6.0 Hz, 8H), 1.59-1.54 (m, 8H), 1.35-1.29 (m, 42H), 0.96 (t, J=6.0 Hz, 6H), 0.86 (m, 18H).

$^{13}$C NMR (125 MHz, CDCl$_3$, δ): 186.2, 164.9, 158.1, 158.0, 155.3, 146.4, 142.3, 142.2, 140.9, 139.5, 139.2, 139.0, 138.8, 138.6, 136.0, 135.9, 135.6, 128.4, 128.3, 126.9, 125.0, 120.4, 114.4, 68.9, 63.9, 39.3, 35.5, 31.7, 31.2, 29.5, 29.2, 28.7, 23.3, 22.7, 22.6, 14.2, 14.1, 10.8. MS (MALDI) m/z: M$^+$, 1822.877.

Performance Characteristics of BT-IC and BT-CIC

Figure 3:
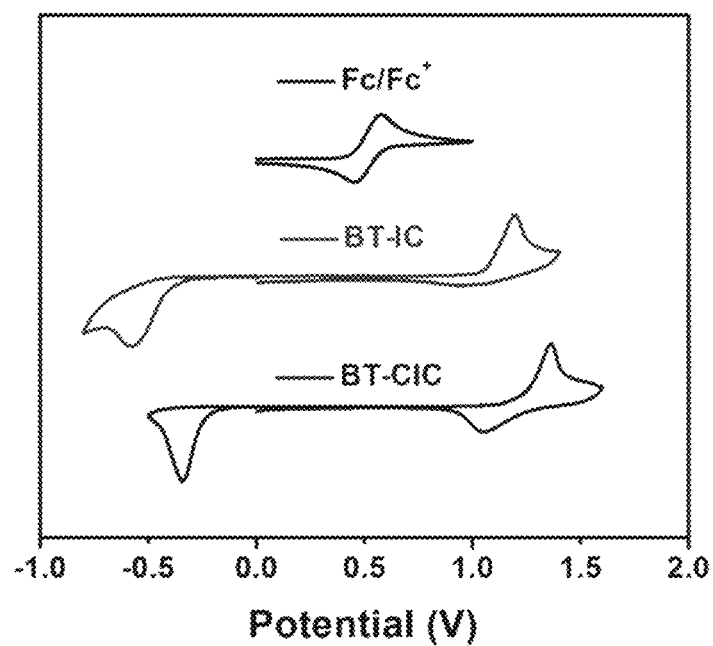
FIG. 3 depicts an example of cyclic voltammetry curves of ferrocenium/ferrocene (Fc/Fc$^+$) couple, BT-IC and BT-CIC in $CH_3CN/0.1$ M $[nBu_4N]^+[PF_6]^-$ at 100 mV s$^{-1}$ the horizontal voltage scale refers to the Ag/AgCl electrode, wherein the positive curves from 0 to 1.6 V is oxidation and the negative curves from 0 to −0.8 V is reduction.

Cyclic voltammetry in FIG. 3 in SI was used to obtain the highest occupied (HOMO) and the lowest unoccupied molecular orbital (LUMO) energies ($E_{HOMO}$ and $E_{LUMO}$, respectively) of −5.32 (±0.03) and −3.85 (±0.02) eV, respec- Density functional theory (DFT) at the B3LYP/6-31G(d) level was used to investigate the geometric and electronic properties of BT-IC and BT-CIC. Both molecules have a planar structure with a torsion angle <1°, which differs from previously reported small energy gap non-fullerene acceptors with twisted backbones. The planar geometry facilitates π-electron delocalization and enhances both the charge mobility and FF. This also implies that Cl-containing BT-CIC presents a little steric hindrance originating from the large size of Cl atoms in contrast with the H-containing molecule BT-IC. Moreover, the larger electron densities on the S atoms in BT-IC and BT-CIC compared to the indaceno[1,2-b:5,6-b']dithieno[3,2-b]thiophene based molecules result in substantial overlap between neighboring molecules in the solid state, giving rise to increased crystalline order.

Figures 4A, 4B:
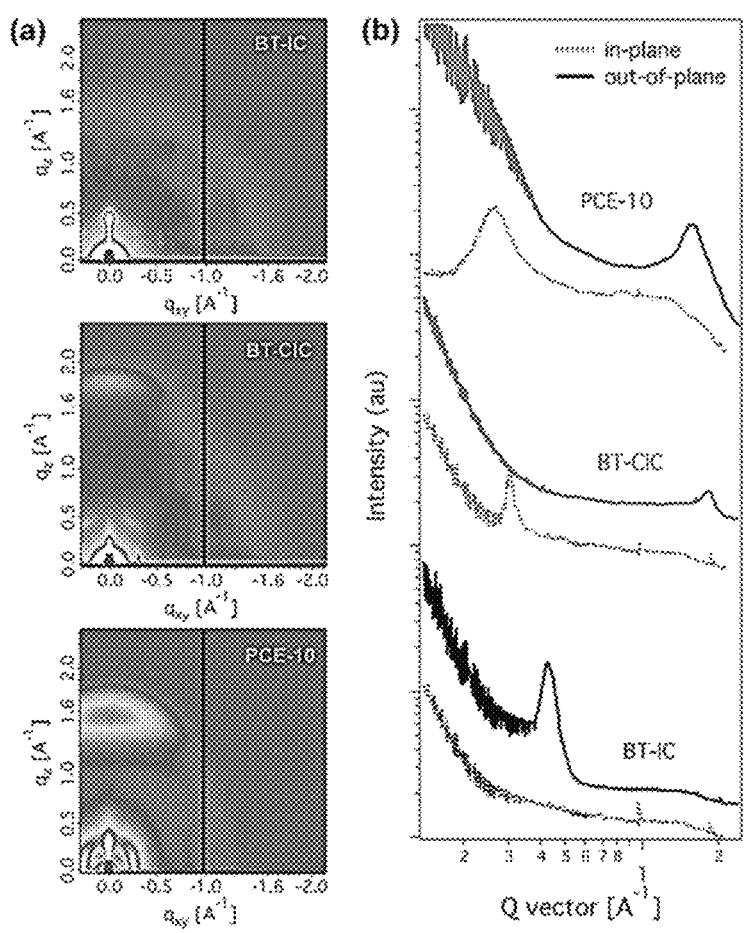
FIGS. 4A and 4B depict an example of grazing incidence x-ray diffraction (GIXD) patterns of (a) BT-IC, BT-CIC and PCE-10; (b) In-plane (dotted line) and out-of-plane (solid line) x-ray scattering patterns extracted from the 2D GIXD images. Here, Q is the scattering vector, $q_{xy}$ is the in-plane direction and $q_z$ is the out-of-plane direction.
Figures 5A, 5B:
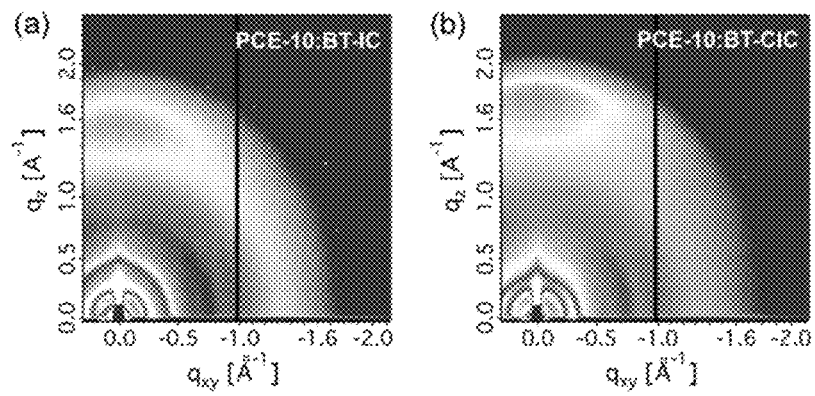
FIGS. 5A and 5B depict an example of grazing incidence x-ray diffraction (GIXD) patterns of (a) PCE-10:BT-IC blend and (b) PCE-10:BT-CIC blend. Here, $q_{xy}$ is the in-plane direction and $q_z$ is the out-of-plane direction.

To better understand charge transport properties of the films, the morphologies of both the neat films (see in FIGS. 4A and 4B) and blends were characterized by glancing incidence x-ray diffraction. The (100) diffraction peak of PCE-10:BT-IC in FIGS. 5A and 5B, and FIG. 6A at 0.28 Å$^{-1}$ with a crystal correlation length of ζ=7.7±0.2 nm is due to PCE-10, which is partially merged with the BT-IC (100) diffraction peak at 0.38 Å$^{-1}$ with ζ=4.2±0.1 nm. The (010) diffraction peak of PCE-10:BT-IC blend, particularly in the out-of-plane direction, is dominated by the contribution from PCE-10 since the (010) peak is located at 1.6 Å$^{-1}$. In this case, PCE-10 guides the blend morphology. In contrast, the PCE-10:BT-CIC blend shows a (010) peak in the out-of-plane direction at ~1.8 Å$^{1}$, characteristic of BT-CIC. Chlorination also causes a significant increase in (100) intensity, a larger aggregate size of $\zeta$=17.9±0.4 nm, and a smaller (100) spacing than for the PCE-10:BT-IC blend.

Figures 6A, 6B:
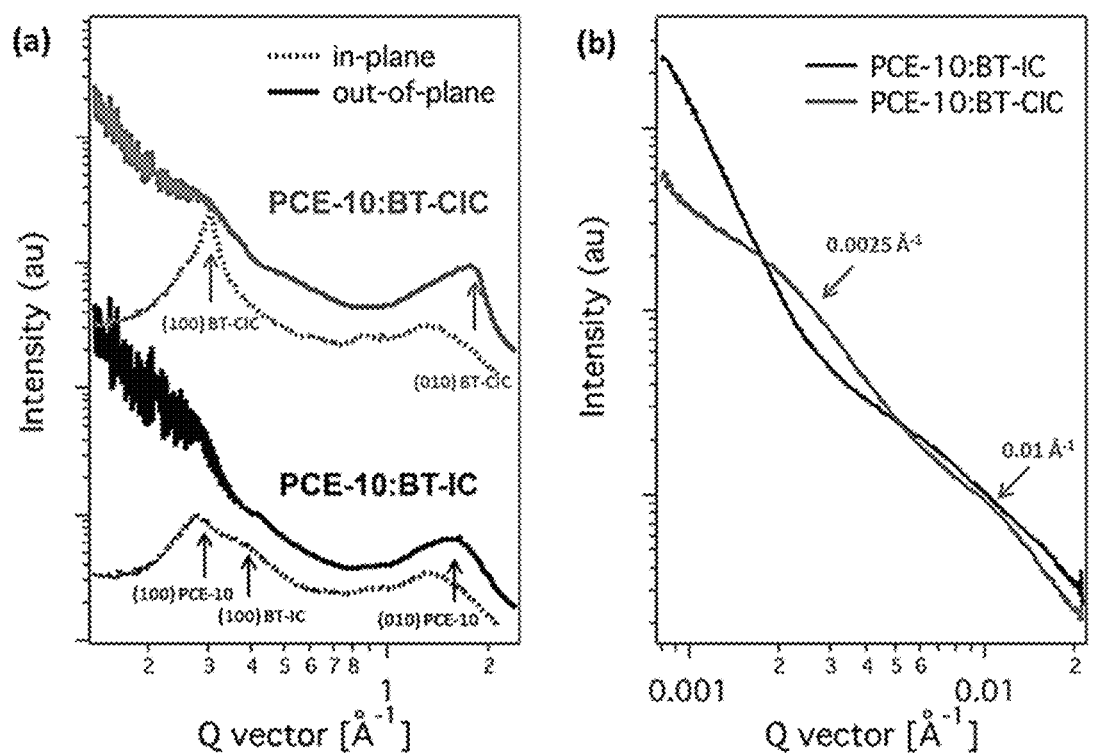
FIG. 6A depicts an example of in-plane (dotted line) and out-of-plane (solid line) x-ray scattering patterns extracted from 2D grazing incidence x-ray diffraction (GIXD) images of PCE-10:BT-IC and PCE-10:BT-CIC blends. Here, Q is the scattering vector.
FIG. 6B depicts an example of resonant soft x-ray diffraction of PCE-10:BT-IC and PCE-10:BT-CIC blends. Here, Q is the scattering vector.
Figure 7:
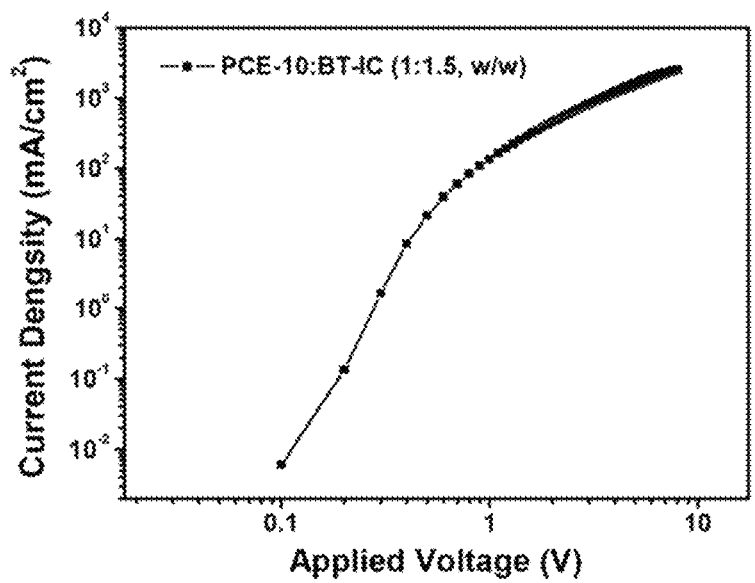
FIG. 7 depicts an example of current-density-voltage (J-V) plots for hole-only devices based on PCE-10:BT-IC (1:1.5, w/w) blended film.
Figure 8:
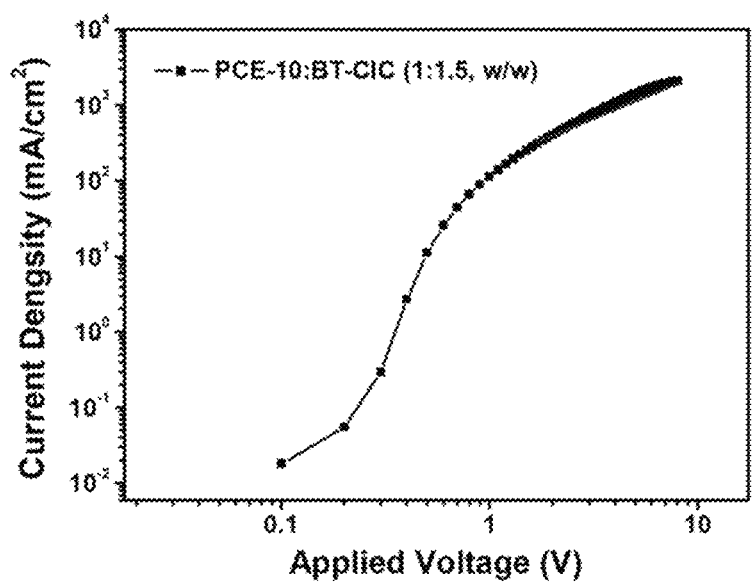
FIG. 8 depicts an example of current-density-voltage (J-V) plots for hole-only devices based on PCE-10:BT-CIC (1:1.5, w/w) blended film.
Figure 9:
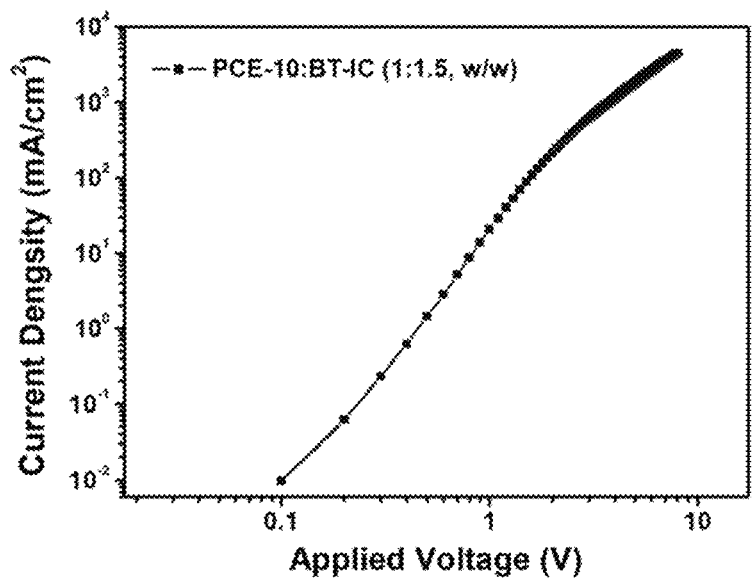
FIG. 9 depicts an example of current-density-voltage (J-V) plots for electron-only devices based on PCE-10:BT-IC (1:1.5, w/w) blended film.
Figure 10:
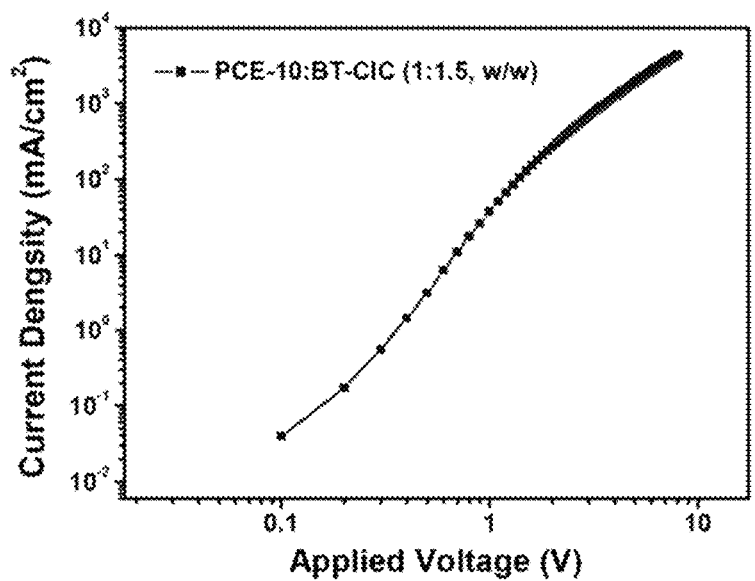
FIG. 10 depicts an example of current-density-voltage (J-V) plots for electron-only devices based on PCE-10:BT-CIC (1:1.5, w/w) blended film.

Phase separation of the blends was studied by resonant soft x-ray diffraction with scattering profiles shown in FIG. 6B. The PCE-10:BT-IC blend shows a single diffuse peak over a scattering parameter range of Q=0.004 Å$^{-1}$ to 0.02 Å$^{1}$, suggesting structure at a dimension of hundreds of nanometers. In contrast, a multi-length-scale morphology was observed in the PCE-10:BT-CIC blend, with one peak at Q=0.01 Å$^{-1}$ (corresponding to a distance of 63 nm) and another at 0.0025 Å$^{-1}$ (250 nm). The smaller length scale results from PCE-10 and/or BT-CIC nanocrystalline aggregates, whereas the larger arises from PCE-10- and BT-CIC-rich domains that comprise aggregates embedded in an amorphous matrix. Atomic force microscopy (AFM) images of two blends were compared, e.g., PCE-10:BT-CIC blend with a root-mean-square roughness of 0.97 nm was compared with 3.20 nm for the PCE-10:BT-IC blend.

The charge generation process begins with exciton migration to a donor-acceptor heterojunction. The order and close π-stacking in the PCE-10:BT-CIC blend which is driven by the chloride functional groups results in nanocrystallites of several tens to hundreds of nanometers. This, in turn increases the diffusion length of the excitons while also decreasing the resistance to the conduction of liberated charges to their corresponding electrodes. For example, hole and electron mobilities of 6.5±0.2×10$^{-4}$ cm$^{2}$ V$^{-1}$ s$^{-1}$ and 2.1±0.1×10$^{-1}$ cm$^{2}$ respectively, were found for the PCE-10:BT-CIC blend based on analysis of space charge limited current of the thin films (see FIGS. 7-10). This is compared to 5.1±0.3×10$^{-4}$ cm$^{2}$ V$^{-1}$ s$^{-1}$ and 1.2±0.1×10$^{-4}$ cm$^{2}$ V$^{-1}$ s$^{-1}$ for the PCE-10:BT-IC blend. The high electron mobilities result in efficient charge extraction from donor-acceptor junctions. The details of these measurements are found in Methods (SI).

Figure 11A:
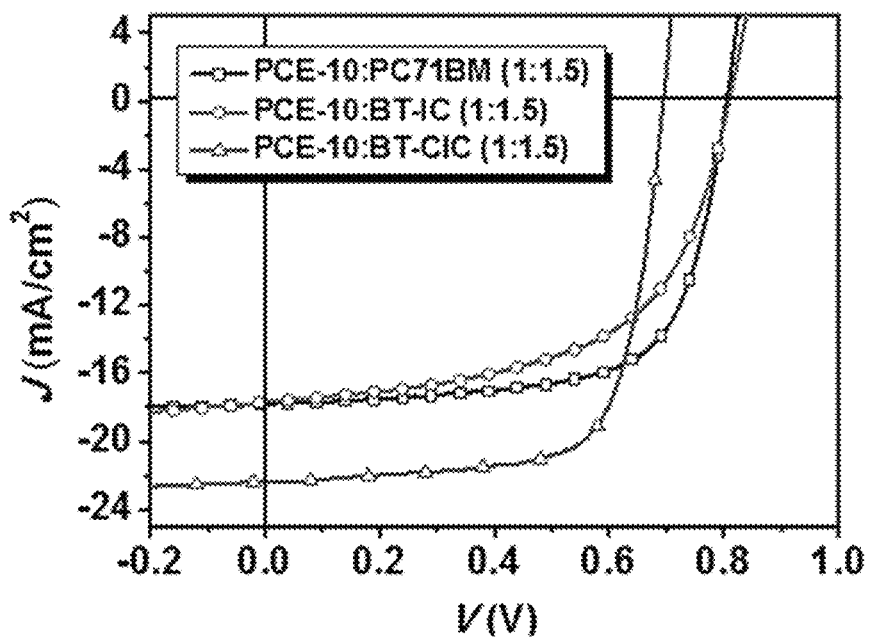
FIG. 11A depicts an example of current-density-voltage characteristics of organic photovoltaic cells based on PCE-10:$PC_{71}BM$ (1:1.5, w/w), PCE-10:BT-IC (1:1.5, w/w) and PCE-10:BT-CIC (1:1.5, w/w).

Based on these morphological results, we can understand the performance of OPVs based on BT-IC and BT-CIC. The OPVs had device structures of: indium tin oxide (ITO)/ZnO (25 nm)/PCE-10 mixed with BT-IC or BT-CIC (130 nm)/MoO$_3$ (15 nm)/Ag (100 nm). The details of fabrication are found in Methods (SI). The current-density-voltage (J–V) characteristics are plotted in FIG. 11A, with the detailed device parameters summarized in Table 1. For comparison, we fabricated OPVs with analogous structures based on PCE-10:PC$_{71}$BM. The optimized devices for PCE-10:BT-IC or BT-CIC were spin-coated from 9:1 chlorobenzene:chloroform solution mixed with a 1:1.5 donor:acceptor (D:A) weight ratio. The highest PCE=11.2±0.4% was achieved in the BT-CIC based device, with V$_{oc}$=0.70±0.01 V, J$_{sc}$=22.5±0.6 mA cm$^{-2}$, and FF=0.71±0.02 under a simulated AM1.5G, one sun intensity solar spectrum. In contrast, the BT-IC-based OPV exhibited PCE=8.3±0.2% with V$_{oc}$=0.81±0.01 V, J$_{sc}$=17.5±0.4 mA cm$^{-2}$ and FF=0.60±0.02. For the PCE-10:PC$_{71}$BM device, PCE=9.6±0.3% with V$_{oc}$=0.80±0.01 V, J$_{sc}$=17.9±0.4 mA cm$^{-2}$, and FF=0.69±0.01.

TABLE 1

Operating characteristics of OPVs under simulated of AM 1.5 G, 100 mW cm$^{-2}$, illumination.

| Acceptor[a] | J$_{sc}$[b] [mA/cm$^2$] | V$_{oc}$ [V] | FF [%] | PCE[c] [%] |
|---|---|---|---|---|
| PC$_{71}$BM | 17.9 ± 0.4 (17.5) | 0.80 ± 0.01 | 69.3 ± 1.3 | 9.6 ± 0.3 |
| BT-IC | 17.5 ± 0.4 (16.7) | 0.81 ± 0.01 | 59.6 ± 1.5 | 8.3 ± 0.2 |
| BT-CIC | 22.5 ± 0.6 (21.3) | 0.70 ± 0.01 | 71.0 ± 1.9 | 11.2 ± 0.4 |

[a]All blends are donor:acceptor 1:1.5. The donor is PCE-10.
[b]The values in parentheses are calculated from the integral of the EQE spectrum.
[c]The average value is based on measurement of 20 devices.

Figure 11B:
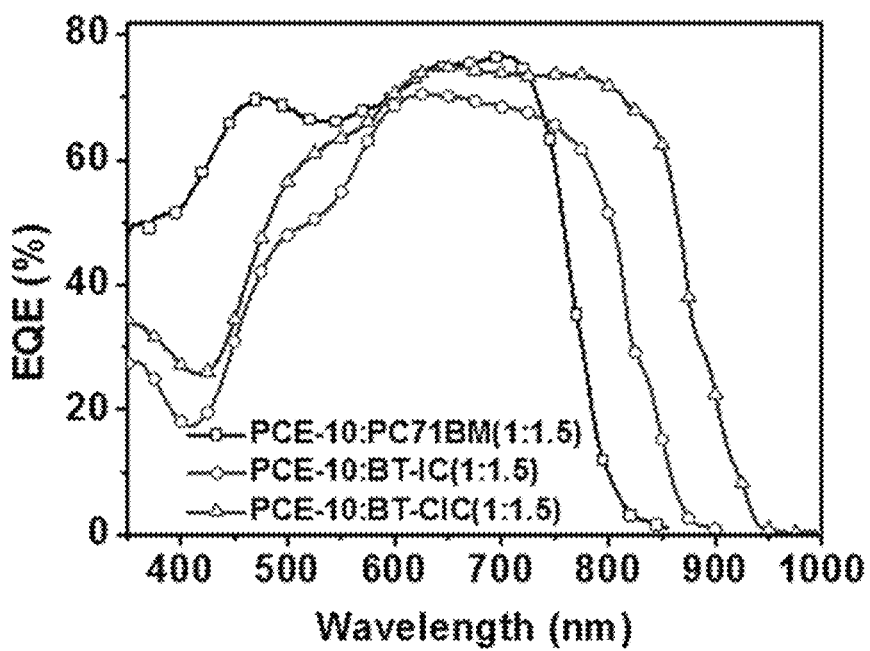
FIG. 11B depicts an example of external quantum efficiency (EQE) spectra of organic photovoltaic cells based on PCE-10:$PC_{71}BM$ (1:1.5, w/w), PCE-10:BT-IC (1:1.5, w/w) and PCE-10:BT-CIC (1:1.5, w/w).
Figure 12A:
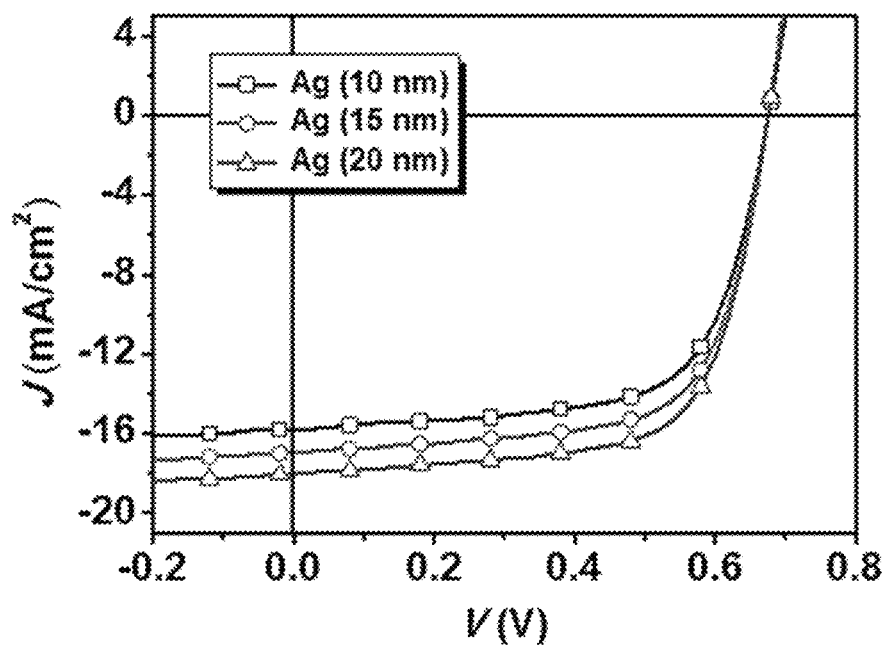
FIG. 12A depicts an example of current density-voltage characteristics of semi-transparent OPVs (STOPVs) based on PCE-10:BT-CIC (1:1.5, w/w) with different Ag cathode thicknesses.
Figure 12B:
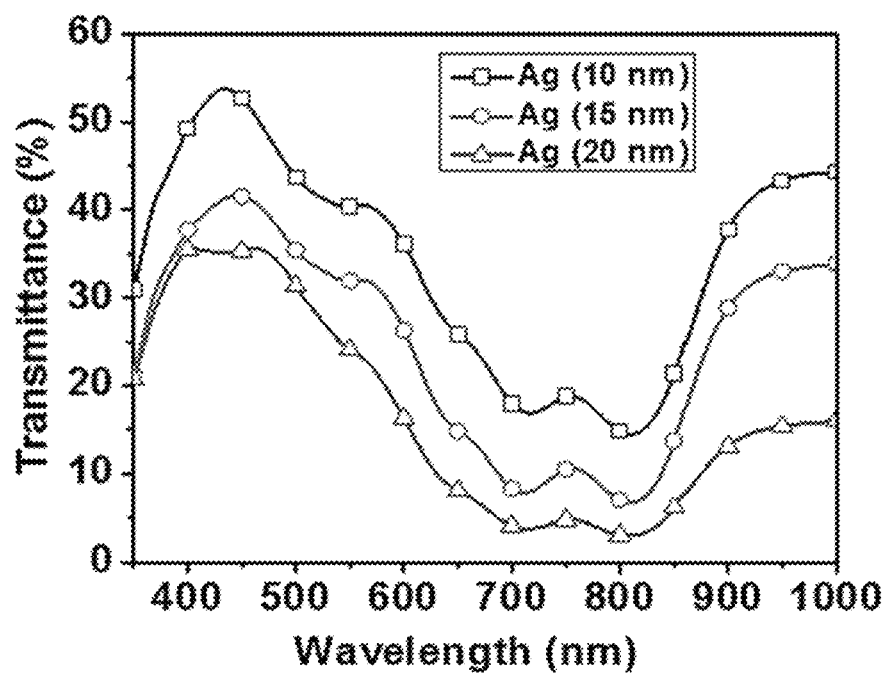
FIG. 12B depicts an example of transmission spectra of the corresponding STOPVs with different Ag thicknesses.
Figure 13:
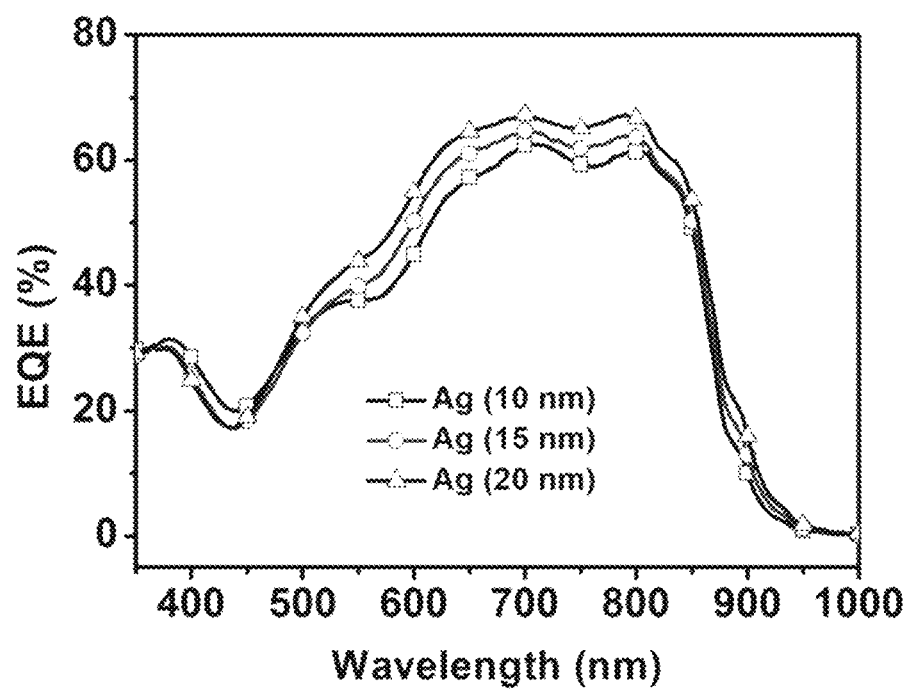
FIG. 13 depicts an example of an external quantum efficiency (EQE) spectra of the semi-transparent cells based PCE-10:BT-CIC (1:1.5, w/w) with different thicknesses of Ag.
Figure 14A:
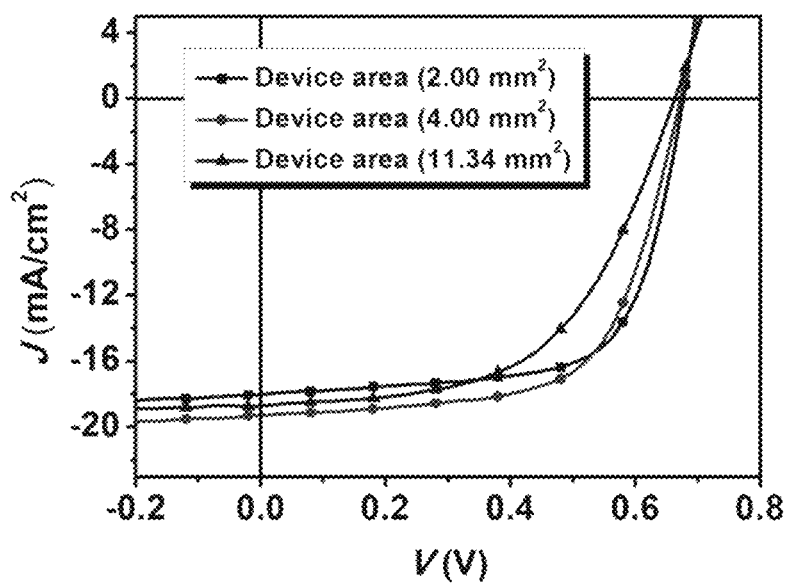
FIG. 14A depicts an example of current-density-voltage characteristics of semi-transparent solar cells based on PCE-10:BT-CIC (1:1.5, w/w) with different device areas.
Figure 14B:
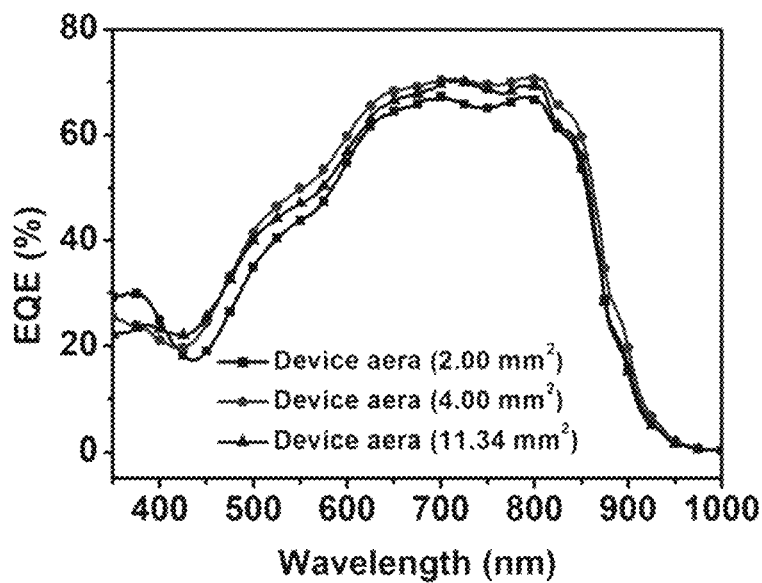
FIG. 14B depicts an example of an external quantum efficiency (EQE) spectra of semi-transparent solar cells based on PCE-10:BT-CIC (1:1.5, w/w) with different device areas.
Figure 15A:
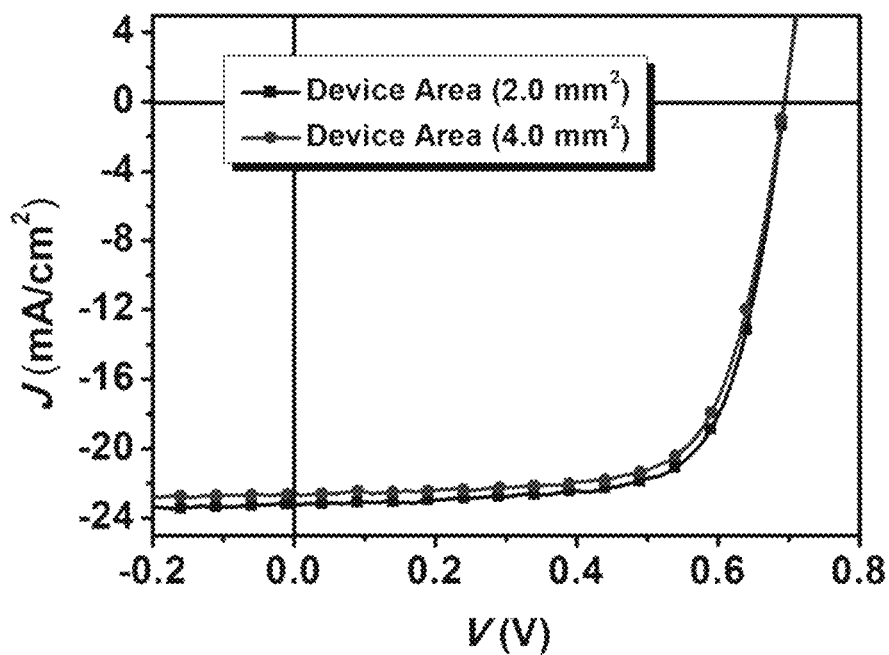
FIG. 15A depicts an example of current-density-voltage characteristics of single-junction solar cells based on PCE-10:BT-CIC (1:1.5, w/w) with different device areas.
Figure 15B:
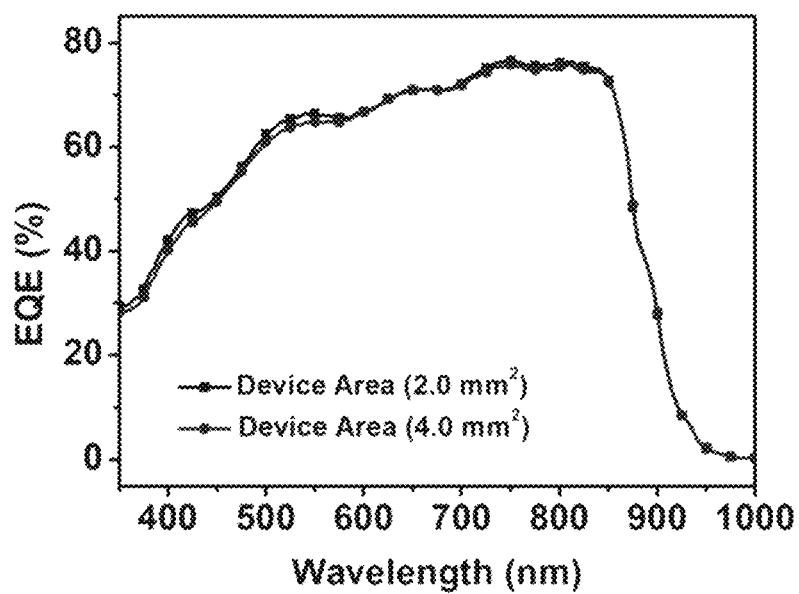
FIG. 15B depicts an example of external quantum efficiency (EQE) spectra of single-junction solar cells based on PCE-10:BT-CIC (1:1.5, w/w) with different device areas.

The significant improvement in J$_{sc}$ for the BT-CIC OPV is attributed to its red-shifted absorption that provides solar spectral response into the NIR, and its improved stacking leading to large and ordered aggregates compared to the other NFA. The EQE vs. wavelength spectrum is shown in FIG. 11B. The long wavelength cut-off of BT-CIC at λ=950 nm is red-shifted by ~80 nm compared to BT-IC, and ~170 nm compared to PC$_{71}$BM. The EQE of the BT-CIC OPV reaches 75%, between λ=650 nm and 850 nm. The integrated J$_{sc}$=21.3 mA cm$^{-2}$ is within 5% of the solar simulation measurement.

A transparency window between the visible wavelengths of 400 nm and 650 nm for the BT-CIC OPV was exploited in semi-transparent OPVs (STOPVs) with the structure: ITO/ZnO (18 nm)/PCE-10: BT-CIC (120 nm)/MoO$_3$ (15 nm)/Ag (x). To determine the trade-off between transparency and efficiency, STOPVs with Ag thicknesses of x=10, 15 and 20 nm were fabricated. The J-V, transmission and EQE spectral characteristics for the devices are shown in FIGS. 12A-12B, FIG. 13, FIGS. 14A-14B, and FIGS. 15A-15B, and the results are summarized in Tables 2-4. The average visible transmittance (AVT) of the devices, which is calculated from the simple arithmetic mean of the transmittances from 400 to 650 nm, varied from 26±0.5% to 43±1.5%, with 20 nm≥x≥10 nm. For x=10 nm, the STOPV showed PCE=7.1±0.1%, and for x=20 nm, PCE=8.2±0.2, which are measured from ITO side, no object behind the cells. The J$_{sc}$ significantly decreased compared to the opaque devices due to the reduced reflectivity of the thin cathode, leading to the lower light intensity within the active layer. A decreased V$_{oc}$ and FF were also found in the STOPVs due to increased sheet resistance of the thin Ag electrodes.

TABLE 2

Operating characteristics of semi-transparent PCE-10:BT-CIC OPVs with different Ag cathode thicknesses under simulated AM 1.5 G, 100 mW cm$^{-2}$ illumination.

| Ag Thickness [nm] | J$_{sc}$[a] [mA/cm$^2$] | V$_{oc}$ [V] | FF [%] | PCE[b] [%] | AVT [%] | R$_{series}$ [Ω cm$^2$] | R$_{sheet}$ [Ω/sq] |
|---|---|---|---|---|---|---|---|
| 10 | 15.8 ± 0.1 (15.2) | 0.68 ± 0.01 | 66.2 ± 1.2 | 7.1 ± 0.1 | 43 ± 1.5 | 2.1 ± 0.1 | 28.0 ± 1.2 |
| 15 | 17.0 ± 0.3 (16.0) | 0.68 ± 0.01 | 67.1 ± 0.9 | 7.7 ± 0.1 | 33 ± 1.1 | 1.7 ± 0.1 | 4.3 ± 0.3 |
| 20 | 18.0 ± 0.3 (17.1) | 0.68 ± 0.01 | 67.5 ± 1.8 | 8.2 ± 0.2 | 26 ± 0.5 | 1.7 ± 0.1 | 2.4 ± 0.5 |

[a] The values in parentheses are calculated from the integral of the EQE spectrum.
[b] The average value is based on measurement of 8 devices.

TABLE 3

Operating characteristics of semi-transparent PCE-10:BT-CIC OPVs with different device areas under simulated AM 1.5 G, 100 mW cm$^{-2}$ illumination.

| Device Area [mm$^2$] | $J_{sc}$ [mA/cm$^2$] | $V_{oc}$ [V] | FF [%] | PCE [%] |
|---|---|---|---|---|
| 2.00 | 18.0 (17.1)[a] | 0.68 | 67.5 | 8.2 |
| 4.00 | 19.3 (18.6)[a] | 0.68 | 64.1 | 8.4 |
| 11.34 | 18.6 (17.8)[a] | 0.67 | 55.3 | 7.0 |

[a] The values in parentheses are calculated from the integral of the EQE spectrum.

TABLE 4

Operating characteristics of PCE-10:BT-CIC single junction solar cells with different device areas under simulated AM 1.5 G, 100 mW cm$^{-2}$ illumination.

| Device Area [mm$^2$] | $J_{sc}$ [mA/cm$^2$] | $V_{oc}$ [V] | FF [%] | PCE [%] |
|---|---|---|---|---|
| 2.0 | 23.2 (22.0)[a] | 0.69 | 71.2 | 11.4 |
| 4.0 | 22.6 (21.8)[a] | 0.69 | 71.0 | 11.1 |

[a] The values in parentheses are calculated from the integral of the EQE spectrum.

Figure 16:
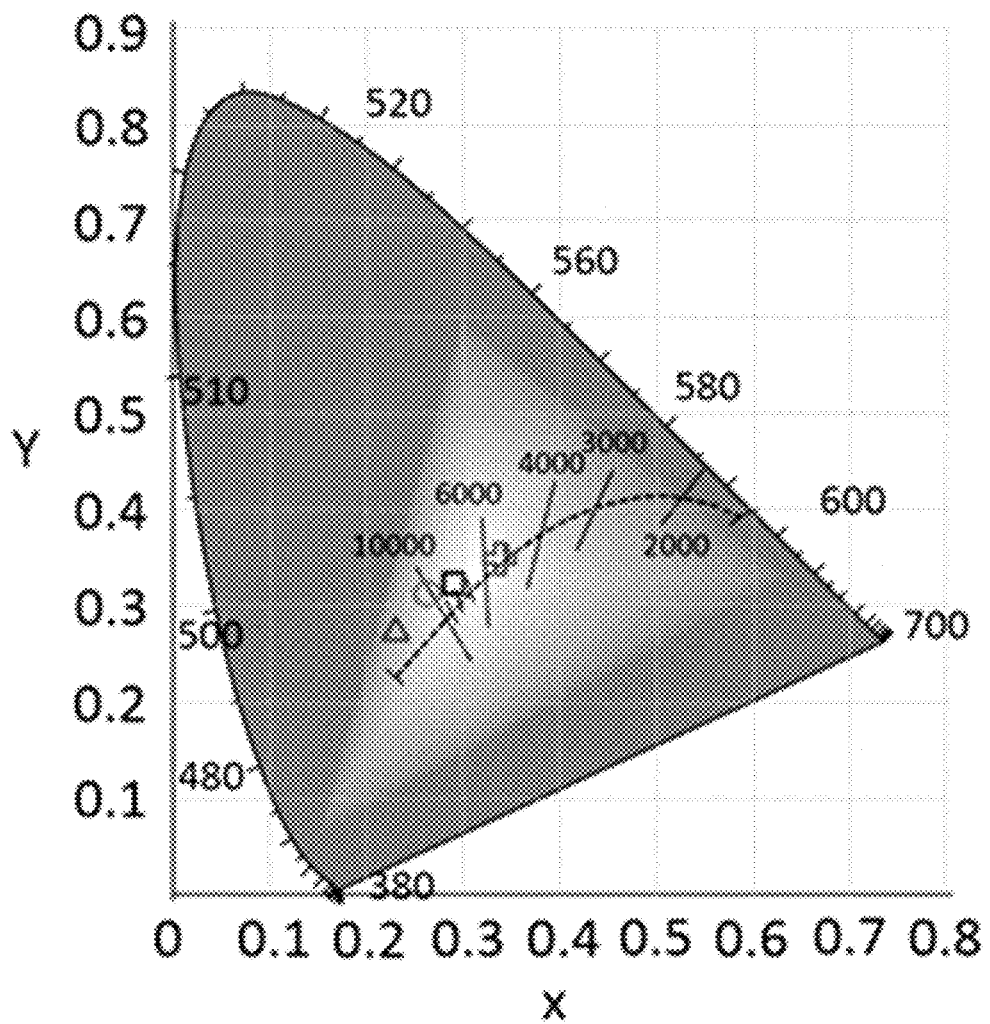
FIG. 16 depicts an example of CIE coordinates of the transmission spectra of devices with different Ag thicknesses using a AM1.5G solar simulated input spectrum (denoted by '✧'), 10 nm thick Ag ('□' square), 15 nm Ag ('O' circle) and 20 nm Ag ('Δ' triangle).

Semi-transparent OPVs have potential applications as power-generating windows for buildings and automobiles. Hence, their visual appearance must also be quantified. The device appearance was examined using AM1.5G simulated solar illumination. The 1931 CIE chromaticity coordinates are shown in FIG. 16. The transmitted light of the device with a 10 nm thick Ag cathode has color coordinates of (0.29,0.32), which is close to the D75 standard illuminant (a white light source with color rendering index of CRI=100 and correlated color temperature of CCT=7500 K). The STOPV also exhibited CRI=91 and CCT=7784 K. This high CRI indicates that the illumination through the OPV window can accurately render the color of an object, giving it only a slightly bluish tint.

Device Fabrication and Characterization

Pre-patterned ITO-coated glass substrates with sheet resistances of 15 Ω/sq were purchased from Lumtec. The substrate surface was detergent and solvent cleaned prior to deposition, followed by CO$_2$ snow cleaning and exposure to ultraviolet-ozone for 20 min1. A ZnO layer (ca. 25 nm) was spun cast from a ZnO precursor solution onto the substrates and then thermally annealed at 150° C. for 30 min in air. The active layer (ca. 130 nm thick) was then spin-coated from the blend solutions (total concentration 25 mg mL$^{-1}$), followed by thermal annealing at 150° C. for 10 min. The MoO$_3$ and Ag films were deposited at 0.6 nm/s in a high vacuum chamber with a base pressure of 10$^{-7}$ torr. The deposition rates and thicknesses were measured using quartz crystal monitors and calibrated post-growth by variable-angle spectroscopic ellipsometry. The areas of the OPVs were defined by the patterned ITO anode and depositing the Ag cathode through shadow a masks, therefore, the device areas of the normal cells are 2 mm$^2$. Semitransparent OPVs (STOPVs) used the same fabrication procedures as the opaque cells. The device performance was measured with illumination from the ITO substrate side, and there was no object behind the cells. The MoO$_3$ and Ag films were deposited at 0.6 and 0.05 nm/s, respectively.

Following fabrication, current density-voltage (J-V) characteristics and spectrally resolved external quantum efficiencies (EQE) were measured in a glove box filled with ultrapure N$_2$ (<0.1 ppm). A solar simulator provided AM 1.5G illumination (ASTM G173-03) whose 300 W Xe lamp intensity was calibrated with a National Renewable Energy Laboratory-traceable Si reference cell. The illumination intensity was adjusted using neutral density filters. Errors quoted account for variations from three or more cells measured, as well as an additional systematic error of 5% for JSC and PCE. Focused monochromatic light from a 150 W Xe lamp that under-filled the device area was used for measuring EQE. The OPV current from light chopped at 200 Hz was input to a lock-in amplifier. The responsivities of both the device and a calibrated Si photodetector were compared to calculate EQE.

Grazing Incidence X-Ray Diffraction (GIXD)

GIXD of the thin films were performed at beamline 7.3.3 at the Advanced Light Source (ALS), Lawrence Berkeley National Lab (LBNL). The x-ray energy was 10 keV and operated in the top off mode. The scattering intensity was recorded on a 2D image plate (Pilatus 1M) with a pixel size of 172 μm (981×1043 pixels). The samples were approximately 10 mm long in the direction of the beam path, and the detector was located at a distance of 300 mm from the sample center (distance calibrated by an AgB reference). The incidence angle was 0.16° (above critical angle) for GIXD measurement. OPV samples were prepared on PEDOT:PSS coated Si wafers in a similar manner to the devices. Resonant soft x-ray diffraction with photon energy of 286.2 eV was performed at beamline 11.0.1.2 of LBNL. Thin films were transferred onto a Si$_3$N$_4$ substrate and the experiment was done in the transition mode.

Optical and Electrochemical Characterization

The absorbance of solid films was measured by UV-VIS (Perkin Elmer 1050). Cyclic voltammetry employed acetonitrile with 0.1 M of tetrabutylammonium hexafluorophosphate at a scan rate of 100 mV s-1. ITO, Ag/AgCl and Pt mesh were used as working, reference and counter electrode, respectively.

Space Charge Limited Current Mobility Measurement

Hole and electron mobilities were measured using the device structures: ITO/PEDOT:PSS (40 nm)/PCE-10:BT-IC (106 nm) or PCE-10:BT-CIC (108 nm)/Au for hole-only measurements and ITO/ZnO (35 nm)/PCE-10:BT-CIC (104 nm) or PCE-10:BT-CIC (110 nm)/PDINO$_2$ (10 nm)/Al for electron-only measurements. The space charge limited current mobilities were calculated from the J-V characteristics using:

$$J = \frac{9\varepsilon_r\varepsilon_0\mu V^2}{8L^3}$$

where J is the current density, $\varepsilon_r$=4 is the relative dielectric constant of active layer material, $\varepsilon_0$ is the permittivity of free space, μ is the mobility of holes or electrons, L is the thickness of the active layer, and V is the applied voltage.

Simulation Methods—Monte Carlo Calculations

In the model, a simple cubic lattice was built with the lattice spacing of 2 nm. We assigned the energy levels of each molecular site using a Gaussian distribution function $f_{(Ei)}$ centered at HOMO or LUMO ($E_0$), $$f_{(Ei)} = \frac{1}{\sqrt{2\pi\sigma^2}}\exp\left(-\frac{(E_i - E_0)^2}{2\sigma^2}\right)$$

where σ is the energy disorder of the material.

Energy offset between the LUMO/HOMO of donor and acceptor sites are considered. The electron or hole hopping rate is determined by the Miller-Abrahams transfer:

$$\gamma_{if} = \begin{cases} \gamma_0 \exp\left(-\dfrac{E_f - E_i + q \cdot \vec{r_{if}} \cdot \vec{F} + E_C}{k_B T}\right) & (\Delta E > 0) \\ \gamma_0 & (\Delta E \le 0) \end{cases}$$

where $\Delta E = E_f - E_i + q \overline{r_{if}} \cdot \overline{F} + E_C$. $E_f$ and $E_i$ are the energy of the final and initial sites, respectively. $r_{if}$ is the distance between the initial and final sites. $E_C$ is the coulombic binding energy between electron and hole when they are at different sites. We start our simulation by putting the electron and hole at the same site near the interface (an exciton state), where $E_C$ is replaced with an exciton binding energy ($E_b$). The exciton recombination rate is from the experimental results of time-resolved photoluminescence measurement. We repeat the Monte Carlo simulation for 1000 times and find the escape yield of electron or hole from the interface.

Simulation Methods—Quantum Chemical Calculations:

Quantum chemical calculations were carried out using DFT/TDDFT in the Gaussian 09w package. The geometries of molecules were optimized using the B3LYP functional and 6-31G(d) basis set, paired with a polarizable continuous medium (PCM) model using the dielectric constant of the thin film. Based on the optimized structures, TDDFT was used to obtain the charge densities and energy levels of excited states based on the B3LYP functional and 6-31G(d) basis set.

While the present claim scope has been described with reference to specific examples, which are intended to be illustrative only and not to be limiting of the claim scope, it will be apparent to those of ordinary skill in the art that changes, additions and/or deletions may be made to the disclosed embodiments without departing from the spirit and scope of the claims.

The foregoing description is given for clearness of understanding only, and no unnecessary limitations should be understood therefrom, as modifications within the scope of the claims may be apparent to those having ordinary skill in the art.

What is claimed is:

1. An acceptor for a solar cell, the acceptor comprising one of the following structures:

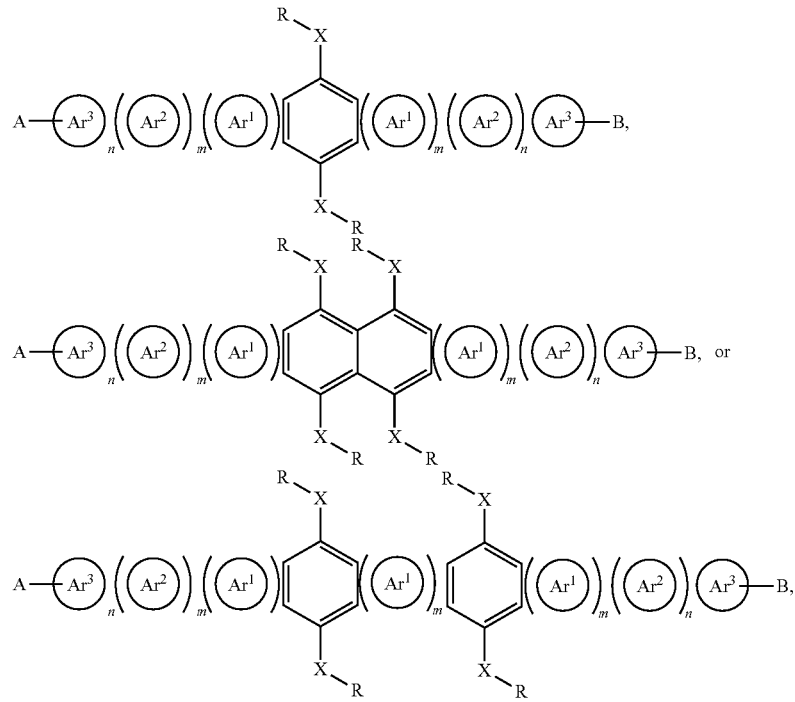

wherein:

A and B are individually selected from the group consisting of:

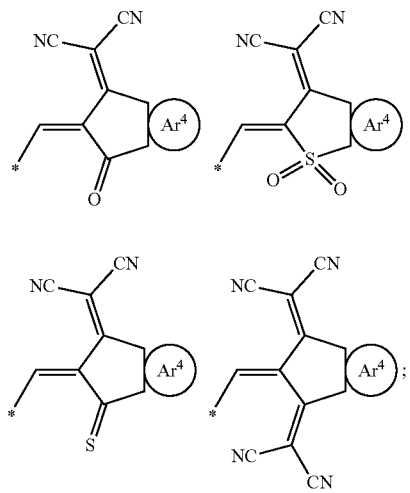

each Ar¹ is individually selected from the group consisting of:
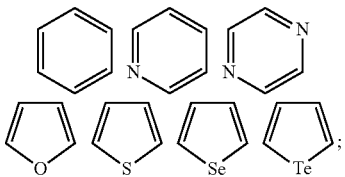
each Ar² is individually selected from the group consisting of:
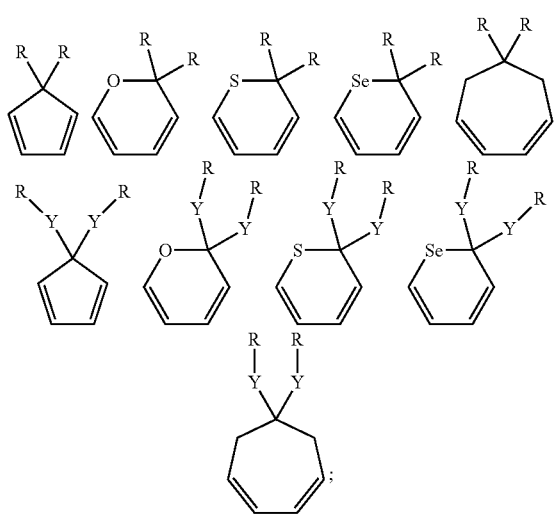
each Ar³ is individually selected from the group consisting of:
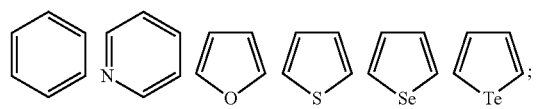
each Ar⁴ is individually selected from the group consisting of:
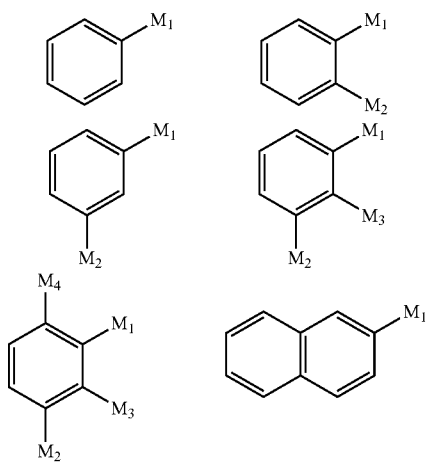
-continued
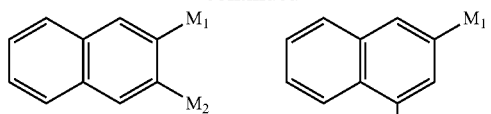
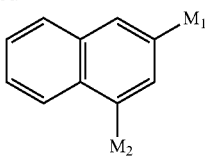
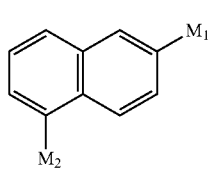
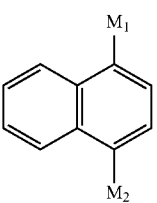
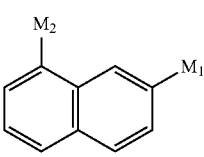
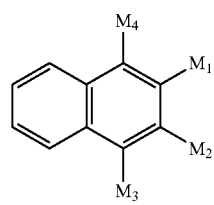
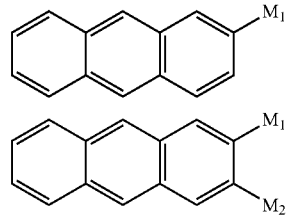
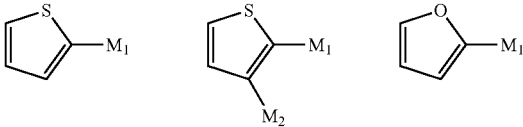
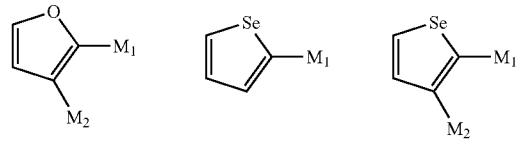
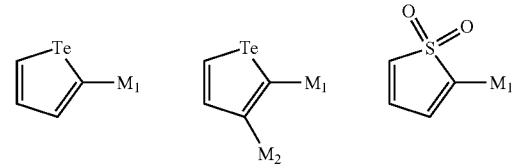
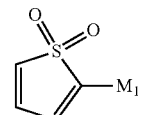
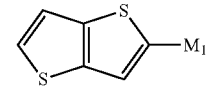
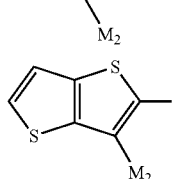
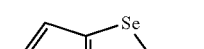
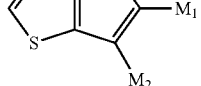
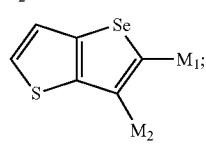

M₁-M₄ are individually selected from the group consisting of hydrogen, fluorine, chlorine, bromine, iodine, astatine, and a cyano group, wherein at least one of $M_1$-$M_4$ is a halogen;

each R is individually a $C_1$-$C_{20}$ hydrocarbon or an aromatic hydrocarbon;

each X is individually selected from the group consisting of oxygen, carbon, hydrogen, sulfur, selenium, and nitrogen;

each Y is individually selected from the group consisting of:

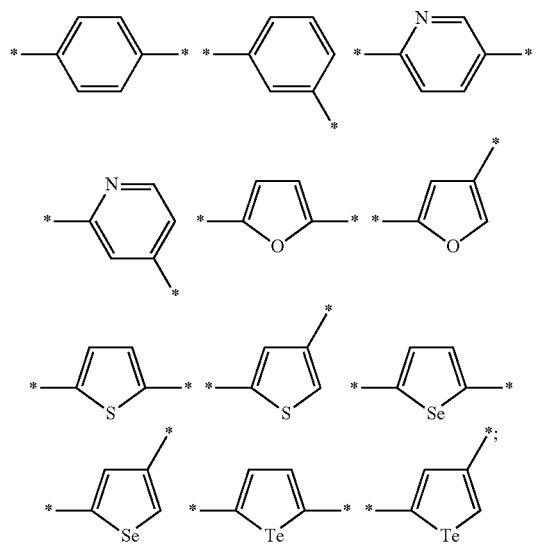

each m is an integer from 0 to 10; and
each n is an integer from 0 to 10.

2. The acceptor of claim 1, wherein each $Ar^1$ is:

3. The acceptor of claim 1, wherein each $Ar^3$ is:

4. The acceptor of claim 1, wherein A or B is:

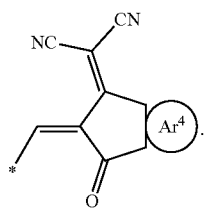

5. The acceptor of claim 1, wherein $Ar^4$ is:

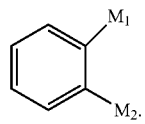

6. The acceptor of claim 1, wherein A or B is:

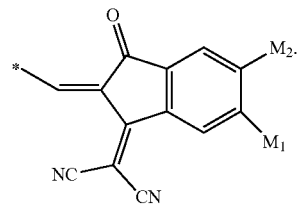

7. The acceptor of claim 1, wherein at least one of $M_1$-$M_4$ is chloride.

8. The acceptor of claim 1, wherein each R is 2-ethylhexyl.

9. The acceptor of claim 1, wherein each R is selected from the group consisting of:

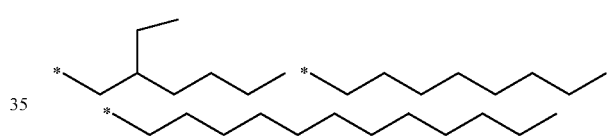

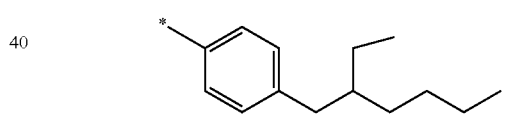

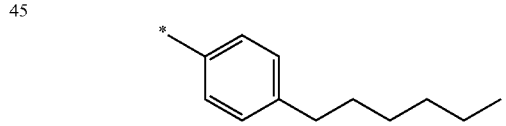

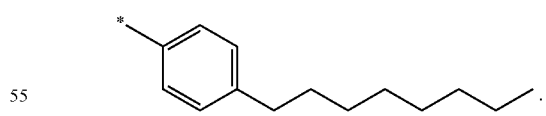

10. The acceptor of claim 1, wherein each Y is:

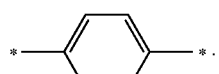

11. The acceptor of claim 1, wherein the acceptor has one of the following structures C1-C11:

C1
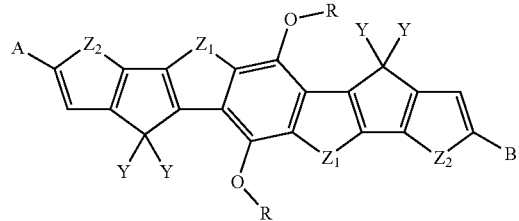
C2
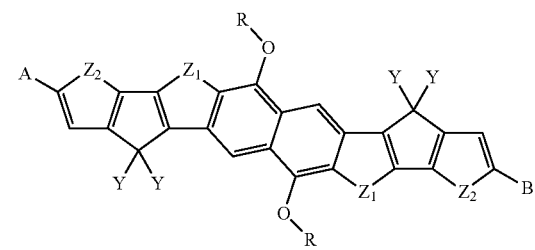
C3
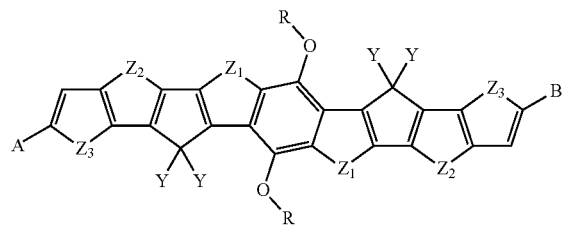
C4
C5
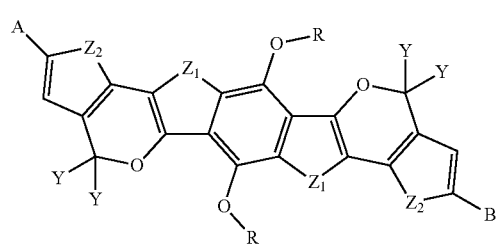
C6
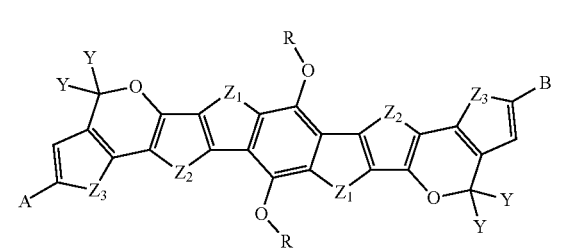
C7
C8
C9
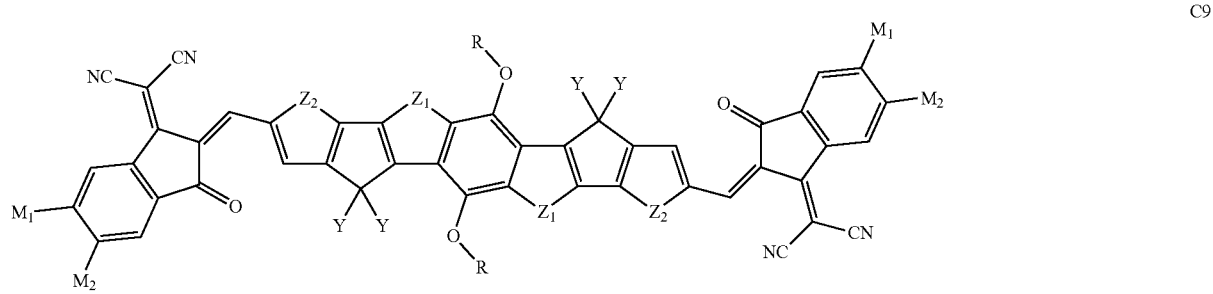
C10
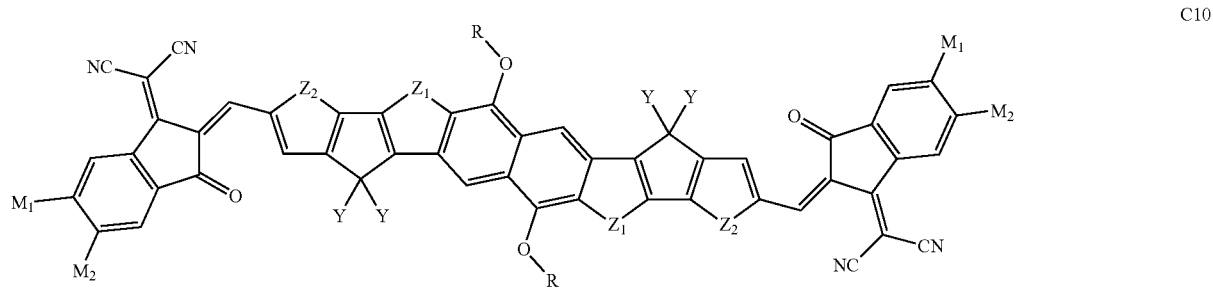

-continued
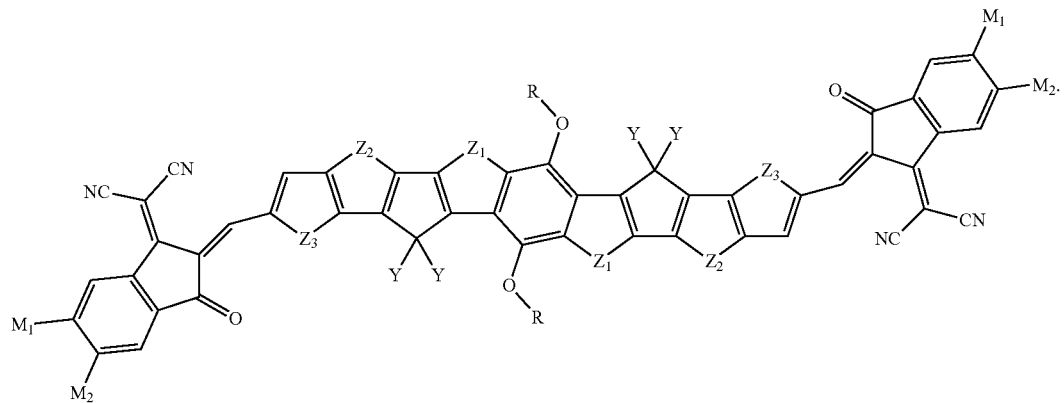
12. The acceptor of claim 11, wherein $Z_1$, $Z_2$, and $Z_3$ are sulfur.
13. The acceptor of claim 1, wherein the acceptor has one of the following structures:
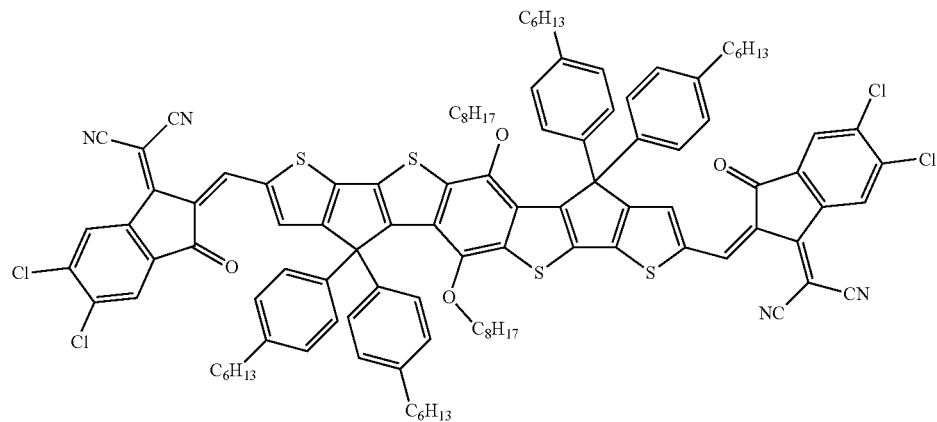
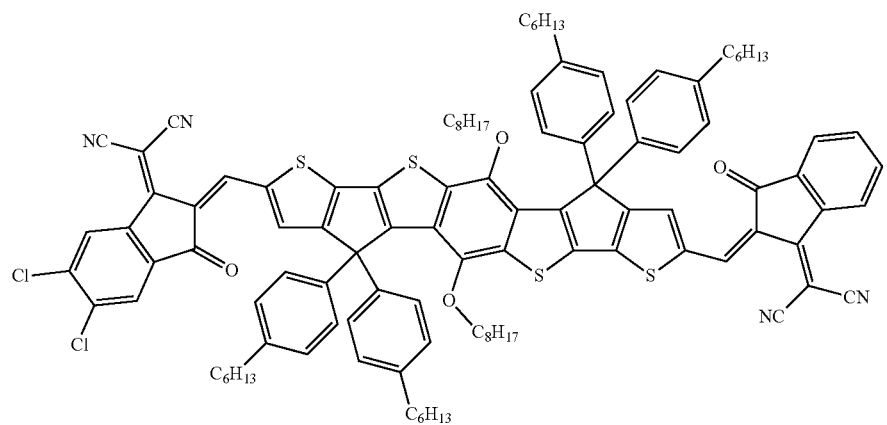

-continued
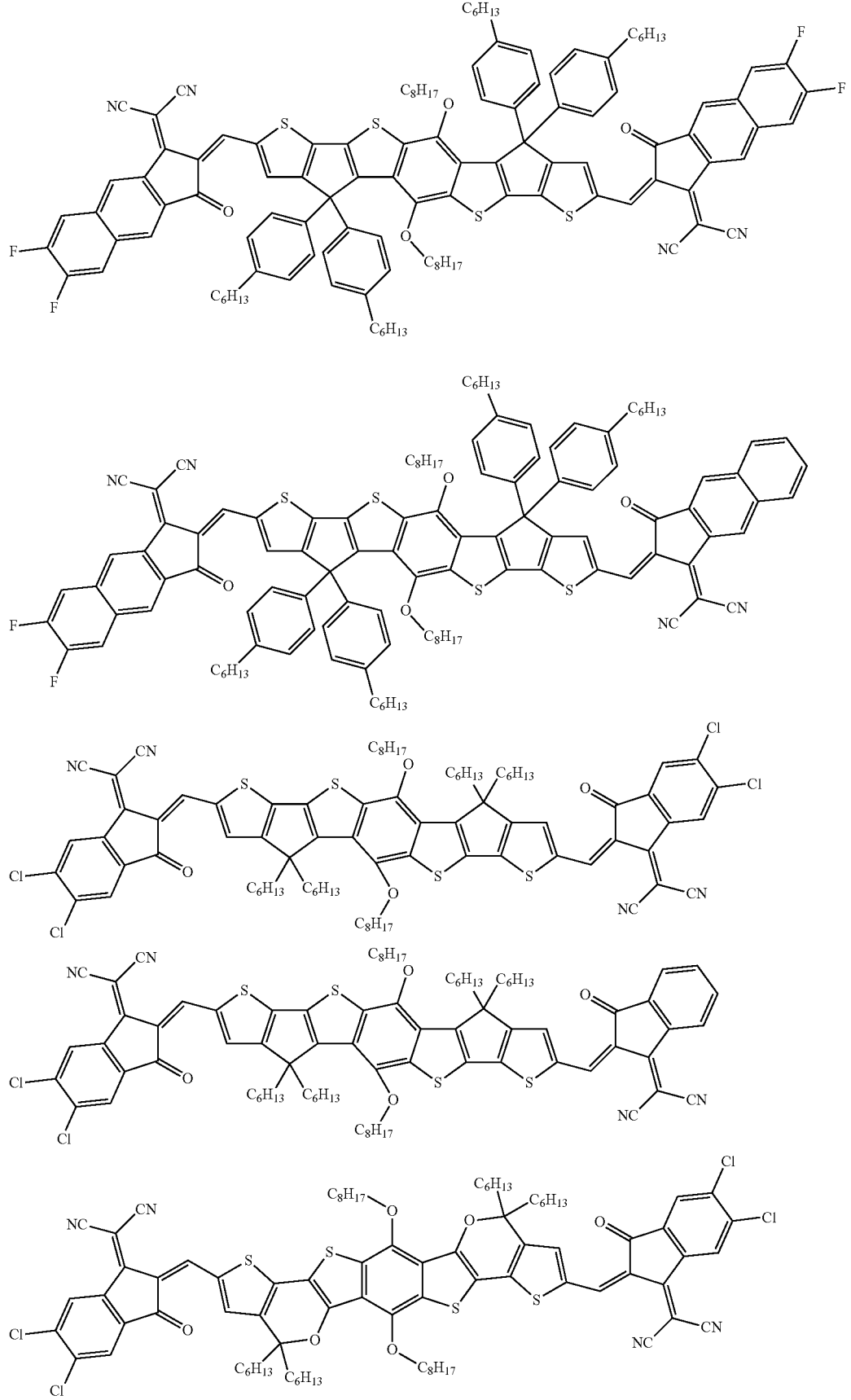

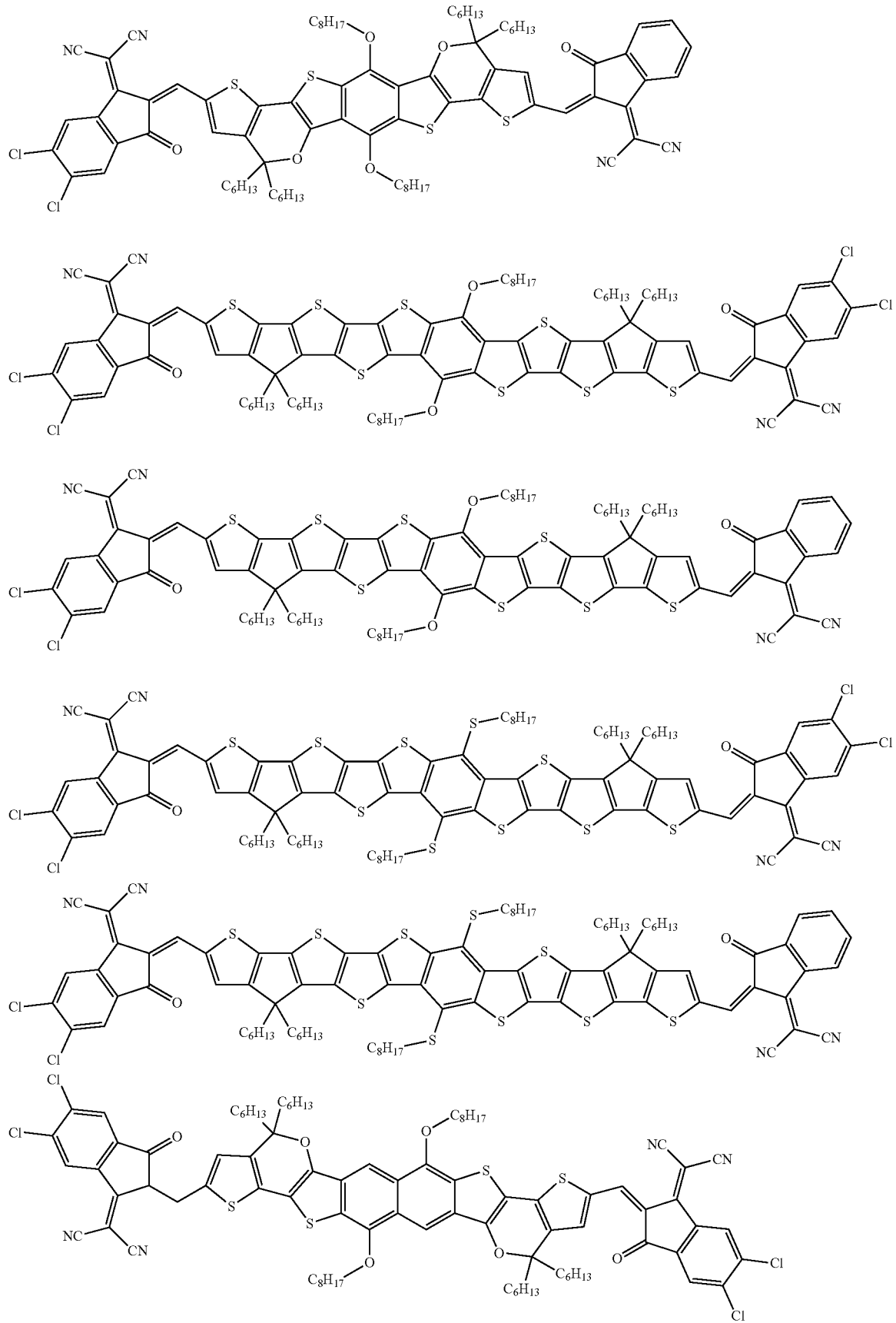

-continued
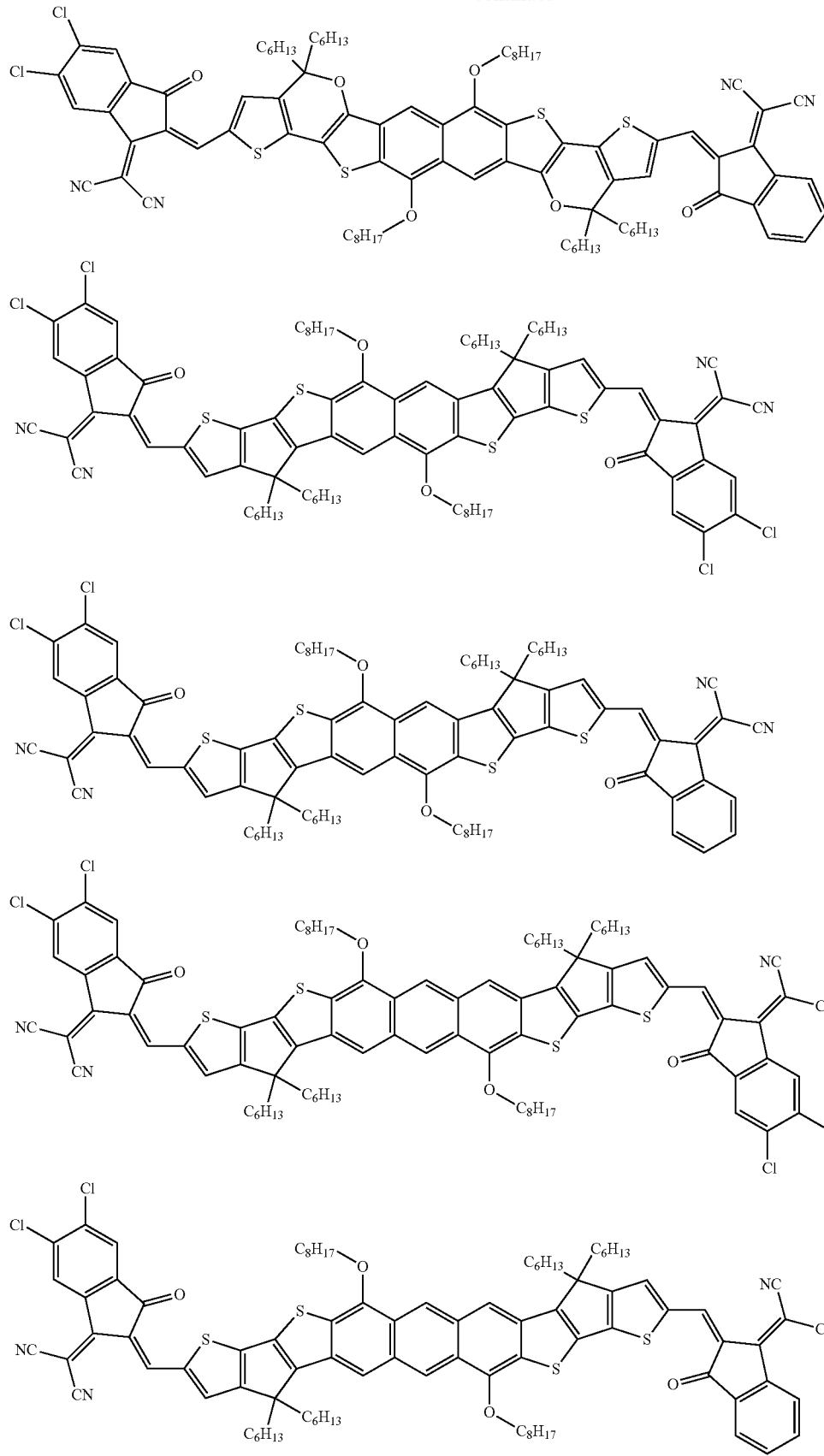

14. The acceptor of claim 1, wherein the acceptor has the following structure:

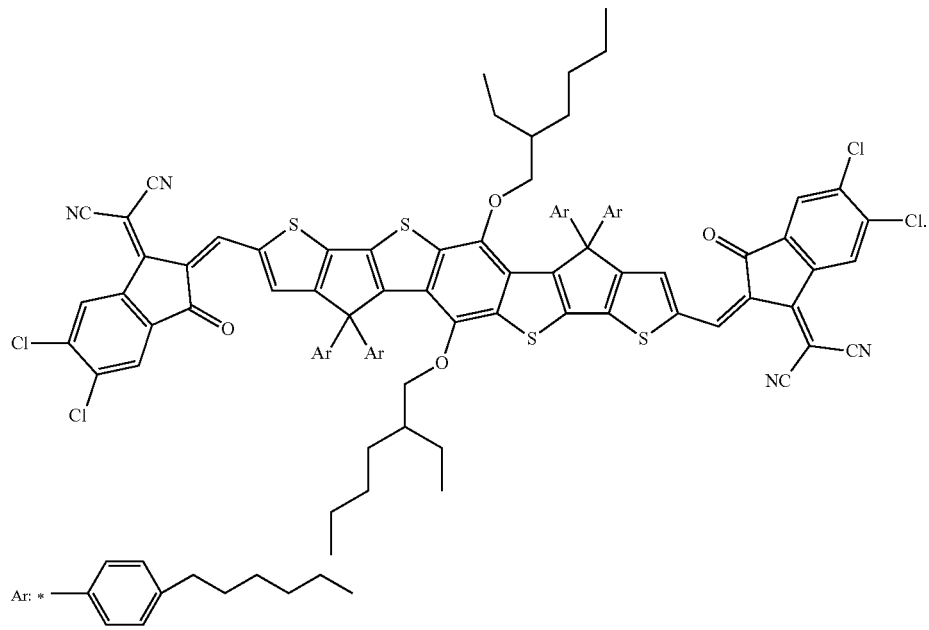

15. The acceptor of claim 1, wherein the solar cell having the acceptor has a power conversion efficiency of at least 11%.

16. The acceptor of claim 1, wherein the solar cell having the acceptor has an open circuit voltage of at least 0.7 Volts.

17. The acceptor of claim 1, wherein the solar cell having the acceptor has a fill factor of at least 70%.

18. The acceptor claim 1, wherein the solar cell having the acceptor has a short circuit current of between 20-25 mA/cm$^2$.

19. The acceptor of claim 1, wherein the solar cell having the acceptor has an external quantum efficiency of at least 75%, as measured between wavelengths of 650-850 nm and providing a transparency window between wavelengths of 400-650 nm.

20. The acceptor of claim 1, wherein a length of the acceptor is at least 25 angstroms.

* * * * *